United States Patent
Datta et al.

(10) Patent No.: US 6,770,458 B1
(45) Date of Patent: Aug. 3, 2004

(54) PURIFIED AND ISOLATED SERINE-THREONINE KINASE RECEPTORS ASSOCIATED PROTEIN AND USE OF SAME IN THE MODULATION OF THE BIOLOGICAL ACTIVITY OF TGF-β

(75) Inventors: Pran K. Datta, Nashville, TN (US); Harold L. Moses, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 09/856,836

(22) PCT Filed: Dec. 10, 1999

(86) PCT No.: PCT/US99/29267
§ 371 (c)(1),
(2), (4) Date: Jul. 11, 2001

(87) PCT Pub. No.: WO00/34310
PCT Pub. Date: Jun. 15, 2000

Related U.S. Application Data

(60) Provisional application No. 60/111,668, filed on Dec. 10, 1998.

(51) Int. Cl.[7] .......................... C12N 15/00; C12N 1/21; C12P 21/00; C07H 21/04
(52) U.S. Cl. .................... 435/69.1; 435/70.1; 435/70.3; 435/71.1; 435/320.1; 435/325; 435/252.3; 536/23.1; 536/23.5; 514/2
(58) Field of Search ................. 435/69.1, 70.1, 435/70.3, 71.1, 320.1, 325, 194; 536/23.1, 23.5, 24.3; 514/2

(56) References Cited

U.S. PATENT DOCUMENTS

| | | | |
|---|---|---|---|
| 4,742,003 A | 5/1988 | Derynck et al. | |
| 4,816,561 A | 3/1989 | Todaro | |
| 4,863,899 A | 9/1989 | Todaro | |
| 5,834,240 A | * 11/1998 | Bandman et al. | .......... 435/69.1 |

* cited by examiner

*Primary Examiner*—Lorraine Spector
*Assistant Examiner*—Jegatheesan Seharaseyon
(74) *Attorney, Agent, or Firm*—Jenkins, Wilson & Taylor, P.A.

(57) ABSTRACT

Isolated and purified proteins and nucleic acids which modulate TGF-β biological activity, including TGF-β signal transduction. Particularly, a novel serine-threonine kinase receptors associated protein (STRAP) and cDNA encoding the same are disclosed. Recombinant host cells, recombinant nucleic acids and recombinant proteins are also disclosed, along with methods of producing each. Isolated and purified antibodies to STRAP, and methods of producing the same, are also disclosed. STRAP is characterized as having TGF-β modulating activity. Thus, therapeutic methods involving this activity are also disclosed.

13 Claims, 18 Drawing Sheets

FIG. 2A

```
    MAMRQTPLTCSGHTRPVVDLAFSGITPYGYFLISACKDGKPMLRQGDTGDWIGTELGHKGAVWGATLNKDATKAA    75
    TAAADETAKVWDAVSGDELMTLAHKHIVKTVDFTODSNYLLTGGODKLLRIYDLNKPEAEPKEISGHTSGIKKAL   150
    WCSDDKOILSADDKTVRLMDHATMTEVKSLNFMSVSSMEYIPEGEILVITYGRSIAFHSAVSLEPIKSFEAPAT    225
                                                         STRAP (1-294)
    INSASLHPEKEFIVAGGEDFKLYKYDNSGEELESYKGHFGPIHCVRESPDGELYASGSEDGTLRLWQTVVGKTY    300
    GLMKCVLPEEDSGELAKPKIGFPETAEEELAEEIASENSDSIYSSTPEVKA                            351
```

FIG. 2B

```
  1  MAMRQTPLTCSSHTRPVVDLAFSGITPYGYFLISACKDGKPMLRQGDTGDWIFTELGKGAVWGATLNKDATKAA    STRAP
  1  ----------KEITLQHESSTIQIKYN---REGDLFTVAKIPTVNWYSVNGERLFAVMGHIFAMCVDADMEIKHVL  TRIP-1

76  TAAADETAKVWDAVSGDELMTLAHKHIVMDFIQDSNYLLIGGQDKL------LRIYDLNKF----EAEI-KEIS   STRAP
 69  HGSADNSCRIIHCEITKQIAIKINSAVRIGFDFGGNIIMFSTIDKQMGYQCFVSFFDIRDESQIDNNEPYMKIP   TRIP-1

141  GHTSGIKKAIICSDDKQILSADDKTVRLMDHATMIE---WKSLNFMSVSSMEYIPEGEIIVITYGRSIA-FHSA   STRAP
145  ONDETKIISAMGPLGEQHAGHE-SGEINQYSAKSGEVIAVKEHSRQINDIQLSRDMVMFTASKDNIEKLFDS     TRIP-1

212  VSTFPIPSFEAPATTNSASHPEKEFIVAGGED------KLYKYDNSGEELESYKGHFGPIHCVR            STRAP
219  TTLEHQIIRTERPVNSSALSNYDHVMLWGQEAMDVITTSIRIGKEARFFHLAFEEFGRVMGEGEIINSVA       TRIP-1

273  SPDGELYASGSEDGTLRLMQTVVGKIYGLMKCVLPEEDSGELAKPKIGFPETAEEELAEEIASENSDSIYSSTP   STRAP
293  FDKKSGSGCHLQVET-----HY-------FDEQIFEF                                         TRIP-1

348  AVKA   STRAP
322  FFEA   TRIP-1
```

Steps: 1) Anti-Flag IP
2) Elute with Flag peptide
3) Anti-Myc IP
4) Anti-HA immunobloting

SEQUENCE LISTING

```
<160> NUMBER OF SEQ ID NOS: 2

<210> SEQ ID NO 1
<211> LENGTH: 1630
<212> TYPE: DNA
<213> ORGANISM: Mus sp.
<220> FEATURE:
<221> NAME/KEY: CDS
<222> LOCATION: (86)..(1138)
<221> NAME/KEY: misc_feature
<222> LOCATION: (143)
<223> OTHER INFORMATION: n=t or a, Xaa=Leu or Ile
<221> NAME/KEY: misc_feature
<222> LOCATION: (431)
<223> OTHER INFORMATION: n=c or a, Xaa=Leu or Ile
<221> NAME/KEY: misc_feature
<222> LOCATION: (776)
<223> OTHER INFORMATION: n=c or a, Xaa=Leu or Ile
<221> NAME/KEY: misc_feature
<222> LOCATION: (1004)
<223> OTHER INFORMATION: n=c or a, Xaa=Leu or Ile

<400> SEQUENCE: 1
tttaccgcta ccggtaggga ccgtgagtgg cggcaggccg gctctccggc gctcccctcc      60
cctcctccct ccctccctgt ccgcc atg gcc atg agg cag acg ccg ctc act     112
                              Met Ala Met Arg Gln Thr Pro Leu Thr
                                1               5 tgc tcg ggc cac acg cgg ccc gtg gtg gat ntg gcc ttc agc ggc atc      160
Cys Ser Gly His Thr Arg Pro Val Val Asp Xaa Ala Phe Ser Gly Ile
 10              15                  20                  25 acg cct tac ggc tac ttt ctg atc agc gct tgc aaa gat ggc aag ccc      208
Thr Pro Tyr Gly Tyr Phe Leu Ile Ser Ala Cys Lys Asp Gly Lys Pro
                 30                  35                  40 atg ctc cgc cag gga gat aca gga gac tgg att gga aca ttt ttg ggt      256
Met Leu Arg Gln Gly Asp Thr Gly Asp Trp Ile Gly Thr Phe Leu Gly
             45                  50                  55 cat aaa ggt gct gtt tgg ggt gca aca ttg aat aag gat gcc acc aaa      304
His Lys Gly Ala Val Trp Gly Ala Thr Leu Asn Lys Asp Ala Thr Lys
         60                  65                  70
```

```
gct gcg aca gca gct gca gac ttc aca gcc aaa gta tgg gat gcg gtc    352
Ala Ala Thr Ala Ala Ala Asp Phe Thr Ala Lys Val Trp Asp Ala Val
     75                  80                  85 tca gga gat gaa ttg atg acc ctg gct cat aag cac att gtc aag act    400
Ser Gly Asp Glu Leu Met Thr Leu Ala His Lys His Ile Val Lys Thr
 90                  95                 100                 105 gtg gat ttc aca cag gat agc aat tac ctg nta act ggg gga cag gat    448
Val Asp Phe Thr Gln Asp Ser Asn Tyr Leu Xaa Thr Gly Gly Gln Asp
                110                 115                 120 aaa ctg ctg cgc ata tat gac ttg aac aaa cct gaa gca gaa cct aag    496
Lys Leu Leu Arg Ile Tyr Asp Leu Asn Lys Pro Glu Ala Glu Pro Lys
            125                 130                 135 gaa atc agt ggc cac act tct ggt att aaa aag gct ctg tgg tgc agt    544
Glu Ile Ser Gly His Thr Ser Gly Ile Lys Lys Ala Leu Trp Cys Ser
        140                 145                 150 gac gat aaa cag atc ctt tca gcg gat gat aaa act gtt cgg ctc tgg    592
Asp Asp Lys Gln Ile Leu Ser Ala Asp Asp Lys Thr Val Arg Leu Trp
    155                 160                 165 gat cat gcc aca atg aca gaa gtg aaa tct ctg aat ttt aat atg tct    640
Asp His Ala Thr Met Thr Glu Val Lys Ser Leu Asn Phe Asn Met Ser
170                 175                 180                 185 gtt agc agc atg gag tat att cct gaa gga gag att ttg gtt att act    688
Val Ser Ser Met Glu Tyr Ile Pro Glu Gly Glu Ile Leu Val Ile Thr
                190                 195                 200 tat gga cga tct att gct ttt cat agt gca gta agt ctg gag cca att    736
Tyr Gly Arg Ser Ile Ala Phe His Ser Ala Val Ser Leu Glu Pro Ile
            205                 210                 215 aaa tcc ttt gaa gct cct gcg acc atc aat tct gcg tct ntt cat cca    784
Lys Ser Phe Glu Ala Pro Ala Thr Ile Asn Ser Ala Ser Xaa His Pro
        220                 225                 230 gag aag gag ttt ctt gtt gcg ggt gga gaa gac ttt aaa ctg tac aag    832
Glu Lys Glu Phe Leu Val Ala Gly Gly Glu Asp Phe Lys Leu Tyr Lys
    235                 240                 245 tat gat tat aac agt gga gaa gag tta gaa tcc tac aaa ggt cac ttt    880
Tyr Asp Tyr Asn Ser Gly Glu Glu Leu Glu Ser Tyr Lys Gly His Phe
250                 255                 260                 265 ggt ccc att cac tgt gtg aga ttc agt cct gat ggg gaa ctc tat gcc    928
Gly Pro Ile His Cys Val Arg Phe Ser Pro Asp Gly Glu Leu Tyr Ala
                270                 275                 280 agc ggt tct gaa gat ggg aca ttg aga ttg tgg caa act gtg gta gga    976
Ser Gly Ser Glu Asp Gly Thr Leu Arg Leu Trp Gln Thr Val Val Gly
            285                 290                 295 aag acc tat ggc ctg tgg aaa tgc gtg ntt cct gag gaa gac agc ggg   1024
Lys Thr Tyr Gly Leu Trp Lys Cys Val Xaa Pro Glu Glu Asp Ser Gly
        300                 305                 310 gaa ctg gca aag cca aag atc gga ttt cca gaa aca gca gag gaa gag   1072
Glu Leu Ala Lys Pro Lys Ile Gly Phe Pro Glu Thr Ala Glu Glu Glu
    315                 320                 325 ctg gca gaa gaa att gct tca gag aat tca gat tcc atc tat tca tca   1120
Leu Ala Glu Glu Ile Ala Ser Glu Asn Ser Asp Ser Ile Tyr Ser Ser
330                 335                 340                 345 act cct gaa gtt aag gcc tgagcatcag acgtgtgctg ccgaaaccat          1168
Thr Pro Glu Val Lys Ala
                350 atgttcatgg actaaacaag cagagacaag catccgcctt cagagttact gtctgcctga  1228 ggcaaagagg gcagaaaata ttggggcata tgagttagct ccagtgcacg aacagctact  1288 cagtgttgcc cgtgagtgaa aatggctgag tgtctgaggt gcaggcagga ggattgtgct  1348
```

```
cacatagtgc catagcctgc tgtttggaat gaaaagccaa cttacaatct ccatttttaca    1408 cctaaatttc ttttagctgt ttatgttatg aagaagaaaa atatattggc ctattttttct   1468 gactttccct taaagaagaa tgccttttttg tccttgccta gtgatgaaga ggaggaaata   1528
catgataaag taaccggttt gatctctttc attgtacaag gactgcttca gaacagctca    1588
tatttttagt tatctaaata aaatgcctct aaaataaaaa aa                        1630
```

<210> SEQ ID NO 2
<211> LENGTH: 351
<212> TYPE: PRT
<213> ORGANISM: Mus sp.
<220> FEATURE:
<221> NAME/KEY: misc_feature
<222> LOCATION: (20)
<223> OTHER INFORMATION: Xaa=Leu or Ile
<221> NAME/KEY: misc_feature
<222> LOCATION: (116)
<223> OTHER INFORMATION: Xaa=Leu or Ile
<221> NAME/KEY: misc_feature
<222> LOCATION: (231)
<223> OTHER INFORMATION: Xaa=Leu or Ile
<221> NAME/KEY: misc_feature
<222> LOCATION: (307)
<223> OTHER INFORMATION: Xaa=Leu or Ile

<400> SEQUENCE: 2

```
Met Ala Met Arg Gln Thr Pro Leu Thr Cys Ser Gly His Thr Arg Pro
  1               5                  10                  15

Val Val Asp Xaa Ala Phe Ser Gly Ile Thr Pro Tyr Gly Tyr Phe Leu
                 20                  25                  30

Ile Ser Ala Cys Lys Asp Gly Lys Pro Met Leu Arg Gln Gly Asp Thr
             35                  40                  45

Gly Asp Trp Ile Gly Thr Phe Leu Gly His Lys Gly Ala Val Trp Gly
         50                  55                  60

Ala Thr Leu Asn Lys Asp Ala Thr Lys Ala Thr Ala Ala Asp
 65                  70                  75                  80

Phe Thr Ala Lys Val Trp Asp Ala Val Ser Gly Asp Glu Leu Met Thr
                 85                  90                  95

Leu Ala His Lys His Ile Val Lys Thr Val Asp Phe Thr Gln Asp Ser
            100                 105                 110

Asn Tyr Leu Xaa Thr Gly Gly Gln Asp Lys Leu Leu Arg Ile Tyr Asp
            115                 120                 125

Leu Asn Lys Pro Glu Ala Glu Pro Lys Glu Ile Ser Gly His Thr Ser
        130                 135                 140

Gly Ile Lys Lys Ala Leu Trp Cys Ser Asp Asp Lys Gln Ile Leu Ser
145                 150                 155                 160

Ala Asp Asp Lys Thr Val Arg Leu Trp Asp His Ala Thr Met Thr Glu
                165                 170                 175

Val Lys Ser Leu Asn Phe Asn Met Ser Val Ser Ser Met Glu Tyr Ile
            180                 185                 190

Pro Glu Gly Glu Ile Leu Val Ile Thr Tyr Gly Arg Ser Ile Ala Phe
        195                 200                 205

His Ser Ala Val Ser Leu Glu Pro Ile Lys Ser Phe Glu Ala Pro Ala
    210                 215                 220

Thr Ile Asn Ser Ala Ser Xaa His Pro Glu Lys Glu Phe Leu Val Ala
225                 230                 235                 240

Gly Gly Glu Asp Phe Lys Leu Tyr Lys Tyr Asp Tyr Asn Ser Gly Glu
                245                 250                 255
```

-continued

```
Glu Leu Glu Ser Tyr Lys Gly His Phe Gly Pro Ile His Cys Val Arg
            260                 265                 270

Phe Ser Pro Asp Gly Glu Leu Tyr Ala Ser Gly Ser Glu Asp Gly Thr
        275                 280                 285

Leu Arg Leu Trp Gln Thr Val Val Gly Lys Thr Tyr Gly Leu Trp Lys
    290                 295                 300

Cys Val Xaa Pro Glu Glu Asp Ser Gly Glu Leu Ala Lys Pro Lys Ile
305             310                 315                 320

Gly Phe Pro Glu Thr Ala Glu Glu Glu Leu Ala Glu Glu Ile Ala Ser
                325                 330                 335

Glu Asn Ser Asp Ser Ile Tyr Ser Ser Thr Pro Glu Val Lys Ala
            340                 345                 350
```

US 6,770,458 B1

PURIFIED AND ISOLATED SERINE-THREONINE KINASE RECEPTORS ASSOCIATED PROTEIN AND USE OF SAME IN THE MODULATION OF THE BIOLOGICAL ACTIVITY OF TGF-β

PRIORITY APPLICATION INFORMATION

This application claims the benefit of U.S. Provisional Patent Application No. 60/111,668, filed Dec. 10, 1998, the disclosure of which is incorporated herein by reference in its entirety

GRANT STATEMENT

This work was supported by NIH grant CA 42572. The U.S. Government has certain rights in the invention.

TECHNICAL FIELD

The present invention relates generally to isolated and purified proteins and nucleic acids which modulate TGF-β biological activity, including TGF-β signal transduction. More particularly, the present invention relates to an isolated and purified serine-threonine kinase receptors associated protein and an isolated and purified polynucleic acid encoding the same.

The publications and other materials used herein to illuminate the background of the invention, and in particular cases, to provide additional details respecting the practice, are incorporated herein by reference, and for convenience, are referenced by author and date in the following text, and respectively grouped in the appended list of references.

| Table of Abbreviations | |
|---|---|
| BMP | Bone morphogenetic protein |
| BSA | Bovine serum albumin |
| CDR(s) | Complementarity determining region(s) |
| GC-MS | Gas chromatography-Mass spectroscopy |
| HAT | Cell culture media comprising hypoxanthine, aminopterin, and thymidine |
| HPLC | High pressure liquid chromatography |
| KLH | Keyhole limpet hemocyanin |
| PCR | Polymerase chain reaction |
| SMAD | Vertebrate Homologues of Sma and Mad |
| STRAP | Serine-Threonine Kinase Receptors Associated Protein |
| TGFβ | Transforming growth factor β |
| TβR-I | Transforming growth factor β receptor I |
| TβR-II | Transforming growth factor β receptor II |

BACKGROUND ART

Transforming growth factor β's (TGFβ) are a family of multifunctional cell regulatory factors produced in various forms by many types of cells (for review see Spom et al., *J. Cell Biol.* 105:1039, (1987)). Five different TGFβ's are known, and the functions of two, TGFβ-1 and TGFβ-2, have been characterized in detail. TGFβ's are the subject of U.S. Pat. Nos. 4,863,899; 4,816,561; and 4,742,003 which are incorporated by reference. TGFβ-1 and TGFβ-2 are publicly available through many commercial sources (e.g. R & D Systems, Inc. of Minneapolis, Minn.). These two proteins have similar functions and will be here collectively referred to as TGF-β.

TGF-β binds to cell surface receptors possessed by essentially all types of cells, causing profound changes in them. In some cells, TGF-β promotes cell proliferation and in others it suppresses proliferation. A marked effect of TGF-β is that it promotes the production of extracellular matrix proteins and their receptors by cells (for review see Keski-Oja et al., *J. Cell Biochem.* 33:95 (1987); Massague, *Cell* 49:437 (1987); Roberts and Sporn in "Peptides Growth Factors and Their Receptors" (Springer-Verlag, Heidelberg) (1989)).

While TGF-β, has many essential cell regulatory functions, improper TGF-β activity can be detrimental to an organism. Since the growth of mesenchyme and proliferation of mesenchymal cells is stimulated by TGF-β, some tumor cells may use TGF-β as an autocrine growth factor. Therefore, if the growth factor activity of TGF-β could be prevented, tumor growth could be controlled. In other cases the inhibition of cell proliferation by TGF-β may be detrimental, in that it may prevent healing of injured tissues. The stimulation of extracellular matrix production by TGF-β is important in situations such as wound healing. However, in some cases the body takes this response too far and an excessive accumulation of extracellular matrix ensues. An example of excessive accumulation of extracellular matrix is glomerulonephritis, a disease with a detrimental involvement of TGF-β.

Pleiotropic responses to TGF-β are mediated via ligand-induced heteromeric complex formation by type I and type II receptors. Upon ligand binding, the type if receptor (TβR-II), which is a constitutively active kinase, transphosphorylates the type I receptor (TβR-I) and activates this kinase to propagate the signals to downstream effectors, termed SMAD proteins. See Massague¢ et al., *Trends Cell Biol.* 7:187–192 (1997): Heldin et al., *Nature* 390:465–471 (1997). SMAD proteins can be classified according to their role in signaling by TGF-β family members. Pathway-restricted SMADs interact transiently with, and are phosphorylated by specific activated type I receptors. Smad2 and Smad3 mediate signaling by TGF-β and activin, whereas Smad1 and Smad5 are involved in BMP signaling. Smad4 is a common mediator of TGF-β, activin and BMP signals. Recently Smad6 and Smad7 have been shown to function as inhibitors of these signaling pathways by interfering with the activation of pathway-restricted SMADs. Although the nature and mechanism of activation of TGF-β receptors at the cell surface has been described and the ester of potential regulators of TGF-β signaling continues to expand, little is known at the molecular level about the signaling mechanisms immediately downstream of the TGF-β receptors.

This lack of knowledge represents a serious deficiency in the art in view of the effects of cell regulatory factors such as TGF-β as described above. Therefore, further characterization of TGF-β signaling in vertebrates, particularly in mammals, and more particularly in humans is needed. A novel isolated and purified polypeptide having a role in the modulation of TGF-β signaling would have broad utility due to the various and multiple physiological and pathophysiological roles of TGF-β, as described above.

SUMMARY OF THE INVENTION

The present invention contemplates an isolated and purified vertebrate serine-threonine kinase receptors associated protein (STRAP) which plays a role in the modulation of TGF-β biological activity. More preferably, a polypeptide of the invention is a recombinant polypeptide. Even more preferably, a polypeptide of the present invention comprises a mammalian STRAP. Even more preferably, a polypeptide, of the present invention comprises a human STRAP. Even more preferably, a polypeptide of the present invention comprises the amino acid residue sequence of SEQ ID NO:2.

The present invention also provides an isolated and purified polynucleotide that encodes a polypeptide that plays a role in the modulation of TGF-β biological activity. In a preferred embodiment, a polynucleotide of the present invention comprises a DNA molecule from a vertebrate species. A preferred vertebrate is a mammal. A preferred mammal is a human. More preferably, a polynucleotide of the present invention encodes a polypeptide designated STRAP. Even more preferred, a polynucleotide of the present invention encodes a polypeptide comprising the amino acid residue sequence of SEQ ID NO:2. Most preferably, an isolated and purified polynucleotide of the invention comprises the nucleotide base sequence of SEQ ID NO:1.

In another embodiment, the present invention provides an antibody immunoreactive with a STRAP polypeptide as described above. SEQ ID NO:1 and SEQ ID NO:2 set forth representative vertebrate nucleotide and amino acid sequences. Also contemplated by the present invention are antibodies immunoreactive with homologues or biologically equivalent STRAP polynucleotide and potypeptides found in other vertebrates. Preferably, an antibody of the invention is a monoclonal antibody. More preferably, the STRAP polypeptide comprises human STRAP. Even more preferably, the STRAP polypeptide comprises the amino acid residue sequence of SEQ ID NO:2.

In another aspect, the present invention contemplates a method of producing an antibody immunoreactive with STRAP as described above, the method comprising the steps of (a) transfecting a recombinant host cell with a polynucleotide that encodes a STRAP polypeptide having a TGF-β activity-modulating function; (b) culturing the host cell under conditions sufficient for expression of the polypeptide; (c) purifying the polypeptide; and (d) raising the antibody to the polypeptide. Preferably, the host cell is transfected with the polynucleotide of SEQ ID NO:1. Even more preferably, the present invention provides an antibody prepared according to the method described above. Also contemplated by the present invention is the use of homologues or biologically equivalent polynucleotides and polypeptides found in other vertebrates to produce antibodies.

Alternatively, the present invention provides a method of detecting a STRAP polypeptide as described above, wherein the method comprises immunoreacting the polypeptide with an antibody prepared according to the method described above to form an antibody-polypeptide conjugate, and detecting the conjugate.

In yet another embodiment, the present invention contemplates a method of detecting a messenger RNA transcript that encodes a STRAP polypeptide as described above, wherein the method comprises hybridizing the messenger RNA transcript with a polynucleotide sequence that encodes that polypeptide to form a duplex; and detecting the duplex. Alternatively, the present invention provides a method of detecting a DNA molecule that encodes a STRAP polypeptide as described above, wherein the method comprises hybridizing DNA molecules with a polynucleotide that encodes a STRAP polypeptide having a TGF-β activity-modulating function to form a duplex; and detecting the duplex.

In another aspect, the present invention contemplates an assay kit for detecting the presence of a STRAP polypeptide in a biological sample, where the kit comprises a first container containing a first antibody capable of immunoreacting with a vertebrate STRAP polypeptide having a TGF-β activity-modulating function, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support More preferably still, the first and second antibodies comprise an indicator, and, preferably, the indicator is a radioactive label or an enzyme.

In an alternative aspect, the present invention provides an assay kit for detecting the presence, in biological samples, of a STRAP polypeptide, the kits comprising a first container that contains a second polynucleotide identical or complementary to a segment of at least 10 contiguous nucleotide bases of a polynucleotide that encodes a STRAP polypeptide having a TGF-β activity-modulating function.

In another embodiment, the present invention contemplates an assay kit for detecting the presence, in a biological sample, of an antibody immunoreactive with a STRAP polypeptide, the kit comprising a first container containing a STRAP polypeptide having a TGF-β activity-modulating function that immunoreacts with the antibody, with the polypeptide present in an amount sufficient to perform at least one assay.

In still a further embodiment, this invention pertains to therapeutic methods based upon the TGF-β activity-modulating function of STRAP as described herein.

Thus, an aspect of the present invention pertains to the discovery of the novel STRAP protein and nucleic acid encoding the STRAP protein. Preferred nucleic acid and amino acid sequences for STRAP are described in SEQ ID NO:1 and SEQ ID NO:2.

It is another aspect of this invention that the novel STRAP protein acts in the TGF-β cascade to modulate TGF-β biological activity.

It is thus another aspect of this invention to provide a purified and isolated STRAP polypeptide having a TGF-β activity-modulating function.

The foregoing aspects and embodiments have broad utility given the biological significance of the TGF-β cascade, as is known in the art. By way of example, the foregoing aspects and embodiments are useful in the preparation of screening assays and assay kits that are used to identify compounds that affect or modulate TGF-β biological activity, or that are used to detect the presence of the proteins and nucleic acids of this invention in biological samples. Additionally, it is well known that isolated and purified polypeptides have utility as feed additives for livestock and further polynucleotides encoding the polypeptides are thus useful in producing the polypeptides.

Some of the aspects and objects of the invention having been stated hereinabove, other aspects and objects will become evident as the description proceeds, when taken in connection with the accompanying Drawings and Examples as best described hereinbelow.

BRIEF DESCRIPTION OF THE DRAWINGS

FIG. 2A displays the amino acid sequence deduced from the nucleotide sequence of the full-length mouse STRAP cDNA is shown in single letter code. The WD domains are underlined with solid lines and the C-terminal end of the deletion mutant, STRAP (1-294)-Flag is indicated.

FIG. 2B displays the alignment of the amino acid sequences of STRAP and TRIP-1. The alignment was performed using a software program sold under the trademark MEGALIGN™ by DNASTAR Inc. of Madison, Wis. Identical amino acids are shown in white letters on a black background. Dashes represent gaps for optimal alignment.

DETAILED DESCRIPTION OF THE INVENTION

Figure 1:
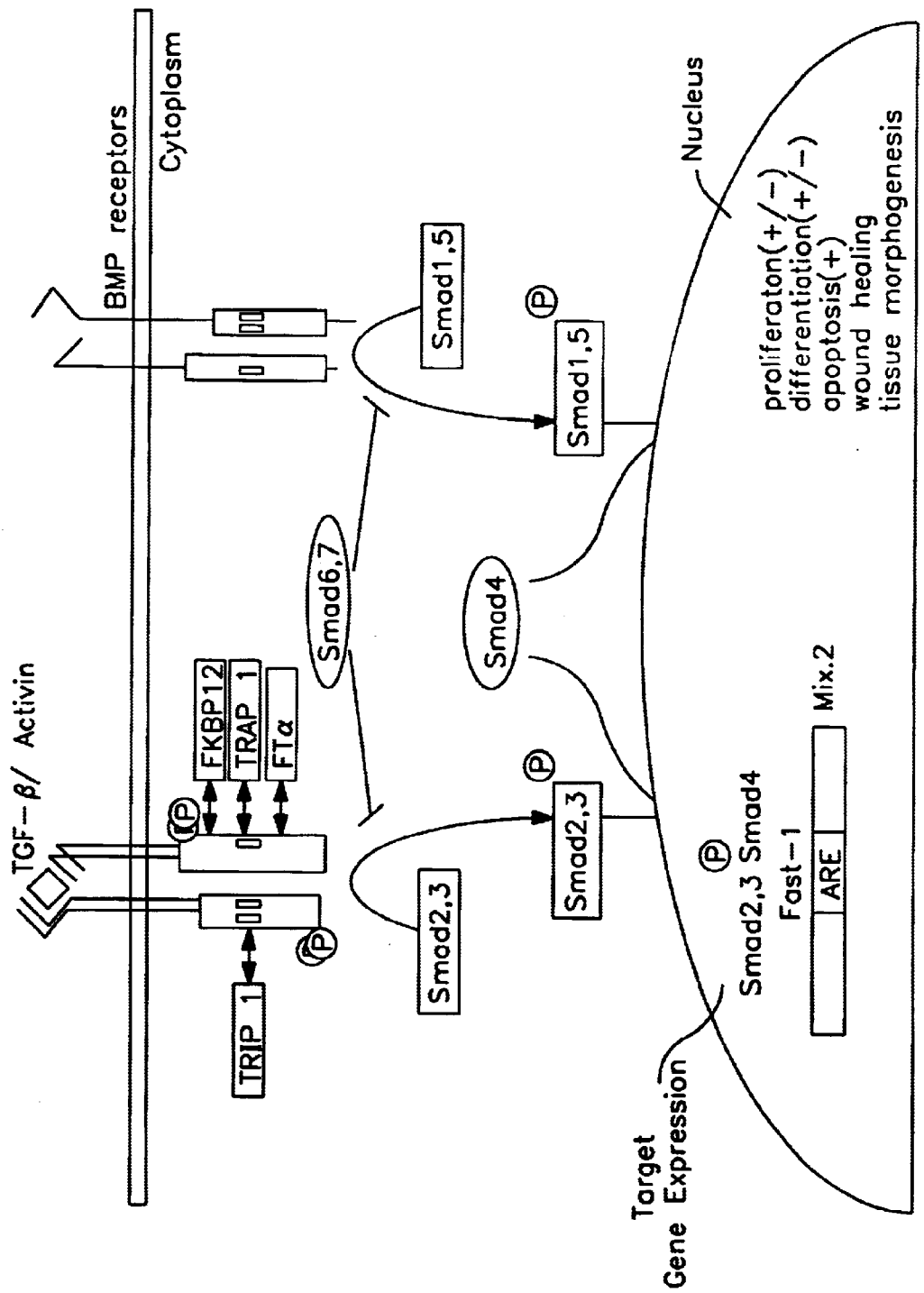
FIG. 1 is a schematic of the TGF-β cascade, which spans the cell membrane, cytoplasm and nucleus. Biological responses mediated by the cascade include proliferation (+/−), differentiation (+/−), apoptosis (+), wound healing and tissue morphogenesis. In addition to TGF-β or TGF-β/Activin, other depicted participants in the cascade include TRIP-1, FKBP12. TRAP1, FTα, Smads 1,2,3,4,5,6 and 7 and BMP receptors, along with Fast-$_1$, Mix.2 and ARE. P=phosphate group, i.e. a phosphorylated species.

SMAD proteins play a key role in intracellular signaling by TGF-β superfamily members that regulate cell proliferation, differentiation, apoptosis, and development See Massagué et al. *Trends Cell Biol.* 7:187–192 (1997); Roberts, A. B. & Sporn, M. B. in *Peptide Growth Factors and their Receptors Part* I (eds. Sporn, M. B. & Roberts, A. B.) 419–472 (Springer, Heidelberg, 1990); and Heldin et al.

*Nature* 390:465–471 (1997). TGF-β family members initiate signaling from the cell surface by binding to a heteromeric complex of two distinct but related serine-threonine kinase receptors. Heldin et al. *Nature* 390:465–471 (1997). The identification of a novel, WD-domain containing protein, designated STRAP, which specifically associates with both type I and type II TGF-β receptors in vivo, is disclosed hereinbelow.

STRAP associates stably with inhibitory SMADs, including Smad6 (Smad6 described in described in imamura et al. *Nature* 389:622–626 (1997)), and Smad7 (Smad7 described in Nakao et al., *Nature* 389:631–635 (1997) and Hayashi et al., *Cell* 89:1165–1173 (1997)). But, STRAP does not interact with Smad1 (Smad1 described in Hoodless et al., *Cell* 85:489–500 (1906); Kretzschmar et al., *Genes Dev.* 11:984–995 (1997)).

The C-terminus of STRAP is required for its phosphorylation mediated by the TGF-β receptors and for its association with other phosphoproteins. Overexpression of STRAP leads to inhibition of TGF-β mediated transcriptional activation. The existence of the STRAP gene from yeast to mammals suggests an evolutionarily conserved function in eukaryotes. These results suggest a functional role for STRAP in TGF-β signaling and STRAP mediated negative regulation of TGF-β signaling involves recruitment of inhibitory SMADs to the receptor complex.

The therapeutic and screening methods in accordance with the present invention are illuminated by a review of recognized TGF-β-mediated biological activities. Although TGF-β was originally described as a factor that induced a transformed phenotype in rodent fibroblasts, it is now clear that TGF-β does not primarily cause oncogenic transformation. Instead, TGF-β mediates or regulates a remarkable range of biological activities including cell growth, differentiation, gene expression, wound healing and tissue morphogenesis. In addition, alternation of normal TGF-β function has been causally associated with pathogenesis of several diseases, including diabetic nephropathy, atherosclerosis and cancer.

TGF-β has a multifunctional role in tumorigenesis. At early stages, when cells still respond to its antimitogenic effects, TGF-β may act as a tumor-suppressor. However, during malignant progression, when cells acquire an insensitivity to growth inhibition by TGF-β, it may function as a tumor promoter by stimulation of angiogenesis, immunosuppression and synthesis of extracellular matrix, which provides an appropriate micenvironment for rapid tumor growth and metastasis.

The escape from the anti-mitogenic response of cells by TGF-β during tumor progression suggests a function for components in the TGF-β signal transduction pathway as tumor suppressors. Disruption of the normal signaling pathways could therefore predispose to, or cause, cancer. Support for a tumor-suppressor role for the type II receptor of TGF-β came from the analysis that it is inactivated by mutation in gastrointestinal cancers with microsatellite instability. Missense mutations elsewhere in TβR-II have been described in a human T-cell lymphoma and in head and neck carcinomas.

Disruption of the TGF-β pathway in cancer is demonstrated additionally by the identification of inactivating mutations in the signaling components Smad4 and Smad2. Smad4 was originally cloned as a tumor suppressor gene on chromosome 18q21 that is deleted or mutated in half of human pancreatic carcinomas. Smad4 mutations also have been found in carcinomas of the colon, breast, ovary, lung, and head and neck. Smad2 is also located at 18q21 and it too is the target of missense and other mutations in colon cancer.

In view of the recognized biological activities of TGF-β, the utility of the therapeutic and screening methods of the present invention, which involve the functional role for purified and isolated STRAP in TGF-β signaling and STRAP-mediated negative regulation of TGF-β signaling as described herein, is readily apparent to one of skill in the art.

A. Definitions and Techniques Affecting Polypeptide and Polynucleotides

The present invention concerns DNA segments, isolatable from eukaryotic cells, preferably cells from vertebrate tissue, more preferably from mammalian tissue, and even more preferably from human tissue, which are free from genomic DNA and which are capable of conferring TGF-β activity-modulating function in a recombinant host cell when incorporated into the recombinant host cell. As used herein, the term "mammalian tissue" refers to, among others, normal mammalian smooth muscle tissues, as exemplified by, but not limited to, human smooth muscle tissues and to abnormal mammalian tissues, as exemplified by, but not limited to, tumor tissues. DNA segments capable of conferring TGF-β activity-modulating function may encode compete STRAP polypeptides, cleavage products and biologically actively functional domains thereof.

The terms "STRAP polypeptide", "STRAP gone product", and "STRAP", as used in the specification and in the claims refer to proteins having amino acid sequences which are substantially identical to the respective native STRAP amino acid sequences and which are biologically active in that they are capable of playing a role in the TGF-β cascade or are capable of cross-reacting with an anti-STRAP antibody raised against STRAP. Such sequences are disclosed herein. The terms "STRAP polypeptide", "STRAP gene product", and "STRAP" also include analogs of STRAP molecules which exhibit at least some biological activity in common with native STRAP. Furthermore, those skilled in the art of mutagenesis will appreciate that other analogs, as yet undisclosed or undiscovered, may be used to construct STRAP analogs. There is no need for a "STRAP polypeptide" or a "STRAP" to comprise all, or substantially all, of the amino acid sequence of the native STRAP genes. Shorter or longer sequences are anticipated to be of use in the invention.

The terms "STRAP gene", "STRAP gene sequence" and "STRAP gene segment" refer to any DNA sequence that is substantially identical to a DNA sequence encoding a STRAP polypeptide or STRAP as defined above. The terms also refer to RNA, or antisense sequences, compatible with such DNA sequences. A "STRAP gene", "STRAP gene sequence" and "STRAP gene segment" may also comprise any combination of associated control sequences.

The term "substantially identical", when used to define either a STRAP or STRAP amino acid sequence, or a STRAP gene or STRAP nucleic acid sequence, means that a particular sequence, for example, a mutant sequence, varies from the sequence of a natural STRAP by one or more deletions, substitutions, or additions, the net effect of which is to retain at least some of biological activity of STRAP. Alternatively, DNA analog sequences are "substantially identical" to specific DNA sequences disclosed herein if: (a) the DNA analog sequence is derived from coding regions of the natural STRAP or STRAP gene; or (b) the DNA analog sequence is capable of hybridization of DNA sequences of (a) under moderately stringent conditions and which encode biologically active STRAP or STRAP gene; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

A.1. Percent Similarity

Percent similarity may be determined, for example, by comparing sequence information using the GAP computer program, available from the University of Wisconsin Geneticist Computer Group. The GAP program utilizes the alignment method of Needleman et al. 1970, as revised by Smith et al. 1981. Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identifies and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

A.2. Nucleic Acid Sequences

In certain embodiments, the invention concerns the use of STRAP genes and gene products that include within their respective sequences a sequence which is essentially that of the STRAP gene, or the corresponding protein. The term "a sequence essentially as that of STRAP or STRAP gene", means that the sequence substantially corresponds to a portion of a STRAP or STRAP gene and has relatively few bases or amino acids (whether DNA or protein) which are not identical to those of a STRAP or STRAP gene, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a STRAP or STRAP gene, will be sequences which are "essentially the same".

STRAP and STRAP genes which have functionally equivalent codons are also covered by the invention. The term "functionally equivalent codon" is used herein to refer to codons that encode the same amino acid, such as the six codons for arginine or serine, and also to refer to codons that encode biologically equivalent amino acids (see Table 1). Thus, when referring to the sequence examples presented in SEQ ID NOs:1–2, the substitution of functionally equivalent codons of Table 1 into the sequence examples of SEQ ID NOs:1–2 is envisioned. Thus, applicants are in possession of amino acid and nucleic acids sequences which include such substitutions but which are not set forth herein in their entirety for convenience.

TABLE 1

Functionally Equivalent Codons.

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See, e.g., Wetmur & Davidson, 1968). Determining appropriate hybridization conditions to identify and/or isolate sequences containing high levels of homology is well known in the art. (See e.g., Sambrook et al., 1989). For the purposes of specifying conditions of high stringency, preferred conditions are salt concentration of about 200 mM and temperature of about 45° C.

Probe sequences may also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a STRAP refers to a DNA segment which contains STRAP coding sequences, yet is isolated away from, or purified free from, total genomic DNA of Homo sapiens. Included within the term "DNA segment" are DNA segments and smaller fragments of such segments, and also recombinant vectors, including, for example, plasmids, cosmids, phages, viruses, and the like.

Similarty, a DNA segment comprising an isolated or purified STRAP gene refers to a DNA segment including STRAP coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the STRAP gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the. segment by the hand of man.

In particular embodiments, the invention concerns isolated DNA segments and recombinant vectors incorporating DNA sequences which encode a STRAP that includes within its amino acid sequence the amino add sequence of SEQ ID NO:2. In other particular embodiments, the invention concerns isolated DNA segments and recombinant vectors incorporating DNA sequences which encode a protein that includes within its amino acid sequence the amino acid sequence of STRAP corresponding to human tissues.

It will also be understood that this invention is not limited to the particular nucleic acid and amino acid sequences of SEQ ID NOS:1 and 2. Recombinant vectors and isolated DNA segments may therefore variously include the STRAP-encoding region itself, include coding regions bearing selected alterations or modifications in the basic coding region, or include encoded larger polypeptides which nevertheless include STRAP-encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in SEQ ID NO:2. Naturally, where the DNA segment or vector encodes a full length STRAP gene product, the most preferred sequence is that which is essentially as set forth in SEQ ID NO:1 and which encode a protein that exhibits TGF-β modulating activity in for example mammalian epithelial cells, as may be determined by, for example, β-galactosidase activity assays, as disclosed herein.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of SEQ ID NO:2, will be sequences which are "essentially as set forth in SEQ ID NO:2".

In particular embodiments, the invention concerns gene therapy methods that use isolated DNA segments and recombinant vectors incorporating DNA sequences which encode a protein that includes within its amino acid sequence an amino acid sequence in accordance with SEQ ID NO:2, SEQ ID NO:2 being derived from mammalian tissue. In other particular embodiments, the invention concerns isolated DNA sequences and recombinant DNA vectors incorporating DNA sequences which encode a protein that includes within its amino acid sequence the amino acid sequence of the STRAP protein from human tissue.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1, respectively, and has relatively few codons which are not identical, or functionally equivalent, to the codons of SEQ ID NO:1, respectively. Again, DNA segments which encode gene products exhibiting TGF-β modulating activity of the STRAP gene product will be most preferred. The term "functionally equivalent codon" is used herein to refer to codons that encode the same amino acid, such as the six codons for arginine or serine, and also to refer to codons that encode biologically equivalent amino acids (see Table 1).

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent STRAP proteins and peptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged, e.g. substitution of Ile for Leu at amino acid 20, at amino acid 116, at amino acid 231, and/or at amino acid 307 for STRAP as set forth in SEQ ID NOs:1–2. Changes designed by man may be introduced through the application of site-directed mutagenesis techniques, e.g., to introduce improvements to the antigenicity of the protein or to test STRAP mutants in order to examine TGF-β modulating activity at the molecular level.

If desired, one may also prepare fusion proteins and peptides, e.g., where the STRAP coding region is aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the STRAP gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a STRAP gene in its natural environment. Such promoters may include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, specifically incorporated herein by reference. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccina virus promoter and the baculovirus promoter, which are more fully described below.

In an alternative embodiment, the present invention provides an expression vector comprising a polynucleotide that encodes a vertebrate STRAP polypeptide having TGF-β modulating activity. Also preferably, an expression vector of the present invention comprises a polynucleotide that encodes human STRAP. More preferably, an expression vector of the present invention comprises a polynucleotide that encodes a polypeptide comprising the amino acid residue sequence of SEQ ID NO:2. More preferably, an expression vector of the present invention comprises a polynucleotide comprising the nucleotide base sequence of SEQ ID NO:1. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a STRAP polypeptide having TGF-β modulating activity. SEQ ID NO:1 and SEQ ID NO: 2 set forth representative vertebrate nucleotide and amino acid sequences. Also contemplated by the present invention are homologous or biologically equivalent polynucleotides and STRAP polypeptides found in other vertebrates. Preferably, a recombinant host cell of the present invention is transfected with the polynucleotide that encodes human STRAP. More preferably, a recombinant host cell of the present invention is transfected with the polynucleotide sequence of SEQ ID NO:1. Even more preferably, a host cell of the invention is a eukaryotic host cell. Still more preferably, a recombinant host cell of the present invention is a vertebrate cell. Preferably, a recombinant host cell of the invention is a mammalian cell.

In another aspect, a recombinant host cell of the present invention is a prokaryotic host cell. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of the STRAP polypeptide in a manner to enable all necessary transcriptional and post-transcriptional modification.

In yet another embodiment, the present invention contemplates a method of preparing a STRAP polypeptide comprising transfecting a cell with polynucleotide that encodes a STRAP polypeptide having TGF-β modulating activity to produce a transformed host cell; and maintaining the transformed host call under biological conditions sufficient for expression of the polypeptide. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of SEQ ID NO:1. SEQ ID NO:1 and SEQ ID NO:2 set forth nucleotide and amino acid sequences for a representative vertebrate, mouse. Also contemplated by the present invention are homologues or biologically equivalent STRAP polynucleotides and polypeptides found in other vertebrates.

As mentioned above, in connection with expression embodiments to prepare recombinant STRAP proteins and peptides, it is contemplated that longer DNA segments will most often be used, with DNA segments encoding the entire STRAP protein, functional domains or cleavage products thereof, being most preferred. However, it will be appreciated that the use of shorter DNA segments to direct the expression of STRAP peptides or epitopic core regions, such as may be used to generate anti-STRAP antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins preferably have a coding length on the order of about 1,053 nucleotides for a protein in accordance with SEQ ID NO:2.

Naturally, the present invention also encompasses DNA segments which are complementary, or essentially complementary, to the sequence set forth in SEQ ID NO:1. The terms "complementary" and "essentially complementary" are defined above. Excepting intronic or flanking regions, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides of SEQ ID NO:1, will be sequences which are "essentially as set forth in SEQ ID NO:1". Sequences which are essentially the same as those set forth in SEQ ID NO:1 may also be functionally defined as sequences which are capable of hybridizing to a nucleic acid segment containing the complement of SEQ ID NO:1 under relatively stringent conditions. Suitable relatively stringent hybridization conditions are described herein and will be well known to those of skill in the art.

A.3. Biologically Functional Equivalents

As mentioned above, modification and changes may be made in the structure of the STRAP proteins and peptides described herein and still obtain a molecule having like or otherwise desirable characteristics. For example, certain amino acids may be substituted for other amino acids in a protein structure without appreciable loss of interactive capacity with proteins such as, for example, inhibitory SMADs or TGF-β receptors in the TGF-β cascade. Since it is the interactive capacity and nature of a protein that defines that protein's biological activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the STRAP proteins and peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain. not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where if any changes, for example, in the C-terminus of STRAP which required for its phosphorylation mediated by the TGF-β receptors and for its association with other phosphoproteins, could result in a loss of an aspect of the utility of Fe resulting peptide for the present invention.

Amino acid substitutions, such as those which might be employed in modifying the STRAP proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteinelcystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropatic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicty of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

A.4. Seguence Modification Techniques

Modifications to the STRAP proteins and peptides described herein may be carried out using techniques such as site directed mutagenesis. Site-specific mutagenesis is a technique useful in the preparation of individual peptides, or biologically functional equivalent proteins or peptides, through specific mutagenesis of the underlying DNA The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes, for example, the STRAP gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful STRAP or other TGF-β biological activity-modulating species and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

A.5. Other Structural Equivalents

In addition to the STRAP peptidyl compounds described herein, the inventors also contemplate that other sterically similar compounds may be formulated to mimic the key portions of the peptide structure. Such compounds may be used in the same manner as the paptides of the invention and hence are also functional equivalents. The generation of a structural functional equivalent may be achieved by the techniques of modeling and chemical design known to those of skill in the art. It will be understood that all such sterically similar constructs fall within the scope of the present invention.

B. Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

B.1. Preparation of Vectors

In vectors, it is understood that the DNA coding sequences to be expressed, in this case those encoding the STRAP gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., the STRAP promoter for STRAP) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose, transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from tat site.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, the STRAP gene, it is proposed that one will desire to preferably employ a vector construct that will deliver the desired gene to the affected cells. This will, of course, generally require that the construct be delivered to the targeted cells, for example, mammalian smooth muscle cells. It is proposed that this may be achieved most preferably by introduction of the desired gene through the use of a viral vector to carry the STRAP sequence to efficiently infect the cells. These vectors will preferably be an adenoviral, a retroviral, a vaccinia viral vector or adeno-associated virus. These vectors are preferred because they have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient Where the STRAP gene itself is employed it will be most convenient to simply use the wild type STRAP gene directly. However, it is contemplated that certain regions of the STRAP gene may be employed exclusively without employing the entire wild type STRAP gene. It is proposed that it will ultimately be preferable to employ the smallest region needed to modulate TGF-β activity so that one is not introducing unnecessary DNA into cells which receive either a STRAP gene construct Techniques well known to those of skill in the art, such as the use of restriction enzymes, will allow for the generation of small regions of the STRAP gene. The ability of these regions to modulate TGF-β activity can easily be determined by the assays reported in the Examples. In general, techniques for assessing the modulation of TGF-β activity are well known in the art.

B.2. Transgenic Animals

It is also contemplated to be within the scope of the present invention to prepare a transgenic non-human animal which expresses the STRAP gene of the present invention. Preferably, the preparation of a transgenic animal which overexpresses STRAP to establish a TGF-β deficiency-like disorder in the animal is contemplated to be within the scope of the present invention. A preferred transgenic animal is a mouse.

The term "transgene" refers to exogenous genetic material which does not naturally form part of the genetic material of an animal to be genetically altered but can be incorporated into the germ and/or somatic cells of that animal by standard transgenic techniques. The term "heterologous DNA" refers to DNA which has been transferred from one individual animal, species or breed to a different individual animal, species or breed. The term "transgenic" refers to cells, tissues, embryos, fetuses or animals which carry one or more transgenes. The term "chimeric" refers to an embryo, fetus or animal which consists of two or more tissues of different genetic composition.

Techniques for the preparation of transgenic animals are known in the art. Representative techniques are described in U.S. Pat. No. 5,489,742 (transgenic rat); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

With respect to a representative method for the preparation of a transgenic mouse, cloned recombinant or synthetic DNA sequences or DNA segments encoding STRAP are injected into fertilized mouse eggs. The injected eggs are implanted in pseudo pregnant females and are grown to term to provide transgenic mice whose cells express STRAP. The injected sequences are constructed having promoter sequences connected so as to express the desired protein in multiple tissues of the transgenic mouse.

The genetically modified animals could express transgenes of commercial interest, including those having therapeutic or prophylactic value to the animal itself or to its offspring. Alternatively, the genetically modified animals can be employed in the production of therapeutic agents. For example, genetically modified avian species that can lay eggs containing drugs, proteins and antibodies to ward off illness that have been produced via the insertion the genes that make the proteins into viral and other vectors to get them into the birds. STRAP gene products can also be produced and isolated in this manner.

C. Generation of Antibodies

In still another embodiment, the present invention provides an antibody immunoreactive with a polypeptide of the present invention. Preferably, an antibody of the invention is a monoclonal antibody. Techniques for preparing and characterizing antibodies are well known in the art (See, e.g., *Antibodies A Laboratory Manual*, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Representative and preferred carriers are keyhole limpet hemocyanin (KLH) and bovine serum albumin (BSA). Other albumins such as ovalbumin, mouse serum albumin or rabbit serum albumin can also be used as carriers.

Techniques for conjugating a polypeptide or a polynucleotide to a carrier protein are well known in the art and include glutaraldehyde, m-maleimidobenzoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Representative and preferred adjuvants include complete Freund's adjuvant, incomplete Freund's adjuvants and aluminum hydroxide adjuvant.

The amount of immunogen used for the production of polyclonal antibodies varies, inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a method of producing an antibody immunoreactive with a STRAP polypeptide, the method comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the STRAP polypeptide is capable of modulating TGF-β activity. Even more preferably, the present invention provides antibodies prepared according to the method described above.

A monoclonal antibody of the present invention can be readily prepared through use of well-known techniques such as those exemplified in U.S. Pat No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Representative and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in micromer plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed Mycobacterium tuberculosis). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells am tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immuno-specific reaction with the bound antibody. The polypeptide or polynucleotide is then easily removed from the substrate and purified.

D. Detecting a Polynucleotide or a Polypeptide of the Present Invention

Alternatively, the present invention provides a method of detecting a polypeptide of the present invention, wherein the method comprises immunoreacting the polypeptides with antibodies prepared according to the method described above to form antibody-polypeptide conjugates, and detecting the conjugates.

In yet another embodiment, the present invention contemplates a method of detecting messenger RNA transcripts that encode a polypeptide of the present invention, wherein the method comprises hybridizing the messenger RNA transcripts with polynucleotide sequences that encode the polypeptide to form duplexes, and detecting the duplex. Alternatively, the present invention provides a method of detecting DNA molecules that encode a polypeptide of the present invention, wherein the method comprises hybridizing DNA molecules with a polynucleotide that encodes that polypeptide to form duplexes; and detecting the duplexes.

D.1. Screening Assays for a Polypeptide of the Present Invention

The present invention provides a method of screening a biological sample for the presence of a STRAP polypeptide. Preferably, the STRAP polypeptide modulates the biological activity of TGF-β. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay method, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microliter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary inter alia with the biological conditions used, the concentration of antibody and polypeptide and the nature of the sample (e.g., fluid or tissue sample). Techniques for determining exposure time are well known to one of ordinary skill in the art Typically, where the sample is fluid and the concentration of polypeptide in that sample is about $10^{-10}$M, exposure time is from about 10 minutes to about 200 minutes.

The presence of polypeptide in the sample is detected by detecting the formation and presence of antibody-polypeptide conjugates. Techniques for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Representative and well known such indicators include radioactive labels (e.g., $^{32}P$, $^{251}I$, $^{14}C$), a second antibody or an enzyme such as horse radish peroxidase. Techniques for affixing indicators to antibodies are well known in the art. Commercial kits are available.

D.2. Screening Assay for Anti-Polypeptide Antibody

In another aspect, the present invention provides a method of screening a biological sample for the presence of antibodies immunoreactive with a STRAP polypeptide. Preferably the STRAP polypeptide modulates the biological activity of TGF-β. In accordance with such a method, a biological sample is exposed to a STRAP polypeptide under biological conditions and for a period of time sufficient for antibody-polypeptide conjugate formation and the formed conjugates are detected.

D.3. Screening Assay for Polynucleotide that Encodes a STRAP Polypeptide of the Present Invention A DNA molecule and, particularly a probe molecule, can be used for hybridizing as an oligonucleotide probe to a DNA source suspected of encoding a STRAP polypeptide of the present invention. Preferably the STRAP polypeptide modulates the biological activity of TGF-β. The probing is usually accomplished by hybridizing the oligonucleotide to a DNA source suspected of possessing a STRAP gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization method of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) reagents for detecting and isolating other members of the polypeptide family and related polypeptides from a DNA library potentially containing such sequences; (3) primers for hybridizing to related sequences for the purpose of amplifying those sequences; (4) primers for altering native STRAP DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected STRAP gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as that shown in SEQ ID NO:1. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical techniques, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate reagent, such as a label, for determining hybridization. A wide variety of appropriate indicator reagents are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by the label.

D.4. Assay Kits

In another aspect, the present invention contemplates diagnostic assay kits for detecting the presence of a polypeptide of the present invention in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support More preferably still, the first and second antibodies comprise an indicator, and, preferably, the indicator is a radioactive label or an enzyme.

The present invention also contemplates an kit for screening agents. Such a kit can contain a polypeptide of the present invention. The kit can contain reagents for detecting an interaction between an agent and a receptor of the present invention. The provided reagent can be radiolabeled. The kit can contain a known radiolabelled agent capable of binding or interacting with a receptor of the present invention.

In an alternative aspect, the present invention provides diagnostic assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, SEQ ID NO:1.

In another embodiment, the present invention contemplates diagnostic assay kits for detecting the presence, in a biological sample, of antibodies immunoreactive with a polypeptide of the present invention, the kits comprising a first container containing a STRAP polypeptide, that immunoreacts with the antibodies, with the polypeptide present in an amount sufficient to perform at least one assay. Preferably, the STRAP polypeptide modulates the biological activity of TGF-β. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support the solid support can be chromatograph media or a microscope slide. When the reagent provided is a dry powder, the powder can be reconstituted by the addition of a suitable solvent. The solvent can be provided.

E. Screening Assays

In yet another aspect, the present invention contemplates a method of screening substances for their ability to affect or modulate the biological activity of STRAP. Preferably, the present invention contemplates a method of screening substances for their ability to affect or modulate the biological activity of STRAP to thereby affect or modulate the biological activity of TGF-β. Utilizing the methods and compositions of the present invention, screening assays for the testing of candidate substances can be derived. A candidate substance is a substance which potentially can promote or inhibit the biological activity of STRAP to thereby affect or modulate the biological activity of TGF-β, by binding or other intramolecular interaction, with STRAP.

The biological activity of TGF-β can be beneficial (e.g. as tumor suppressor and/or factor in wound healing) or detrimental (e.g. as a tumor promoter or promoter of undesired extracellular matrix production). Thus, a candidate substance identified according to the screening assay described herein is contemplated to have the ability to modulate STRAP biological activity and to thereby modulate the biological activity of TGF-β, and thus have utility in the treatment of disorders associated with the biological activity of TGF-β.

A representative method of screening candidate substances for their ability to modulate STRAP biological activity and to thereby modulate the biological activity of TGF-β comprises the steps of (a) establishing replicate test and control samples that comprise TGF-β and a STRAP polypeptide capable modulating the biological activity of TGF-β; (b) administering a candidate substance to test sample but not the control sample; (c) measuring the biological activity of TGF-β in the test and the control samples; and (d) determining that the candidate substance modulates STRAP biological activity to thereby modulate the biological activity of TGF-β if the biological activity of TGF-β measured for the test sample is greater or less than the biological activity of TGF-β level measured for the control sample. The replicate test and control samples can further comprise a cell that expresses a STRAP polypeptide capable of modulating the biological activity of TGF-β. The present invention also contemplates a recombinant cell line suitable for use in the representative method.

Thus, a screening assay of the present invention generally involves determining the ability of a candidate substance to modulate STRAP biological activity and thereby modulate the biological activity of TGF-β in a target cell, such as the screening of candidate substances to identify those that modulate, i.e. inhibit or promote, STRAP biological activity and thereby modulate the biological activity of TGF-β. Target cells can be either naturally occurring cells known to contain a polypeptide of the present invention or transformed cell produced in accordance with a method of transformation set forth hereinbefore.

As is well known in the art, a screening assay provides a cell under conditions suitable for testing the modulation of STRAP biological activity and thereby, the modulation of the biological activity of TGF-β. These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as glycosylation or prenylation. It is contemplated that a polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably about 200 milliosmois per liter to about 400 mosm/l and, even more preferably from about 290 mosm/L to about 310 mosm/L. The presence of factors can be required for the proper testing of STRAP and TGF-β modulation in specific cells. Such factors include, for example, the presence and absence (withdrawal) of growth factor, interleukins, or colony stimulating factors. U.S. Pat. No. 5,645,999 also describes representative screening assays, and the entire contents of U.S. Pat. No. 5,645,999 are herein incorporated by reference.

In one embodiment, a screening assay is designed to be capable of discriminating candidate substances having selective ability to interact with one or more of the polypeptides of the present invention but which polypeptides are without a substantially overlapping activity with another of those polypeptides identified herein. Representative assays including genetic screening assays and molecular biology screens such as a yeast two-hybrid screen which will effectively identify STRAP-interacting genes important for TGF-β modulation or other STRAP-mediated biological activity. One version of the yeast two-hybrid system has been described (Chien et al., 1991, *Proc. Netl. Acad. Sci. USA*, 88:9578–9582) and is commercially available from Clontech (Palo Alto, Calif.). Representative yeast two-hybrid screens are also described in the Examples.

F. Therapeutic Methods

TGF-β binds to cell surface receptors possessed by essentially all types of cells, causing profound changes in them. In some cells, TGF-β promotes cell proliferation, in others it suppresses proliferation. A marked effect of TGF-β is that it promotes the production of extracellular matrix proteins and their receptors by cells (for review s Keski-Oja et al., *J. Cell Biochem.* 33:95 (1987); Massague, *Cell* 49:437 (1987); Roberts and Sporn in "Peptides Growth Factors and Their Receptors", Springer-Verlag, Heidelberg (1989)).

While TGF-β has many essential cell regulatory functions, improper TGF-β activity can be detrimental to an organism. Since the growth of mesenchyme and proliferation of mesenchymal cells is stimulated by TGF-β, some tumor cells may use TGF-β as an autocrine growth factor. Therefore, if the growth factor activity of TGF-β could be prevented, tumor growth could be controlled. In other cases the inhibition of cell proliferation by TGF-β may be detrimental, in that it may prevent healing of injured tissues. The stimulation of extracellular matrix production by TGF-β is important in situations such as wound healing. However, in some cases the body takes this response too far and an excessive accumulation of extracellular matrix ensues. An example of excessive accumulation of extracellular matrix is glomerulonephritis, a disease with a detrimental involvement of TGF-β.

As used herein, the terms "TGF-β activity" and "TGF-β biological activity" are meant to be synonymous and are meant to refer to any biological activity of TGF-β. The biological activity can be accomplished by endogenous TGF-β or by TGF-β administered to a subject. Indeed, an isolated and purified TGF-β and/or recombinant TGF-β as well as TGF-β analog or peptidomimetic administered to a subject to impart TGF-β biological activity in the subject. In such case the imparted TGF-β biological activity comprises a TGF-β biological activity in accordance with the therapeutic methods of the present invention. Therapeutic compositions including TGF-β and TGF-β analogs are described in U.S. Pat. Nos. 4,686,283: 5,120,535; 5,436,288; 5,583,103; 5,693,607; 5,770,609; and 5,780,436, the contents of each of which are herein incorporated by reference.

The terms "TGF-β activity" and "TGF-β biological activity" are thus also meant to refer to activities mediated by the binding of TGF-β to its receptor to produce the art-recognized TGF-β cascade schematically presented in FIG. 1. This cascade includes SMAD interactions, as well as STRAP interactions with SMADs as described in the Examples below. Representative activities are described above and include, but are not limited to, the anti-mitogenic activity, extracellular matrix producing activity, wound healing, growth inhibition, and tumor suppressor and tumor promoter activities.

As used herein, the terms "STRAP activity" and "STRAP biological activity" are meant to be synonymous and are meant to refer to any biological activity of STRAP. The biological activity can be accomplished by endogenous STRAP or by STRAP administered to a subject. Indeed, an isolated and purified STRAP, recombinant STRAP, and/or STRAP analog or peptidomimetic, each prepared as described above, can be administered to a subject to impart STRAP biological activity in the subject. In such case the imparted STRAP biological activity comprises a STRAP biological activity in accordance with the therapeutic methods of the present invention.

The terms "STRAP activity" and "STRAP biological activity" are thus also meant to refer to activities mediated by the interactions of STRAP within the art-recognized TGF-β cascade schematically presented in FIG. 1 and as described below. Such interactions include STRAP interactions with SMADs as described in the Examples below. Representative activities include, but are not limited to, binding with SMADs and modulating TGF-β activity.

In view of the foregoing, a therapeutic method is contemplated according to the present invention. The therapeutic method comprises administering to a subject a substance that inhibits or promotes STRAP biological activity to thereby modulate the biological activity of TGF-β by inhibiting or promoting the activity of STRAP. Such a substance may be identified according to the screening assay set forth above. With respect to the therapeutic methods of the present invention, a preferred subject is a vertebrate subject. A preferred vertebrate is warm-blooded; a preferred warm-blooded vertebrate is a mammal. A preferred mammal is a mouse or, most preferably, a human. As used herein and in the claims, the term "patient" is contemplated to include both human and animal patients. Thus, veterinary therapeutic uses are contemplated in accordance with the present invention.

Contemplated is the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also contemplated is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine, ruminants, ungulates, horses, poultry, and the like.

Thus, the method may comprise treating a subject suffering from a disorder associated with TGF-β via modulating STRAP biological activity to thereby modulate the biological activity of TGF-β by administering to the patient an effective STRAP modulating amount of a substance identified according to the screening assay described above. By the term "modulating", it is contemplated that the substance can either promote or inhibit the activity of STRAP, depending on the disorder to be treated.

A therapeutic method according to the present invention may also comprise administering a therapeutic composition which comprises a biologically active STRAP of the present invention in amount effective to modulate the biological activity of TGF-β in the patient. Such a method is particularly contemplated when the inhibition of the biological activity of TGF-β in the patient is desired.

F.1. Modulators of STRAP

Insofar as a STRAP modulator can take the form of a STRAP ligand or ligand mimetic, and an anti-STRAP monoclonal antibody, or fragment thereof, it is to be appreciated that the potency, and therefore an expression of a "therapeutically effective" amount can vary. However, as shown by the present assay methods, one skilled in the art can readily assess the potency of a candidate STRAP modulator of this invention.

A STRAP modulator can be measured by a variety of means including through the use of a TGF-β responsive reporter, p3TP-Lux, which contains elements from the PAI-1 promoter, and drives expression of a luciferase reporter gene, as described herein; interaction of STRAP with TβRI, TβRII, SMADs, and/or other endogenous protein in the TGF-β cascade or monoclonal antibody to a STRAP as described herein; and the like assays.

A preferred STRAP modulator has the ability to substantially interact with STRAP in solution at modulator concentrations of less than one (1) micro molar ($\mu$M), preferably less than 0.1 $\mu$M, and more preferably less than 0.01 $\mu$M. By "substantially" is meant that at least a 50 percent reduction in STRAP biological activity is observed by modulation in the presence of the STRAP modulator, and at 50% reduction is referred to herein as an IC50 value.

A therapeutically effective amount of a STRAP modulator of this invention in the form of a monoclonal antibody, or fragment thereof, is typically an amount such that when administered in a physiologically tolerable composition is sufficient to achieve a plasma concentration of from about 0.01 microgram (ug) per milliliter (ml) to about 100 ug/ml, preferably from about 1 ug/ml to about 5 ug/ml, and usually about 5 ug/ml.

A therapeutically effective amount of a STRAP modulator of this invention in the form of a polypeptide is typically an amount of polypeptide such that when administered in a physiologically tolerable composition is sufficient to achieve a plasma concentration of from about 0.001 microgram (µg) per milliliter (ml) to about 10 µg/ml, preferably from about 0.05 µg/ml to about 1.0 ug/ml. Based on a polypeptide having a mass of about 38,523 grams per mole (i.e. 38,523 Da), the preferred plasma concentration in molarity is from about 0.013 micro molar (µM) to about 0.026 micro molar (µM).

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery methods are contemplated where there is a likelihood that the tissue targeted contains the target molecule. Thus, monoclonal antibodies or polypeptides of the invention can be administered intravenously, intraperitoneally, intramuscularly, subcutaneously, intra-cavity, transdermally, and can be delivered by peristaltic apparatus or technique.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subjects system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the mute of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

F.1.1. Polypeptides

In one embodiment, the invention contemplates STRAP modulators in the form of polypeptides. A polypeptide (peptide) STRAP modulator can have the sequence characteristics of either an endogenous ligand of the STRAP or the STRAP itself at the region involved in STRAP-ligand interaction. A preferred STRAP modulator peptide corresponds in sequence to an endogenous ligand of STRAP, such as TβRI, TβRII or a SMAD.

In one embodiment, a polypeptide of the present invention comprises no more than about 100 amino acid residues, preferably no more than about 60 residues, more preferably no more than about 30 residues. Peptides can be linear or cyclic.

It should be understood that a subject polypeptide need not be identical to the amino acid residue sequence of an endogenous ligand of STRAP, such as TβRI, TβRII or a SMAD, so long as it includes required binding sequences and is able to function as a STRAP modulator in an assay such as is described herein.

A subject polypeptide includes any analog, fragment or chemical derivative of a polypeptide which is a STRAP modulator. Such a polypeptide can be subject to various changes, substitutions, insertions, and deletions where such changes provide for certain advantages in its use. In this regard, a STRAP modulator polypeptide of this invention corresponds to, rather than is identical to, the sequence of the endogenous ligand where one or more changes are made and it retains the ability to function as a STRAP modulator in one or more of the assays as defined herein. Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to a sequence of an endogenous ligand of STRAP in which one or more residues have been conservatively substituted with a functionally similar residue and which displays the STRAP modulator activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another, or the substitution of one acidic residue, such as aspartic acid or glutamic acid for another. Such substitutions are described in detail above with respect to the isolated and purified STRAP of the present invention.

The phrase "conservative substitution" also includes the use of a chemically derivatized residue in place of a non-derivatized residue provided that such polypeptide displays the requisite inhibition activity.

Chemical derivative refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a STRAP endogenous ligand, it is typically because one or more conservative or non-conservative substitutions have been made, usually no more than about 30 percent, and preferably no more than 10 percent of the amino acid residues are substituted. Additional residues may also be added at either terminus of a polypeptide for the purpose of providing a "linker" by which the polypeptides of this invention can be conveniently affixed to a label or solid matrix, or carrier. Labels, solid matrices and carriers that can be used with the polypeptides of this invention are described hereinbelow.

Amino acid residue linkers are usually at least one residue and can be 40 or more residues, more often 1 to 10 residues, but do not form STRAP ligand epitopes. Typical amino acid residues used for linking are tyrosine, cysteine, lysine, glutamic and aspartic acid, or the like. In addition, a subject polypeptide can differ, unless otherwise specified, from the natural sequence of a STRAP ligand by the sequence being modified by terminal-NH2 acylation, e.g., acetylation, orthioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the poypeptides in solutions, particularly biological fluids where proteases may be present in this regard, polypeptide cyclization is also a useful terminal modification, and is particularly preferred also because of the stable structures formed by, cyclization and in view of the biological activities observed for such cyclic peptides as described herein.

Any peptide of the present invention may be used in the form of a pharmaceutically acceptable salt Suitable acids which are capable of the peptides with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoracetic acid. propionic acid, glycolic acid, lactic acid, pyruvic acid, oxalic acid, malonic acid. succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono- di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W.H. Freeman Co., San Francisco, 1969; Bodanszky, et al., "Peptide Synthesis", John Wiley & Sons, Second Edition, 1976; J. Melenhofer, "Hormonal Proteins and Peptides", Vol. 2, p. 46, Academic Press (New York), 1983; Merrfield, *Adv Enzymol*, 32:221–96, 1969: Fields et al., *Int. J. Peptide Protein Res.*, 35:161–214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry". Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group, a different, selectively removable protecting group is utilized for amino acids containing a reactive side group such as lysins.

Using a solid phase synthesis as representative, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. A representative method for cyclizing peptides is described by Zimmer et al., *Peptides* 1992, pp. 393–394, ESCOM Science Publishers, B. V., 1993. Typically, tertbutoxycarbonyl protected peptide methyl ester is dissolved in methanol and sodium hydroxide solution are added and the admixture is reacted at 20° C. to hydrolytcally remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cydic peptide is then purified by chromatography.

F.1.2. Monoclonal Antibodies

The present invention describes, in one embodiment, STRAP modulators in the form of monoclonal antibodies which immunoreacts with STRAP and bind the STRAP to modulate receptor activity as described herein. The invention also describes above cell lines which produce the antibodies, methods for producing the cell lines, and methods for producing the monoclonal antibodies.

A monoclonal antibody of this invention comprises antibody molecules that 1) immunoreact with isolated STRAP, and 2) bind to the STRAP to modulate its biological function.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen.

Representative antibodies for use in the present invention are intact immunoglobulin molecules, substantially intact immunoglobulin molecules, single chain immunoglobulins or antibodies, those portions of an immunoglobulin molecule that contain the paratope, including those portions known in the art as Fab, Fab', F(ab')2 and F(v), and also referred to as antibody fragments. Indeed, it is contemplated to be within the scope of the present invention that a monovalent modulator may optionally be is used in the present method. Thus, the terms "modulate", "modulating", and "modulator" are meant to be construed to encompass such promotion.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Methods of producing a monoclonal antibody, a hybridoma cell, or a hybridoma cell culture are described above.

It is also possible to determine, without undue experimentation, if a monoclonal antibody has the same (i.e., equivalent) specificity (immunoreaction characteristics) as a monoclonal antibody, of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihoods it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. "CDRs" (complementarity determining regions) mean the three subregions of the light or heavy chain variable regions which have hypervariable sequences and form loop structures that are primarily responsible for making direct contact with antigen. Antibody molecules having identical, or functionally equivalent, amino acid residue sequences in their CDR regions have the same binding specificity. Methods for sequencing polypeptides are well known in the art The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin that comprises the antibody, and in part by the light chain variable region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention. Thus, the invention contemplates, in one embodiment, a monoclonal antibody of this invention that is humanized by grafting to introduce components of the human immune system without substantially interfering with the ability of the antibody to bind antigen.

The use of a molecular cloning approach to generate antibodies, particularly monoclonal antibodies, and more particularly single chain monoclonal antibodies, is also contemplated. The production of single chain antibodies has been described in the art, see e.g., U.S. Pat. No. 5,260,203, the contents of which are herein incorporated by reference. For this, combinatorial immunoglobulin phagemid libraries are prepared from RNA isolated from the spleen of the immunized animal, and phagemids expressing appropriate antibodies are selected by panning on endotelial tissue. The advantages of this approach over conventional hybridoma techniques are that approximately $10^4$ times as many antibodies can be produced and screened in a single round, and that new specificities are generated by H and L chain combination in a single chain, which further increases the chance of finding appropriate antibodies. Thus, an antibody of the present invention, or a "derivative" of an antibody of the present invention pertains to a single polypeptide chain binding molecule which has binding specificity and affinity substantially similar to the binding specificity and affinity of the light and heavy chain aggregate variable region of an antibody described herein.

F.1.3. Other Modulators

Given the disclosure of the STRAP activity in tissues herein, it is also contemplated that as yet undefined chemical compounds may be used to modulate STRAP activity in tissues in accordance with the methods of the present invention. The identification of such compounds is facilitated by the description of screening assays directed to STRAP activity in tissues presented above.

F.2. Antisense Oligonucleotide Therapy

A therapeutic method according to the present invention may alternatively comprise promoting or inhibiting STRAP in a vertebrate subject by administering an effective amount of a substance that inhibits or promotes expression of a STRAP-encoding nucleic acid segment in the vertebrate. Examples of such a substance, include, for example, an antisense oligonucleotide derived from SEQ ID NO:1. Therapeutic methods utilizing antisense oligonudeotides have been described in the art, for example in U.S. Pat. Nos. 5,627,158 and 5,734,033, the contents of each of which are herein incorporated by reference.

F.3. Gene Therapy

A STRAP gene can be used for gene therapy in accordance with the present invention. Representative gene therapy methods, including liposomal transfection of nucleic acids into host cells, are described in U.S. Pat. Nos. 5,279,833; 5,286,634; 5,399,346; 5,646,008; 5,651,984; 5,841,484; and 5,643,567, the contents of each of which are herein incorporated by reference.

Briefly, STRAP gene therapy directed toward modulation of TGF-β activity in a target cell is described. Target cells include but are not limited to cancerous or tumorous cells. In one embodiment, a therapeutic method of the present invention contemplates a method for modulating of TGF-β activity in a cell comprising the steps of: (a) delivering to the cell an effective amount of a DNA molecule comprising a polynucleotide that encodes a STRAP polypeptide that modulates TGF-β activity; and (b) maintaining the cell under conditions sufficient for expression of said polypeptide.

In a preferred embodiment, the STRAP polypeptide is that essentially as set forth in SEQ ID NO:2. Delivery is preferably accomplished by injecting a DNA molecule into the cell. Where the cell is in a subject delivering is preferably administering the DNA molecule into the circulatory system of the subject. In a preferred embodiment, administering comprises the steps of: (a) providing a vehicle that contains the DNA molecule; and (b) administering the vehicle to the subject.

For introduction of, for example, the STRAP gene, it is proposed that one will desire to preferably employ a vector construct that will deliver the desired gene to the affected cells. This will, of course, generally require that the construct be delivered to the targeted cells, for example, mammalian smooth muscle cells. It is proposed that this may be achieved most preferably by introduction of the desired gene through the use of a viral vector to carry the STRAP sequence to efficiently infect the cells. These vectors will preferably be an adenoviral, a retroviral, a vaccinia viral vector or adeno-associated virus. These vectors are, preferred because they have been successfully used to deliver desired sequences to cells and tend to have a high infection efficiency.

A vehicle is preferably a cell transformed or transfected with the DNA molecule or a transfected cell derived from such a transformed or transfected cell. A representative and preferred transformed or transfected cell is a lymphocyte or a tumor cell from the tumor being treated. Techniques for transforming or transfecting a cell with a DNA molecule of the present invention are set forth above.

Alternatively, the vehicle is a virus or an antibody that specifically infects or immunoreacts with an antigen of the target tissue or tumor. An advantage of a viral infection system is that it allows for a very high level of infection into the appropriate recipient cell. Also, antibodies have been used to target and deliver DNA molecules.

It is also envisioned that this embodiment of the present invention can be practiced using alternative viral or phage vectors, including retroviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

F.4. Dosages

As used herein, an "effective" dose refers to one that is administered in doses tailored to each individual patient manifesting symptoms of improper TGF-β activity sufficient to cause an improvement therein. After review of the disclosure herein of the present invention, one of ordinary skill in the art can tailor the dosages to an individual patient, taking into account the particular formulation and method of administration to be used with the composition as well as patient height, weight, severity of symptoms, and stage of the disorder to be treated.

An effective dose and a therapeutically effective dose are generally synonymous. However, compounds may be administered to patients having reduced symptoms or even administered to patients as a preventative measure. Hence, the composition may be effective in therapeutic treatment even in the absence of symptoms of the disorder.

A unit dose can be administered, for example, 1 to 4 times per day. Most preferably, the unit dose is administered twice a day (BID). The dose depends on the route of administration and the formulation of a composition containing the compound or compounds. Further, it will be appreciated by one of ordinary skill in the art after receiving the disclosure of the present invention that it may be necessary to make routine adjustments or variations to the dosage depending on the combination of agents employed, on the age and weight of the patient, and on the severity of the condition to be treated.

Such adjustments or variations, as well as evaluation of when and how to make such adjustments or variations, are well known to those of ordinary skill in the art of medicine. Evaluation parameters and techniques may vary with the patient and the severity of the disease. Particularly useful evaluative techniques are dispose in the Examples.

F.4.1. Gene Therapy Vector Construct Dosing

Maximally tolerated dose (MTD) of vector construct when administered directly into the affected tissue is determined. Primary endpoints are: 1) the rate of transduction in abnormal and/or normal cells. 2) the presence and stability of this vector in the systemic circulation and in affected cells, and 3) the nature of the systemic (fever, myalgias) and local (infections, pain) toxicities Induced by the vector. A secondary endpoint is the clinical efficacy of the vector construct For example, a 4 ml serum-free volume of viral (e.g. adenoviral, retroviral, etc.) vector construct (containing up to $5 \times 10^7$ viral particles in AIM V media) is administered daily per session. During each session, 1 ml of medium containing the appropriate titer of vector construct is injected into 4 regions of the affected tissue for a total of 4 ml per session in a clinical examination room. This is repeated daily for 4 days (4 sessions). This 16 ml total inoculum volume over 4 days is proportionally well below the one safely tolerated by nude mice (0.5 ml/20 g body weight).

Patient evaluation includes history and physical examination prior to initiation of therapy and daily during the 4 day period of vector construct injection. Toxicity grading is done using the ECOG Common Toxicity Criteria. CBC, SMA-20, urinalysis, and conventional studies are performed daily during this period.

F.4.2. Dose escalation and MTD.

Patients are treated with $3 \times 10^6$ viral particles×4. Once they have all recovered from all grade 2 or less toxicities (except alopecia), and as long as grade 3–4 toxicity is not encountered, a subsequent dose level is initiated in patients. As one grade 3 or 4 toxicity occurs at a given dose level, a minimum of 6 patients are enrolled at that level. As only 1 of 6 patients has grade 3 or 4 toxicity, dose escalation continues. The MTD of vector construct is defined as the dose where 2 of 6 patients experience grade 3 or 4 toxicity. If 2 of 3, or if 3 of 6 patients experience grade 3 or 4 toxicity, the MTD is defined as the immediately lower dose level.

The following escalation schema is followed: 1) level 1, $3 \times 10^6$ viral particles; 2) level 2, $1 \times 10^7$; 3) level 3, $3 \times 10^7$; 4) level 4, $5 \times 10^7$. Patients with measurable disease are evaluated for a clinical response to vector construct. Histology and local symptoms are followed. NE clearance, tyramine administration and other standard tests such as are disclosed in the Examples are employed.

F.5. Formulation of Therapeutic Compositions

The STRAP modulating substance and the substance that inhibits or promotes expression of a STRAP protein or a STRAP-encoding nucleic acid segment are thus adapted for administration as a pharmaceutical composition. Formulation and dose preparation techniques have been described in the art see for example, those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93/25521 of Johnson et al. published Dec. 23, 1993, the entire contents of each of which are herein incorporated by reference.

For the purposes described above, the identified substances may normally be administered systemically or partially, usually by oral or parenteral administration. The doses to be administered are determined depending upon age, body weight, symptom, the desired therapeutic effect, the route of administration, and the duration of the treatment etc. in a human adult, the doses per person per administration are generally between 1 mg and 500 mg, by oral administration, up to several times per day, and between 1 mg and 100 mg, by parenteral administration up to several times per day. Since the doses to be used depend upon various conditions, as mentioned above, there may be a case in which doses are lower than or greater than the ranges specified above.

Solid compositions for oral administration include compressed tablets, pills, dispersible powders, capsules, and granules. In such compositions, one or more of the active substance(s) is or are, admixed with at least one inert diluent (lactose, mannitol, glucose, hydroxypropylcellulose, microcrystalline cellulose, starch, polyvinylpyrrolidone, magnesium metasilicate alminate, etc.). The compositions may also comprise, as is normal practice, additional substances other than inert diluents; e.g. lubricating agents (magnesium stearate, etc.), disintegrating agents (cellulose, calcium glycolate etc.), and assisting agent for dissolving (glutamic acid, aspartic acid, etc.) stabilizing agent (lactose etc.). The tablets or pills may, if desired, be coated with gastric or enteric material (sugar, gelatin, hydroxypropylcellulose or hydroxypropylmethyl cellulose phthalate, etc.). Capsules include soft ones and hard ones.

Liquid compositions for oral administration include pharmaceutically-acceptable emulsions, solutions, suspensions, syrups and elixirs. In such compositions, one or more of the active substance(s) is or are admixed with inert diluent(s) commonly used in the art (purified water, ethanol etc.). Besides inert diluents, such compositions may also comprise adjuvants (wetting agents, suspending agents, etc.), sweetening agents, flavoring agents, perfuming agents and preserving agents.

Other compositions for oral administration include spray compositions which may be prepared by known methods and which comprise one or more of the active substance(s). Spray compositions may comprise additional substances other than inert diluents: e.g. preserving agents (sodium sulfite etc.), isotonic buffer (sodium chloride, sodium citrate, citric acid, etc.). For preparation of such spray compositions, for example, the method described in U.S. Pat. Nos. 2,868, 691 or 3,095,355 may be used.

Injections for parenteral administration include sterile aqueous or non-aqueous solution, suspensions and emulsions. In such compositions, one or more of active substance (s) is or are admixed with at least one inert aqueous diluent(s) (distilled water for injection, physiological salt solution etc.) or inert non-aqueous diluent(s) (propylene glycol, polyethylene glycol, olive oil, ethanol, POLYSOL-BATE 80® etc.). Injections may comprise additional other than inert diluents: e.g. preserving agents, wetting agents, emulsifying agents, dispersing agents, stabilizing agents (lactose, etc.), assisting agents such as for dissolving (glutamic acid, aspartic acid, etc.). They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before use.

Other compositions for administration include liquids for external use, and endermic linaments (ointment, etc.), suppositories and pessaries which comprise one or more of the active substance(s) and may be prepared by known methods.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed w departing from the spirit and scope of the invention.

Example 1

Isolation and Purification of STRAP Protein

Cloning of STRAP. Northern blot and Southern blot analysis—Y190 containing pAS2-R4C was transformed with a pACT-mouse embryonic cDNA library, and transformants were subjected to selection for histidine prototrophy on SC-his, -trp, -leu plates containing 25 mM 3-aminotriazole (as described in Harper at al., *Cell* 75: 805–816 (1993) and Durfee et al., *Genes Dev.* 7:555–569 (1993)) and rare surviving colonies were then screened for β-galactosidase activity using a colony filter lift assay. Resulting clones, after second screening, were mated with Y187 containing the unrelated proteins p53, lamin, SNF1 and CDK2 fused to the GAL4 DNA-binding domain and tested for β-galactosidase activity. Positive clones were recovered from yeast and retransformed into Y190 with one of several unrelated molecules including lamin, SNF1, p53 or CDK2 in pAS2, for further testing of the specific interaction.

A color photograph was prepared showing STRAP or FKBP12.6 in pACT transformed into yeast strain Y190 containing R4C or one of several unrelated proteins including lamin. SNF1, p53 or CDK2 in pAS2. Transformants were tested for β-galactosidase activity by colony filter lift assay. A blue color indicated a positive interaction.

STRAP cDNA was used as a probe to screen a mouse embryonic (8.5–9.0 dpc) cDNA library in λZAP II (Stratagene). Five clones showed an in-frame stop codon (TGA) 72 bp upstream from the ATG start codon and kozak consensus sequence. A blot (Clontech) with mRNA (2 µg per lane) from multiple mouse tissues was probed with $^{32}$P- labeled STRAP and Actin cDNAs. A membrane (Clontech) containing genomic DNA (4 µg per lane) digested with $EcoR_1$, from various eukaryotic species was probed with $^{32}$P-labeled STRAP.

Thus, to search for intracellular signal mediators, a modified version of the yeast two-hybrid system (as described in Harper et al., Cell 75: 805–816 (1993) and Durfee et al., Genes Dev. 7:555–569 (1993)) was utilized to screen a mouse embryonic cDNA library using the cytoplasmic domain of type I TGF-β receptor from rat (R4C) (Bassing et al., Science 263:87–89 (1994)) as the bait. Fourteen positive clones that specifically interacted with R4C were subdivided into three groups. Twelve clones encoded FKBP12, a binding protein for FK506 and rapamycin (Standaert et al., Nature 346:671–674 (1990)), which was previously shown to interact specifically with type I receptors. See e.g., Wang et al., Cell 86:435–444 (1996). One clone encoded FKBP12.6, which shares many structural and functional similarities with FKBP12 (Lam et al., J. Biot. Chem. 270:26511–26522 (1995)), and also showed strong interaction with R4C in yeast.

The remaining clone encoded the novel WD-domain containing protein according to the present invention, designated STRAP (Serine-Threonine Kinase Receptors Associated Protein). The specificity of the interaction between R4C and STRAP in yeast was tested using a panel of unrelated proteins, none of which interacted with STRAP. When the cytoplasmic domain of R4 was tested, positive interaction was detected with STRAP and FKBP12.6. The specificity and strength of the interaction between R4C and STRAP in the yeast system were further confirmed by a quantitative β-galactosidase assay.

Table 2 summarizes yeast strain Y190 transformed with various plasmids as indicated. Four independent colonies of each transformation were first grown in appropriate selection media. β-galactosidase assays were performed using o-nitrophenyl-β-D-galactopyranoside as substrate as described in Ausubel et al., Current Protocols in Molecular Biology, (J. Wylie & Sons, N.Y.) (1992). Averages from four independent transformants were expressed in a relative scale. Experiments were repeated four times with similar results.

TABLE 2

Interaction of STRAP with the Cytoplasmic Domain of the Type 1 TGF-β Receptor

| Transforming Plasmids | β-galactosidase Activity |
|---|---|
| STRAP + R4C | 24.3 |
| STRAP + p53 | <1.0 |
| STRAP + CDK2 | 1.2 |
| STRAP + SNF1 | 1.4 |
| FKBP12.6 + R4C | 181.8 |
| FKBP12.6 + p53 | 1.1 |

The STRAP clone yielded a 1.6 kb cDNA that contained an open reading frame. Screening of another mouse embryonic cDNA library with the STRAP cDNA as probe resulted in the isolation of five clones that yielded ~1.8 kb cDNAs with an in-frame termination codon preceding the putative initiating methionine of the STRAP open reading frame. This open reading frame predicted a protein of 351 amino acids with a Mr of 38,523 (FIG. 2A and SEQ ID NO:2). The in vitro translated STRAP migrates with a molecular mass of about 39 kD on SDS-PAGE. Sequence analysis indicates that STRAP contains six WD domains and shows ~19% amino acid similarity with TRIP-$_1$, a TGF-β type II receptor associated protein, which is described in Chen et al., Nature 377:548–552 (1995). Some of these similarities are among the conserved amino acid residues within the WD repeats (FIG. 2B).

Figure 2C:
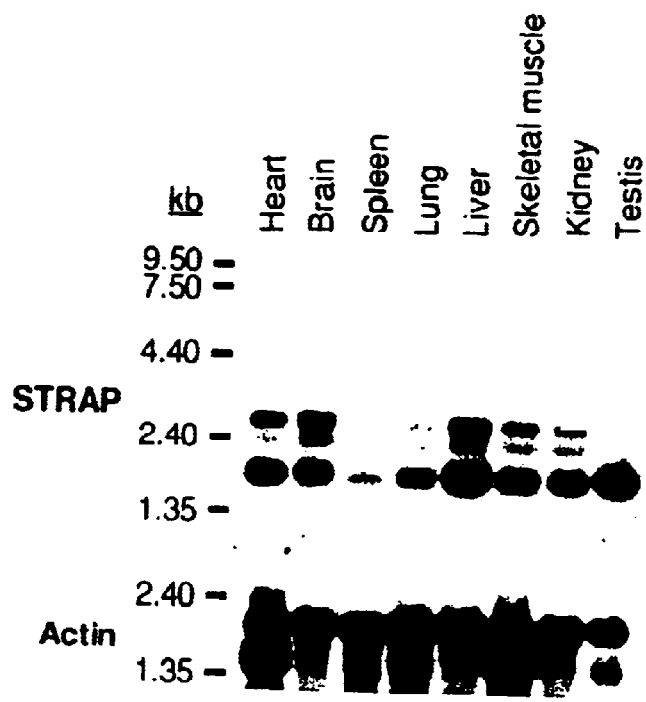
FIG. 2C is an autoradiograph of a Northern Blot with mRNA from multiple mouse tissues was probed with $^{32}$P-labeled STRAP (top) and Actin (bottom) cDNAs.
Figure 2D:
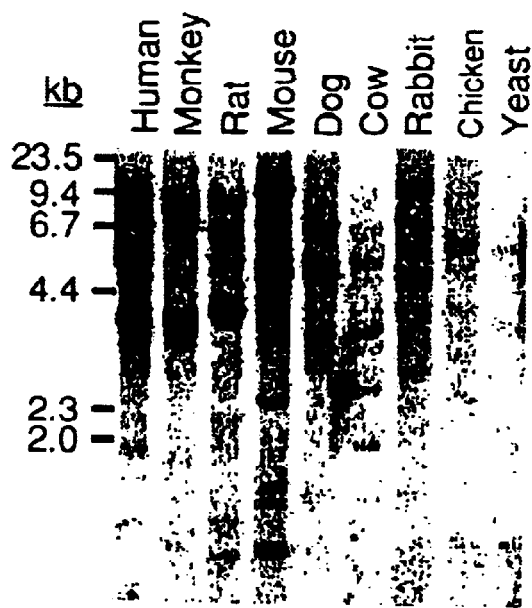
FIG. 2D is an autoradiograph of a Southern Blot containing genomic DNA from various eukaryotic species digested with EcoR1 and probed with $^{32}$P-labeled STRAP.

To analyze the expression pattern of the STRAP gene, Northern blot analysis of poly(A)+RNA from different mouse tissues was performed (FIG. 2C). A major transcript of ~1.6 kb was detected in all tissues examined, with the highest levels in liver and testis and lesser abundance in spleen. In some tissues larger transcripts were detected. Southern blot analysis of genomic DNA from different species using the STRAP cDNA as a probe revealed conservation of the STRAP gene from yeast to mammals (FIG. 2D).

Example 2

Evaluation of the Association of STRAP with TβR-1 In Vivo

Expression plasmids—The whole or partial coding region (N-terminal 294 amino acids) of STRAP were amplified by PCR and subcloned into a mammalian expression vector, pcDNA3 (Invitrogen) with one copy of the Flag epitope in-frame to the C-terminus to generate STRAP-Flag and STRAP (1-294)-Flag, respectively. Similarly STRAP-HA was made. The entire cytoplasmic domain of R4 (amino acids 146–501) was fused in-fame to the 3' end of the GAL4 DNA-binding domain into pAS2 as described in Harper et al., Cell 75: 805–816 (1993) and Durfee et al., Genes Dev. 7:555–569 (1993). Expression constructs for TGF-β receptors, Smad1, Smad6, and Smad7 have been described. See e.g., Kretzschmar et al., Genes Dev. 11:984–995 (1997); imamura et al. Nature 389:622–626 (1997); Nakao et al., Nature 389:631–635 (1997); Wieser et al., EMBO J. 14:2199–2208 (1995); and Chen et al., EMBO J. 16:3866–3876 (1997).

immunoprecipitation, immunoblotting and phosphate labeling—All of these procedures were performed essentially as described in Hoodless et al., Cell 85:489–500 (1996). In brief, COS-1 cells were transiently transfected with the indicated consults and cell lysates were subjected to immunoprecipitation with anti-Flag M2 monoclonal antibody (IBI, Eastman Kodak Company, Rochester, N.Y.), anti-HA polyclonal antibody (Y11, Santa Cruz Biotechnology, Inc., Santa Cruz, Calif.), anti-TβR-I polyclonal antibody (Santa Cruz) or anti-TβR-II polyclonal antibody (Santa Cruz Biotechnology, Inc., Santa Cruz, Calif.) followed by adsorption to protein G-Sepharose (Pharmacia Biosystems Aktiebolaget, Uppsala, Sweden). Immunoprecipitates were washed, separated by SDS-PAGE, and transferred to membranes. Tagged proteins were detected using anti-Flag antibody or anti-HA antibody and chemiluminescence. For $^{32}$P-phosphate labeling, transiently transfected COS-1 cells were metabolically labeled with 1 mCi/ml $^{32}$P-orthophosphate for 3 hours at 37° C. and equal amount of extracts immunoprecipitated with anti-Flag antibody. Phosphorylated proteins were detected by SDS-PAGE and autoradiography. Quantitation of STRAP phosphorylation was performed using IMAGEQUANT® software (Molecular Dynamics, Inc., Sunnyvale, Calif.).

Affinity crosslinking—Transfected COS-1 cells were affinity labeled with 200 pM $^{125}$-I-TGF-β1 by chemical crosslinking as described in Wrana et al., Cell 71:1003–1014 (1992) and lysates were immonoprecipitated with anti-Flag antibody. Affinity labeled receptor complexes co-precipitated with STRAP were visualized by SDS-PAGE and autoradiography.

To evaluate the association of STRAP with TβR-I in vivo, HA-tagged wild type and mutant forms of TβR-I with Flag-tagged STRAP in COS-1 cells were expressed. Cell lysates were subjected to immunoprecipitation with antibodies to Flag and each immunoprecipitate was then probed with antibodies to HA. A comparable amount of TβR-I was detected in each immunoprecipitate (FIG. 3A, first panel, lanes 4–7), revealing that TβR-I can be co-immunoprecipitated with STRAP. Reciprocal experiments, in which proteins immunoprecipitated by antibodies to TβR-I were blotted with an anti-Flag antibody (FIG. 3A, second panel), confirmed the association of STRAP with ligand-free TβR-I and this association was not detectably affected by the mutations K232R (kinase negative), T204D (constitutively active) or 185–204 (activation incompetent) in TβR-I.

Figure 3A:
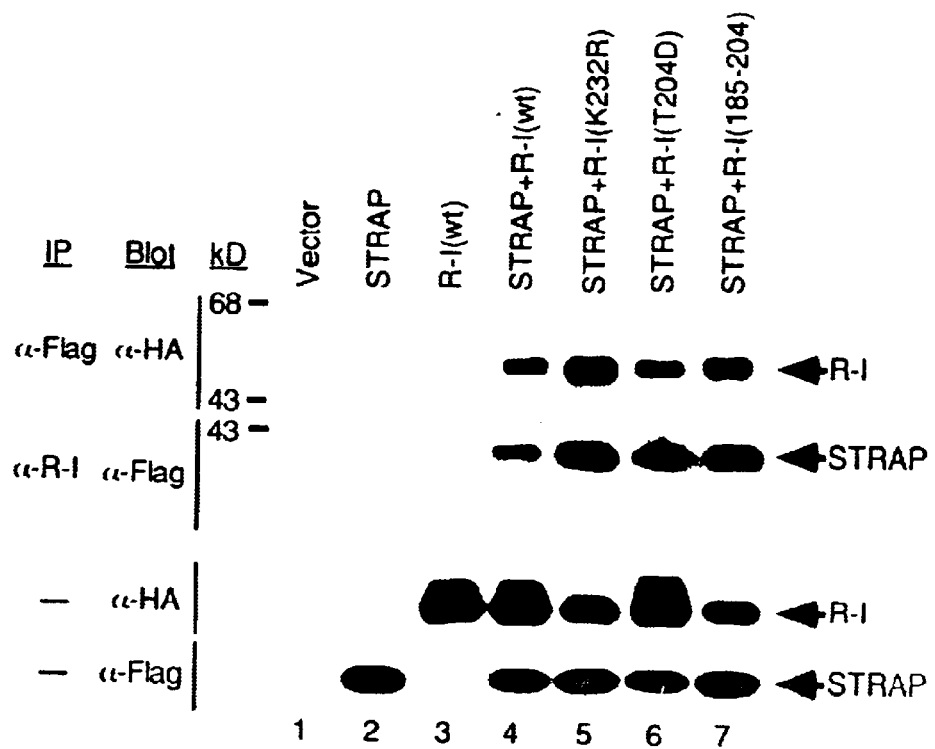
FIG. 3A is an autoradiograph of an immunoblot showing in vivo association of STRAP with TβR-I and TβR-II in presence or absence of TGF-β1 and that STRAP can also associate with Smad6 or Smad7 but not with Smad1. COS-1 cells were transiently transfected with the indicated combinations of STRAP-Flag and HA-tagged wild type (wt) and mutants of TβR-I as indicated. Cell lysates were subjected to immunoprecipitation (IP) followed by immunoblotting (blot) as indicated (top two). Expression of TβR-I proteins and STRAP was determined by immunoblotting (bottom two).
Figure 3B:
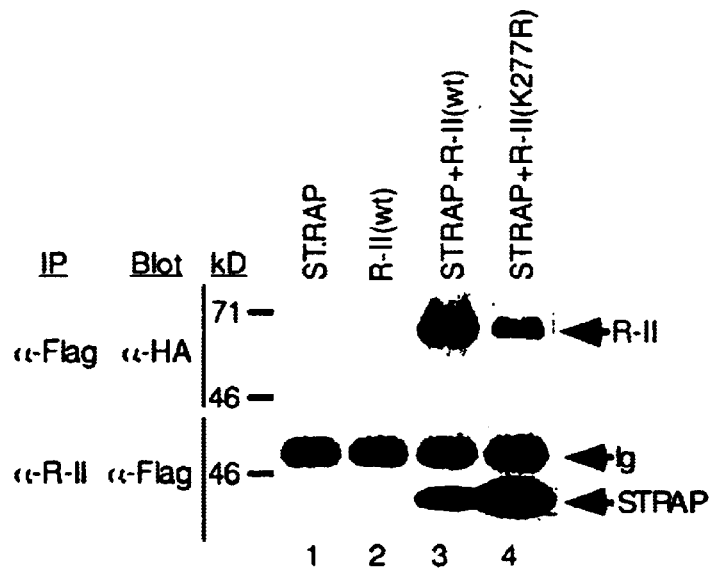
FIG. 3B is an autoradiograph of an immunoblot showing that STRAP interacts with TβR-II. COS1 cells were transiently transfected with the indicated combinations of STRAP-Flag and HA-tagged TβR-II constructs. Cell lysates were immunoprecipitated and then immunoblotted as described. Ig=immunoglobulin.
Figure 3C:
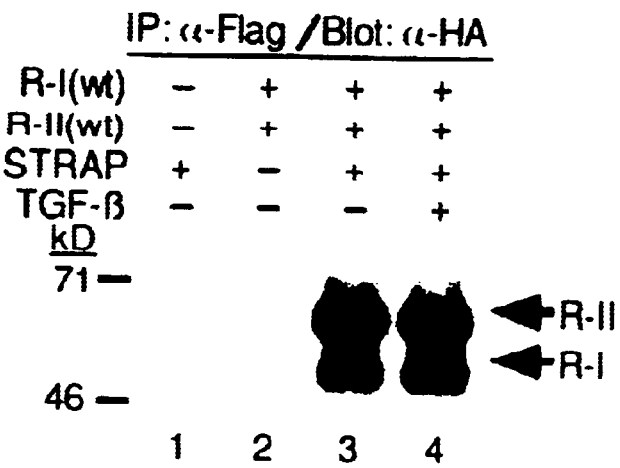
FIG. 3C is an autoradiograph of an immunoblot showing that TGF-β does not affect the association of STRAP with TβR-I and TβR-II. A similar experiment was performed in the absence or presence of TGF-β1 (240 pM) for 20 min.
Figure 3D:
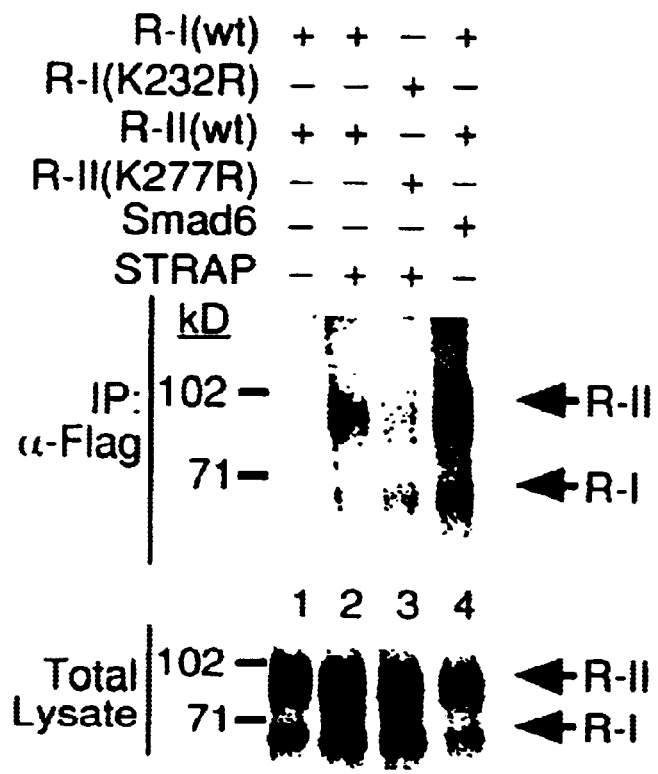
FIG. 3D is an autoradiograph of a protein gel showing the interaction of STRAP with TGF-β1-bound receptors. COS-1 cells were transfected with STRAP-Flag or Flag-Smad6 [serves as positive control]in combination with the wild-type (wt) or kinase-defective (K→R) HA-tagged TβR-I and hexahistidine-tagged TβR-II as indicated. Affinity labeled receptor complexes co-precipitated with STRAP were indicated (top). Similar levels of receptor expression were confirmed by analyzing aliquots of total cell lysates by SDS-PAGE (bottom).

To determine whether STRAP can also interact with TβR-II, similar experiments were performed using TβR-II coexpressed with STRAP (FIG. 3B). Co-immunoprecipitation of TβR-II with STRAP and vice versa demonstrated the specific interaction between these proteins. Additionally, co-immunoprecipitation of both receptors with STRAP was not affected by the treatment of cells with TGF-β1 (FIG. 3C, lane 4). Finally, $^{125}$I-TGF-β-bound TβR-I-TβR-II heteromeric complexes could be co-immunoprecipitated with STRAP in affinity crosslinking experiments (FIG. 3D). Thus, STRAP associates with TβR-I and TβR-II in the presence or absence of ligand in mammalian cells.

Figure 3E:
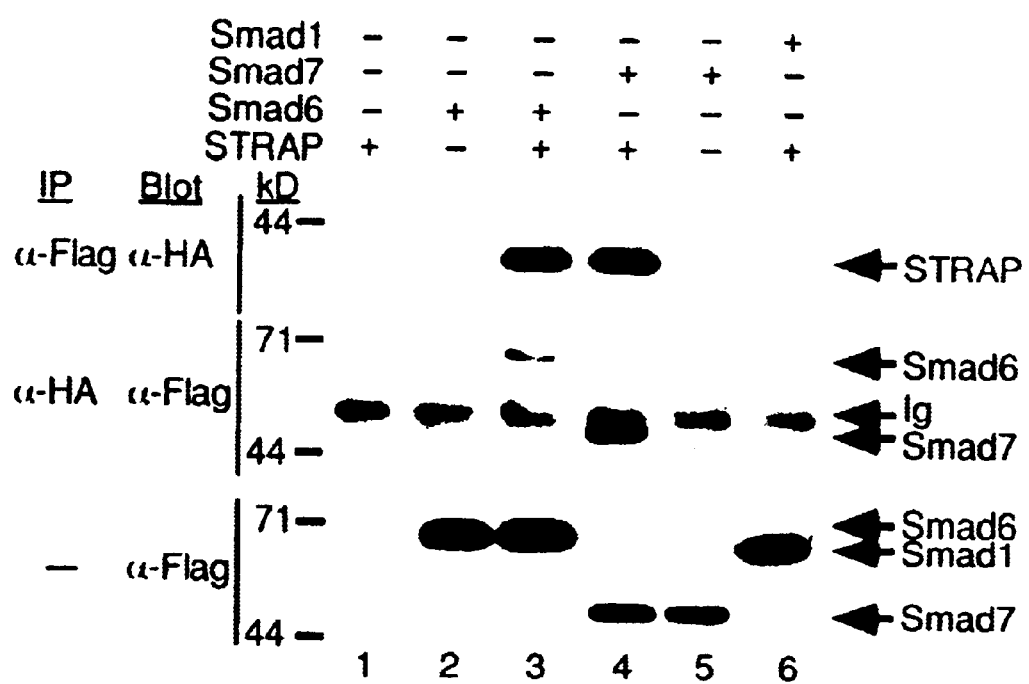
FIG. 3E is an autoradiograph of an immunoblot showing the association of STRAP with Smad6 and Smad7 but not with Smad1. COS-1 cells were transfected with the indicated combinations of STRAP-HA and Flag-tagged SMADs. In similar experiments cell lysates were subjected to immunoprecipitation followed by immunoblotting as indicated (top two). Exptession levels of SMAD proteins were monitored by immunoblotting (bottom).

Since the inhibitory SMADs, Smad6 and Smad7 show stable interaction with type I receptors (e.g. Imamura et al. Nature 389:622–626 (1997); Nakao et al., Nature 389:631–635 (1997)), it was examined whether STRAP could associate with these SMADs in co-immunoprecipitation experiments. Co-precipitation of STRAP with Smad6 or Smad7 and in reciprocal experiments, co-precipitation of Smad6 or Smad7 with STRAP demonstrated that STRAP stably associates with Smad6 and Smad7 (FIG. 3E). No interaction was observed between STRAP and Smad1 in similar experiments, indicating the specificity of the interactions.

Thus, in vivo association of STRAP with TβR-I and TβR-II in presence or absence of TGF-β1 was examined. STRAP can also associate with Smad6 or Smad7 but not with Smad1. An autoradiograph of an immunoblot showing interaction of STRAP and TβR-I was prepared (FIG. 3A). COS-1 cells were transiently transfected with the indicated combinations of STRAP-Flag and HA-tagged wild type (wt) and mutants of TβR-I as indicated. Cell lysates were subjected to immunoprecipitation followed by immunoblotting. Expression of TβR-I proteins and STRAP was determined by immunoblotting.

An autoradiograph of an immunoblot showing that STRAP interacts with TβR-II was also prepared and is presented in FIG. 3B. COS-1 cells were transiently transfected with the above-described combinations of STRAP-Flag and HA-tagged TβR-II constructs. Cell lysates were immunoprecipitated and then immunoblotted as described above. An autoradiograph of an immunoblot showing that TGF-β does not affect the association of STRAP with TβR-I and TβR-II was also prepared and is presented in FIG. 3C. A similar experiment was performed in the absence or presence of TGF-β1 (240 pM) for 20 min.

An autoradiograph of a protein gel showing the interaction of STRAP with TGF-β1-bound receptors was also prepared and is presented in FIG. 3D. COS-1 cells were transfected with STRAP-Flag or Flag-Smad6 (serves as positive control) in combination with the wild-type (wt) or kinase-defective (K→R) HA-tagged TβR-I and hexahistidine-tagged TβR-II as described above. Affinity labeled receptor complexes co-precipitated with STRAP were observed at about 71 kD (TβR-I) and about 102 kD (TβR-II). Similar levels of receptor expression were observed in analyzing aliquots of total cell lysates by SDS-PAGE (about 71 kD (TβR-I) and about 102 kD (TβR-II)).

An autoradiograph of an immunoblot showing the association of STRAP with Smad6 and Smad7 but not with Smad1 was also prepared and is presented in FIG. 3E. COS-1 cells were transfected with the above-indicated at combinations of STRAP-HA and Flag-tagged SMADs. In similar experiments cell lysates were subjected to immunoprecipitation followed by immunoblotting. Expression levels of SMAD proteins were monitored by immunoblotting.

Figure 4A:
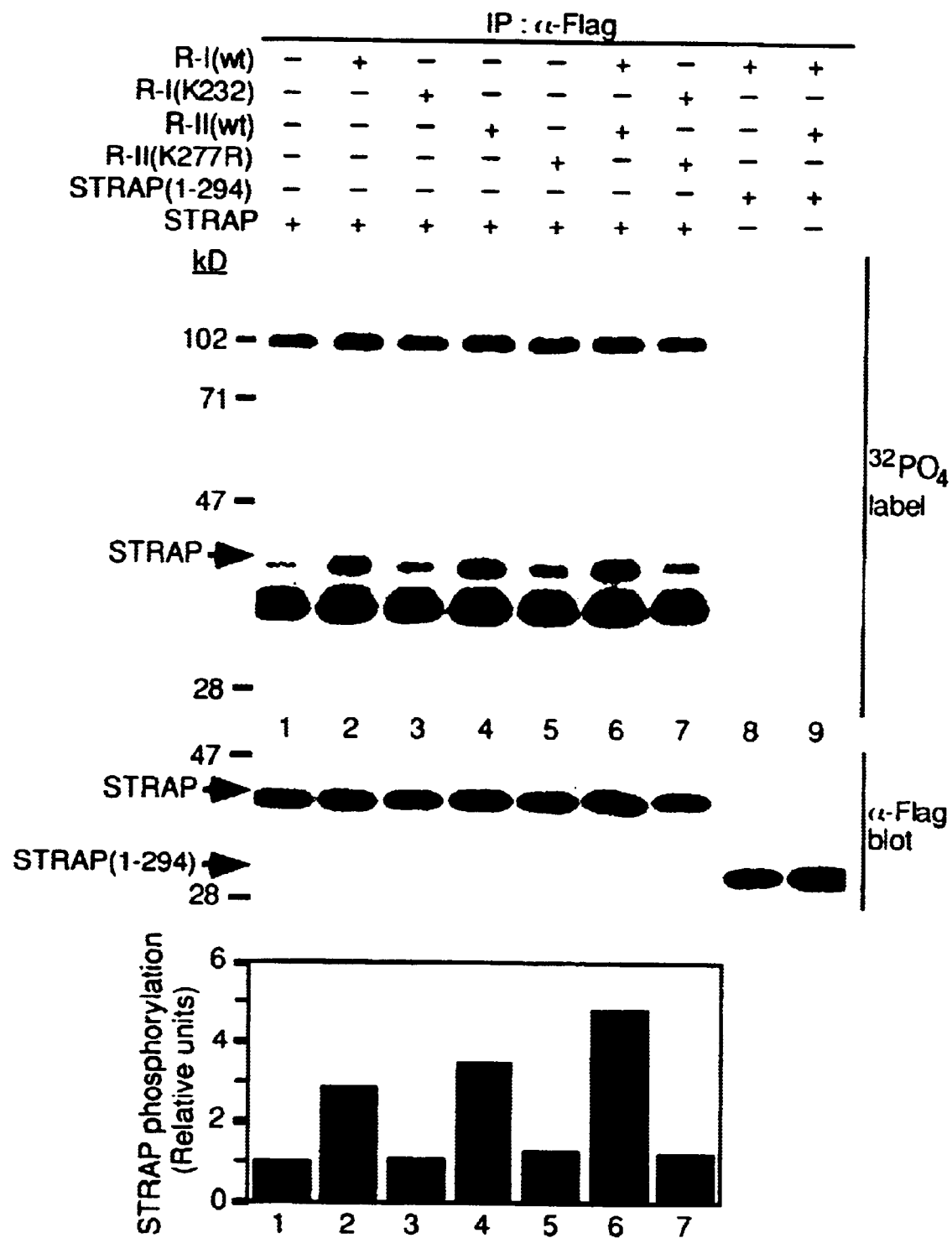
FIG. 4A is an autoradiograph of a protein gel showing COS-1 cells transiently transfected with STRAP-Flag or STRAP (1-294)-Flag in combination with wild-type or kinase defective HA-tagged TβR-I and/or hexahistidine-tagged TβR-II as indicated, and showing that the C-terminus of STRAP is required for its TGF-β receptor-dependent phosphorylation. Cells were metabolically labeled with $^{32}$P-orthophosphate and equal amount of extracts immunoprecipitated with anti-Rag antibody. Phosphorylated STRAP was detected by SDS-PAGE and autoradiography (top). Equivalent expression of STRAP-Flag and STRAP (1-294)-Flag proteins was confirmed by immunoblotting (middle). Phosphate incorporated into STRAP is plotted in relative units (bottom). The result is representative of five independent experiments.

For downstream signaling from the receptor kinases to culminate in transcriptional regulation of target genes, the phosphorylation of signaling components is often essential. To test whether STRAP is a substrate for the serine-threonine kinase receptors the phosphorylation of STRAP in vivo was analyzed when it was coexpressed with different combinations of TGF-β receptors. Metabolic labeling of transfected cells with $^{32}$P-orthophosphate followed by immunoprecipitation of STRAP with ant-Flag antibody indicated a basal level of STRAP phosphorylation in COS-1 cells without exogenous receptor expression (FIG. 4A, lane 1). An increase in STRAP phosphorylation was detected in COS-1 cells expressing TβR-I (lane 2). This increase was dependent on TβR-I kinase activity because a point mutation (K232R) that abolishes TβR-I kinase activity prevented the increase in STRAP phosphorylation (lane 3). Co-transfection of STRAP with TβR-II resulted in a significant increase in STRAP phosphorylation (lane 4) but a kinase inactive mutant (K277R) was unable to induce the phosphorylation of STRAP (lane 5). A further increase in the phosphorylation of STRAP was observed in cells expressing both TβR-I and TβR-II (lane 6) and the kinase activity of both was required for this increase (lane 7). Deletion of tie C-terminal 57 amino acids of STRAP abolished both its basal and receptor-induced phosphorylation (lanes 8.9), indicating that the C-terminus of STRAP is required for its phosphorylation.

Figure 4B:
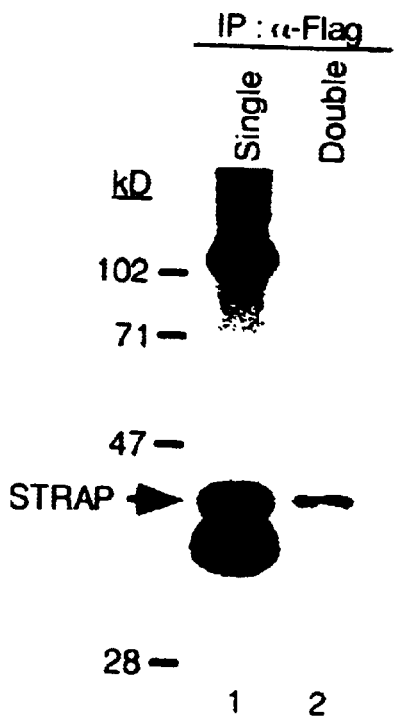
FIG. 4B is an autoradiograph of a protein gel providing confirmation of the phosphorylated band as STRAP. The immunoprecpitate from lane 6 of FIG. 4a (lane 1) was boiled with Laemmli sample buffer to disrupt the complex and then subjected to second IP with anti-Rag antibody (lane 2).

Double immunoprecipitation from $^{32}$P-orthophosphate labeled cells with anti-Flag antibody confirmed the identity of phosphorylated STRAP as the ~40 kD band (FIG. 4B). At least two other phosphoproteins were also detected in the anti-Flag immunoprecipitates, consistent with the presence of alternate kinases that might phosphorylate STRAP. A low level of phosphorylation of STRAP was observed in R1B/L17 mink lung epithelial cells deficient in TβR-I. STRAP phosphorylation in these cells was stimulated when TβR-I was co-transfected with STRAP. These data suggest that the increase in STRAP phosphorylation may be mediated by either TGF-β receptors, receptor associated kinases or STRAP associated kinases that are activated by TGF-β receptors in a multimeric complex.

Thus, an autoradiograph (FIG. 4A) of a protein gel showing COS-1 cells transiently transfected with STRAP-Flag or STRAP (1-294)-Flag in combination with wild-type or kinase defective HA-tagged TβR-I and/or hexahistidine-tagged TβR-II as indicated, and showing that the C-terminus of STRAP is required for its TGF-β receptor-dependent phosphorylation was prepared. Cells were metabolically labeled with $^{32}$P-orthophosphate and equal amount of extracts immunoprecipitated with anti-Flag antibody. Phosphorylated STRAP was detected by SDS-PAGE and autoradiography. Equivalent expression of STRAP-Flag and STRAP (1-294)-Flag proteins was confirmed by immunoblotting. Phosphate incorporated into STRAP is potted in relative units. The result presented in FIG. 4A is representative of five independent experiments.

An autoradiograph (FIG. 4B) of a protein gel providing confirmation of the phosphorylated band as STRAP was also prepared. The immunoprecipitate from lane 6 of FIG. 4A (lane 1) was boiled with Laemmli sample buffer to disrupt the complex and then subjected to second IP with anti-Flag antibody (lane 2).

A bar graph (FIG. 4C) showing TGF-β-induced transcriptional activation of the 3TP promoter is inhibited by STRAP was also prepared. R1B/L17 cells deficient in TβR-I were transiently transfected with p3TP-Lux reporter, β-gal reporter, TβR-I and increasing amounts of STRAP. Luciferase activity was normalized to β-galactosidase activity. These experiments were performed in triplicate four times with similar results. Data are means±SEM of triplicate determinations from a representative experiment.

Example 3

Interactions of STRAP with TGF-B Receptors and Inhibitory SMADs

Transcriptional response assay—The mink lung epithelial cell line derivative R-1B/L17 was transiently transfected with an appropriate combination of reporters, expression plasmids, and empty vector using a DEAE-dextran method. In each experiment total equal amounts of DNA were transfected. Cells were subsequenty incubated in the absence or presence of 100 pM TGF-β1 for 20 hours. The relative luciferase activity was measured in cell lysates as described in Wrana et al., Cell 71:1003–1014 (1992), and normalized for transfection efficiency.

Figure 4C:
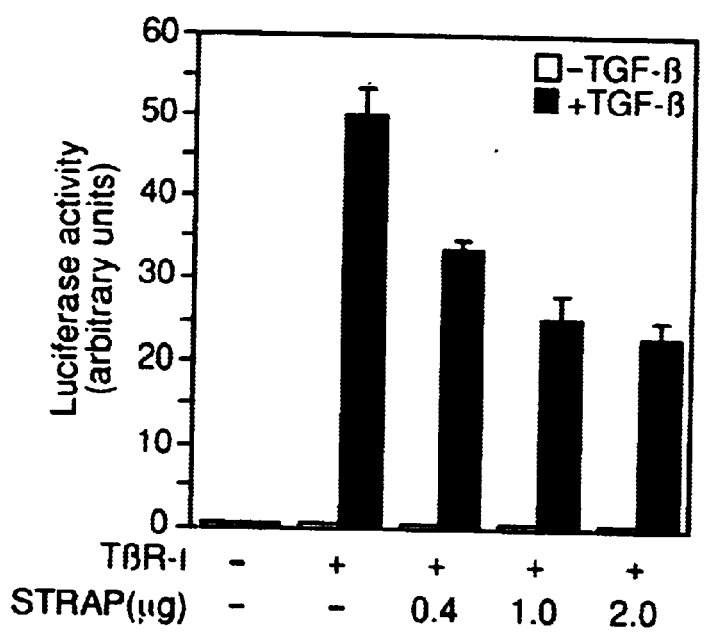
FIG. 4C is a bar graph showing TGF-β-induced transcriptional activation of the 3TP promoter is inhibited by STRAP. R1B/L17 cells deficient in TβR-I were transiently transfected with p3TP-Lux reporter, β-gal reporter, TβR-I and increasing amounts of STRAP. Luciferase activity was normalized to β-galactosidase activity. These experiments were performed in triplicate four times with similar results. Data are means ± SEM of triplicate determinations from a representative experiment.

To explore the functional significance of the interactions of STRAP with TGF-β receptors and inhibitory SMADs, analyses on a TGF-β responsive reporter, p3TP-Lux, which contains elements from the PAI-1 promoter, and drives expression of a luciferase reporter gene, was performed. See Wrana et al., Cell 71:1003–1014 (1992). TβR-I restores the responsiveness to TGF-β in transfected RIB/L17 cells (FIG. 4C). Overexpression of STRAP suppressed the TGF-β-induced increase in luciferase activity in a dose-dependent manner. In HepG2 cells, which possess receptors and are TGF-β responsive, the stimulation of the 3TP promoter by TGF-β was inhibited by STRAP. The same effect was seen in Mv1Lu mink lung epithelial cells. These results suggest that STRAP participates in the negative regulation of transcription by TGF-β.

These results strongly suggest that STRAP interacts specifically with the TGF-β receptors and the inhibitory SMADs, and is involved in an early step in TGF-β signaling. The increase in the phosphorylation of STRAP is dependent on the kinase activity of the receptors.

Many WD-repeat proteins help to assemble macromolecular complexes, as described in Clapham et al., Nature 365:403–406 (1993). Such proteins present a changeable surface for protein-protein interactions and are capable of protein-induced conformational changes. See e.g., Neer et al. Nature 371:297–300 (1994). STRAP forms homo-oligomers most likely through the WD-repeats and may be required for recruiting the negative regulatory SMADs.

Smad6 and Smad7 to the receptor complex. Thus, STRAP is involved in the negative regulation of TGF-β signaling. Analogous to the recruitment of signaling components to receptor tyrosine kinases as described in Marshall, Cell 80:179–185 (1995), it is thus contemplated that STRAP is involved generally in recruiting downstream regulatory molecules to the receptor serine-threonine kinases.

Example 4

STRAP and Smad7 Synergize in the Inhibition of Transforming Growth Factor-β Signaling Smad proteins play a key role in the intracellular signaling of the transforming growth factor-β (TGF-β) superfamily of extracellular polypeptides that initiate signaling from the cell surface through serine/threonine kinase receptors. A subclass of Smad proteins, Smad6 and Smad7, has been shown to function as intracellular antagonists of TGF-β family signaling. The identification of a WD40 repeat protein, STRAP that associates with both type I and type II TGF-β receptors and is involved in TGF-β signaling is disclosed herein above. In this Example it is demonstrated that STRAP synergizes specifically with Smad7, but not with Smad6 (an antagonist of BMP signaling), in the inhibition of TGF-β-induced transcriptional responses.

STRAP does not show any cooperation with a C-terminal deletion mutant of Smad7, that does not bind with the receptor and consequently has no inhibitory activity. STRAP associates stably with Smad7, but not with the Smad7 mutant. STRAP recruits Smad7 to the activated type I receptor and forms a complex. Moreover, STRAP stabilizes the association between Smad7 and the activated receptor, thus assisting Smad7 in preventing Smad2/Smad3 access to the receptor. The C-terminus of STRAP is required for its phosphorylation in vivo which is dependent upon the TGF-β receptor kinases, and is further potentiated by Smad7. However, STRAP is not a direct substrate of the receptors. Thus, a mechanism is characterized with respect to how STRAP and Smad7 function synergistically to block TGF-β-induced transcriptional activation.

Materials and Methods

Cell lines and transfections. Mv1Lu and HepG2 cells were obtained from the American Type Culture Collection (ATCC) and maintained in Dulbecco's modified Eagle's medium (DMEM) supplemented with 10% fetal bovine serum (FBS) and nonessential amino acids. COS-1 cells were grown in DMEM containing 10% FBS. For transient transfections, HepG2 cells were seeded at 20% confluency and transfected overnight using the calcium phosphate-DNA precipitation method as described by Datta, P. K. and S. Bagchi (1994) J. Biol. Chem. 269: 25392–25399. For transfections in COS-1, cells were seeded at 50% confluency and were transfected using the calcium phosphate-DNA precipitation method for five hours, or using FuGENE 6 (Boehringer Mannheim, Indianapolis, Ind.)transfection reagents, according to the manufacturer's instructions. Mv1Lu cells were transfected using a DEAE-dextran transfection method (Promega, Madison. Wis.) following manufacturers instructions.

Plasmid constructs, The complete coding region of STRAP was amplified by polymerase chain reaction (PCR) and subcloned into a mammalian expression vector, pcDNA3 (Invitrogen), with one copy of the epitope in-frame to the C-terminus of STRAP to generate pcDNA3STRAP-Flag or pcDNA3-STRAP-HA. The truncation mutant, pcDNA3STRAP(1-294)-Flag was constructed similarly by amplifying the coding sequence of STRAP from amino acid 1 to 294 by PCR. The full coding sequence of STRAP was amplified by PCR and subcloned in-frame into BamHI/XhoI sites of pGEX-4T-1 GST expression vector (Pharmacia Biosystems Aktiebolaget, Uppsala, Sweden). The cytoplasmic domain of TβR-I was amplified from pcDNA3-TβR-I (T204D) and subcloned in-frame into SmaI/XhoI sites of pGEX4T-1. All constructs were verified by sequencing.

Immunoprecipitation and Immunoblot Analysis. COS-1 cells were transfected with expression constructs as indicated. After 40 hours, cells were washed, scraped and solubilized in lysis buffer (50 mM Tris-HCl, pH 7.5, 150 mM NaCl, 10 mM EDTA, 0.5% Nonidet P-40, 0.5 mM dithiothreitol, 5 mM sodium fluoride, 0.5 mM sodium orthovanadate. 1.0 mM phenylmethylsulfonyl fluoride, and 2 µg/ml of each of leupeptin, pepstatin and aprotinin). Cleared cell lysates were incubated with anti-Flag M2 monoclonal antibody (Sigma Chemical Company, St. Louis, Mo.), anti-HA polyclonal antibody (Y11, Santa Cruz Biotechnology, Inc., Santa Cruz, Calif.) or anti-Myc 9E10 monoclonal antibody (Santa Cruz Biotechnology, Inc., Santa Cruz, Calif.) for 2 hr at 4° C., followed by incubation with protein G-Sepharose (Sigma Chemical Company, St. Louis, Mo.) for 1 hr. Immunoprecipitates were washed four times with lysis buffer. The immune complexes were eluted by boiling for 3 min in SDS sample buffer and analyzed by SDS-PAGE. Proteins were electrotransferred to polyvinylidine fluoride membranes (Millipore Corporation, Bedford, Mass.) and immunoblotted with either anti-Flag antibody or anti-HA antibody followed by the detection using an enhanced chemiluminescence system. Expression of different proteins was monitored by immunoblotting after SDS-PAGE and electotransfer of proteins in total cell lysates.

In vivo phosphorylation. COS-1 cells were cotransfected with expression plasmids as indicated. After 40 hr, cells were washed and preincubated with phosphate-free media containing 0.2% FBS. The cells were then incubated with media containing 1 mCi/ml $^{32}$P-orthophosphate for 2 hr at 37° C. The cells were washed and solubilized in lysis buffer. $^{32}$P-labeled proteins were immunoprecipitated with either anti-Flag antibody or anti-HA antibody and the immunoprecipitates were washed six times with lysis buffer cotaining 1% Nonidet P-40 and 0.1% SDS (wash buffer). Phosphorylated proteins in the immunoprecipitates were detected by SDS-PAGE and autoradiography. For double immunoprecipitation of phosphorylated STRAP, the immune complexes from the first immunoprecipitations were eluted by boiling for 3 min in SDS sample buffer and the eluants were diluted 20 fold by lysis buffer for the second immunoprecipitation. The immunoprecipitates were washed thoroughly with wash buffer containing 0.1% sodium deoxycholate and then analyzed by SDS-PAGE. Quantitation of STRAP phosphorylation was performed using IMAGEOUANT® software (Molecular Dynamics, Inc., Sunnyvale, Calif.).

In vitro kinase assays. Fun length STRAP, Smad2, and the cytoplasmic domain of TβR-I and TβR-I(TD) fused to GST were overexpressed in E. coli by induction with 0.4 mM IPTG for 6 hr. After sonication, the GST fusion proteins were collected on glutathione-agarose beads (Sigma Chemical Company, St. Louis, Mo.), washed extensively, eluted in buffer containing 20 mM reduced glutathione and dialysed. GST-STRAP was cleaved by thrombin (Pharmacia Biosystems Aktiebolaget, Uppsala, Sweden) according to manufacturer's instructions. 2 µg of either GST, GST-STRAP, GST-Smad2 or STRAP (as substrate) was incubated with 0.5 µg of GST-TβR-I fusion proteins (as kinase) in 30 µl of kinase buffer (50 mM Tris, pH 7.5, 100 mM NaCl, 10 mM MgCl$_2$, 1 mM dithiothreitol, 0.05% Triton-X 100, and 10 nM Microcystin) containing 2 µM ATP and 15 µCi[γ-$^{32}$P] ATP at room temperature for 30 min. Reactions were stopped by addition of SDS sample buffer and protein phosphorylation was analyzed by SDS-PAGE and autoradiography. For phosphorylation by immunoprecipitated kinases, COS1 cells were transfected with the receptor constructs. Overexpressed receptors immunoprecipitated from cell lysates were washed three times with lysis buffer followed by two washes in kinase buffer. These immune complexes were used for kinase assay with GST or GST-STRAP as substrate.

Transcriptional response assays. Mv1Lu or HepG2 cells were transiently transfected with the indicated constructs and pCMV-βgal. Twenty hr after transfection, cells were incubated in appropriate media containing 0.2% FBS with or without 100 pM TGF-β1 for 20 hr. Luciferase activity and β-galactosiadse activity were measured in an Analytical Luminescence Laboratory (Ann Arbor, Mich.) Monolight 2010 Luminometer. Luciferase activity was normalized to β-galactosidase activity for transfection efficiency.

Results

STRAP synergizes with Smad7, not with Smad6, in inhibiting TGF-β-induced transcription. The induction of extracellular matrix protein genes is one of the best characterized responses to TGF-β (Keeton, M. R., et al. (1991) J. Biol. Chem. 266:23048–23052). This response can be used to evaluate the involvement of a gene in TGF-β signal transduction using transient transfection assays. Transcription of a luciferase reporter containing a PAI-I promoter fragment is frequently used to measure the induction of extracellular matrix protein synthesis in response to TGF-β (Keeton, M. R., et al. (1991) J. Biol. Chem. 266:23048–23052).

Figure 5A:
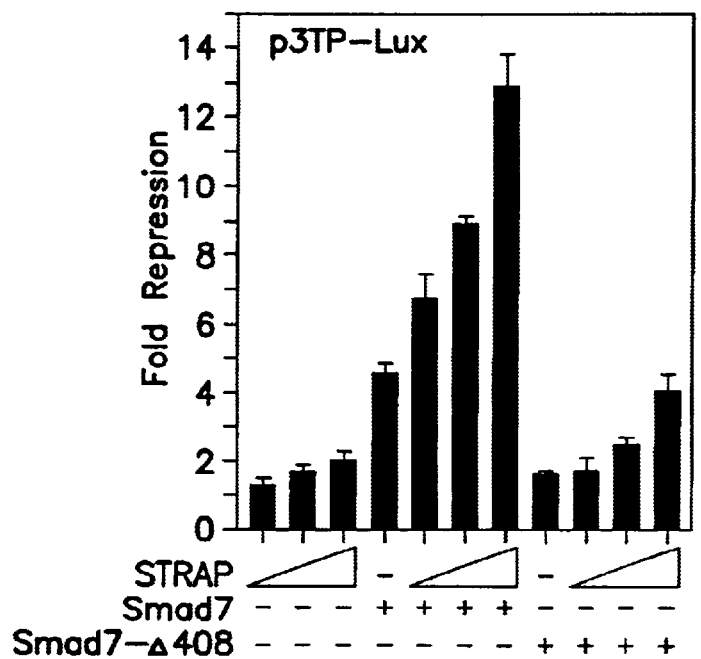
FIG. 5A is a graph showing that STRAP synergizes with Smad7, but not with the mutant, Smad7-Δ408. Mv1Lu cells were transiently transfected with p3TP-Lux (0.3 μg), β-galactosidase reporter (30 ng), TβR-I(TD) (0.43 μg), Smad7 constructs (0.3 μg), and increasing amounts of STRAP (0.2, 0.5 and 1 μg) as indicated. In each experiment equal amounts of total DNA were transfected. Luciferase activity was normalized to β-galactosidase activity. The mean of triplicate luciferase values from the TGF-β treated control was considered as 100% and this was then divided by three replicates of each point to get the fold repressions. The mean of these fold repressions is plotted with ± standard deviation. These experiments were performed four times in triplicate with similar results.

The role of STRAP in Smad7-mediated inhibition of transcriptional responses was evaluated in Mv1Lu and HepG2 cells, which are highly TGF-β responsive. Initially, the analyses focused on a TGF-β-responsive reporter, p3TP-Lux (Wieser, R., et al., EMBO J. 14:2199–2208), which contains elements from the PAI-1 promoter and drives expression of a luciferase reporter gene. Transient transfection of p3TP-Lux into Mv1Lu cells resulted in low basal levels of transcription which was strongly induced in response to TGF-β signaling. Overexpression of STRAP suppressed the TGF-β-induced increase in luciferase activity moderately in a dose-dependent manner. Smad7 showed appreciable inhibition of TGF-β-induced transcription as expected (Hayashi, H., et al. (1997) Cell 89:1165–1173; Souchelnytskyi, S. et al. (1998) J. Biol. Chem. 273:25364–25370). Coexpression of Smad7 and STRAP synergistically inhibited the p3TP promoter activity in response to TGF-β (FIG. 5A). In contrast, only a slight inhibition was observed in the absence of TGF-β signaling.

Figure 5B:
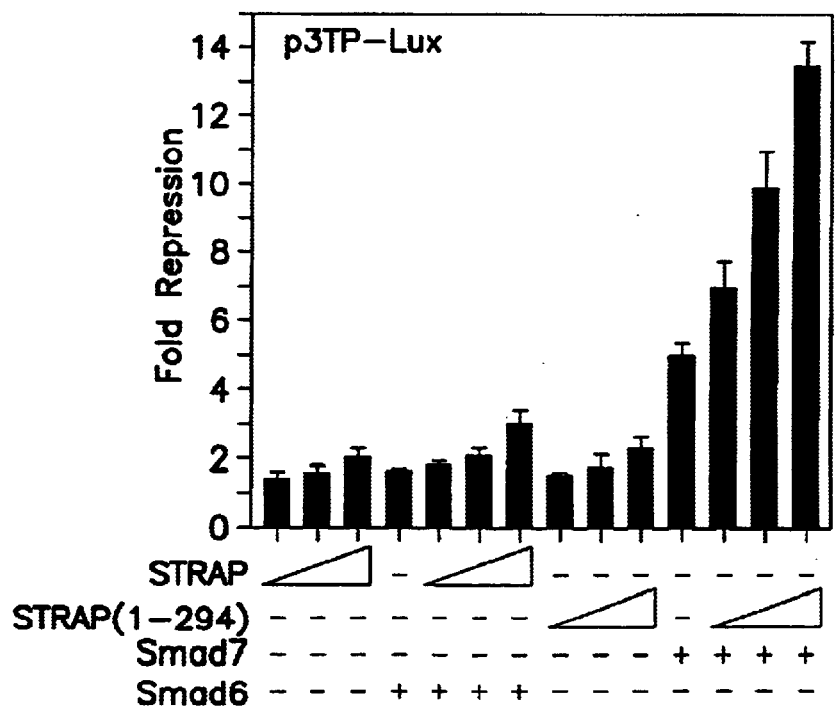
FIG. 5B is a graph showing that STRAP does not synergize with Smad6, but the STRAP(1-294) mutant shows synergy with Smad7. Mv1Lu cells were transfected as above with Smad7 or Smad6 (0.52 μg) and increasing amounts of STRAP(1-294). Luciferase assays were performed as in (A).

To examine whether this synergy in inhibiting TGF-β signals was specific, a mutant of Smad7, Smad7-Δ408, was employed. This mutant can not bind the receptor complex and has little effect in blocking TGF-β signals (Hayashi, H., et al. (1997) Cell 89:1165–1173; Souchelnytskyi, S. et al. (1998) J. Biol. Chem. 273:25364–25370). Consistent with these observations, Smad7-Δ408 had little effect on the p3TP promoter activity, either in the absence or presence of STRAP in response to TGF-β. Importantly, STRAP did not show any synergy with Smad6, an antagonist of BMP signaling (FIG. 5A). A STRAP mutant, STRAP(1-294), was also constructed by deleting C-terminal 57 amino acids and keeping all WD40 domains intact This mutant was not phosphorylated in vivo, whereas STRAP was phosphorylated through its C-terminus mediated by TGF-β receptors. STRAP(1-294) showed the same inhibitory effect as wild-type STRAP, either in absence or presence of Smad7 (FIG. 5B), suggesting that phosphorylation of STRAP is dispensable for this transcriptional response.

Figure 6A:
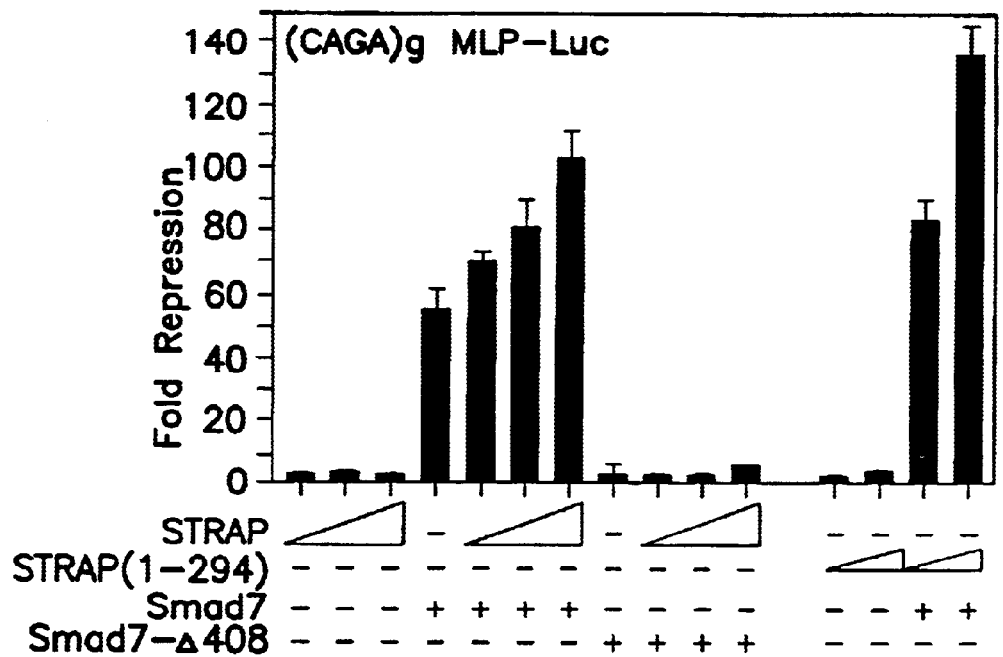
FIG. 6A is a graph showing synergistic inhibition of (CAGA)$_9$-reporter activity in response to TGF-β. HepG2 cells were transfected with a (CAGA)$_9$ MLP-Luc reporter (0.3 μg) containing nine copies of Smad3/Smad4 binding sites, Smad7 constructs, increasing amounts of STRAP, and increasing amounts of STRAP(1-294) (0.5 and 1 μg). TGF-β signaling was initiated by expression of TβR-I(T204D). Luciferase assays were performed as described in FIG. 5A.

To further examine the synergistic inhibition by STRAP and Smad7, another TGF-β-responsive reporter (CAGA)$_9$ MLP-Luc, which contains multiple copies of Smad3/Smad4 binding CAGA box element upstream of a minimal adenovirus major late promoter (Dennier, S., et al. (1998) *EMBO J.* 17:3091–3100), was used. This reporter was induced by 150-fold in response to TGF-β signaling. STRAP alone had little effect on (CAGA)$_9$ MLP promoter activity (FIG. 6A). Smad7 alone showed 57 fold repression of the promoter activity, but in the presence of STRAP it showed a maximum of 105 fold repression in the presence of TGF-β signaling in a dose-dependent manner (FIG. 6A) However, in cells expressing STRAP and Smad7-Δ408, there was no synergy in the inhibition of TGF-β mediated transcriptional activation of the promoter activity. The phosphorylation incompetent mutant of STRAP showed synergy with Smad7 similar to wild type STRAP. These data suggest that STRAP synergistically inhibits TGF-β signaling with Smad7, but not with the Smad7 mutant or Smad6.

Figure 6B:
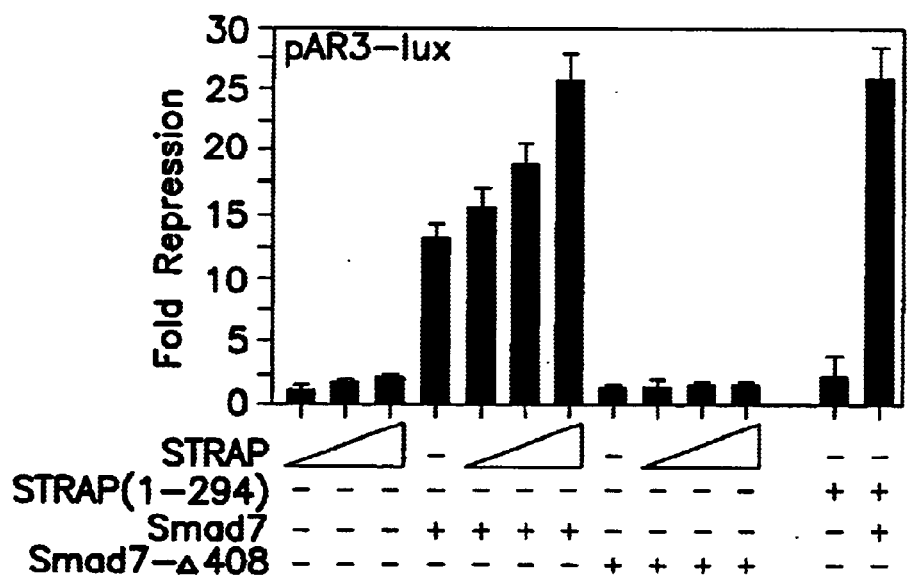
FIG. 6B is a graph showing that STRAP and Smad7 synergistically block an immediate early response to TGF-β. HepG2 cells were co-transfected with pAR3-Lux (0.3 μg), FAST2 (15 ng), Smad7 constructs, STRAP(1-294) (1 μg), and increasing amounts of STRAP as indicated. Cells were treated with or without TGF-β (100 pM) for 20 hr prior to lysis and then analyzed for luciferase activity.

To determine whether this inhibitory effect of STRAP in cooperation with Smad7 was direct in TGF-β signaling, another reporter, pAR3-lux (Hayashi, H., et al. (1997) *Cell* 89:1165–1173) that contains three copies of the activin response element from the Xenopus Mix.2 promoter (Chen, X., et al. (1996) *Nature* 383:691–696), was used. This construct had minimal basal activity in HepG2 cells due to the lack of endogenous FAST-like activity (Henis, Y. I., et al. (1994) *J. Cell Biol.* 126:139–154; Liu, F., et al. (1997) *Genes Dev.* 11:3157–3167). Since activin and TGF-β activate common downstream signaling pathways to regulate common biological processes (Ca¢rcamo, J., et al. (1994) *Mol. Cell Biol.* 14:3810–3821; Kretzschmar, M., and J. Massague ¢ (1998) *Curr. Opin. Genet. Dev.* 8:103–111), this reporter was utilized to investigate STRAP-mediated synergy with Smad7 in blocking immediate early responses to TGF-β.

pAR3-lux was activated approximately 32-fold by FAST2 (Labbe¢, E., et al. (1998) *Mol. Cell* 2:109–120) when transfected HepG2 cells were treated with 100 pM TGF-β. Although STRAP alone had little effect on the promoter activity, it suppressed the TGF-β-dependent activation strongly in concert with Smad7 (FIG. 6B). However, co-expression of STRAP and Smad7-Δ408 did not show any synergy in the inhibition of pAR3-lux transactivation in response to TGF-β. Both amino and carboxy terminal tags were used in Smad7. These tagged versions of Smad7 were same as the untagged protein in blocking TGF-β-dependent signaling (Hayashi, H., et al. (1997) *Cell* 89:1165–1173). Similarly, tagged and untagged versions of STRAP are indistinguishable in inhibitory function.

Figures 6C, 6D:
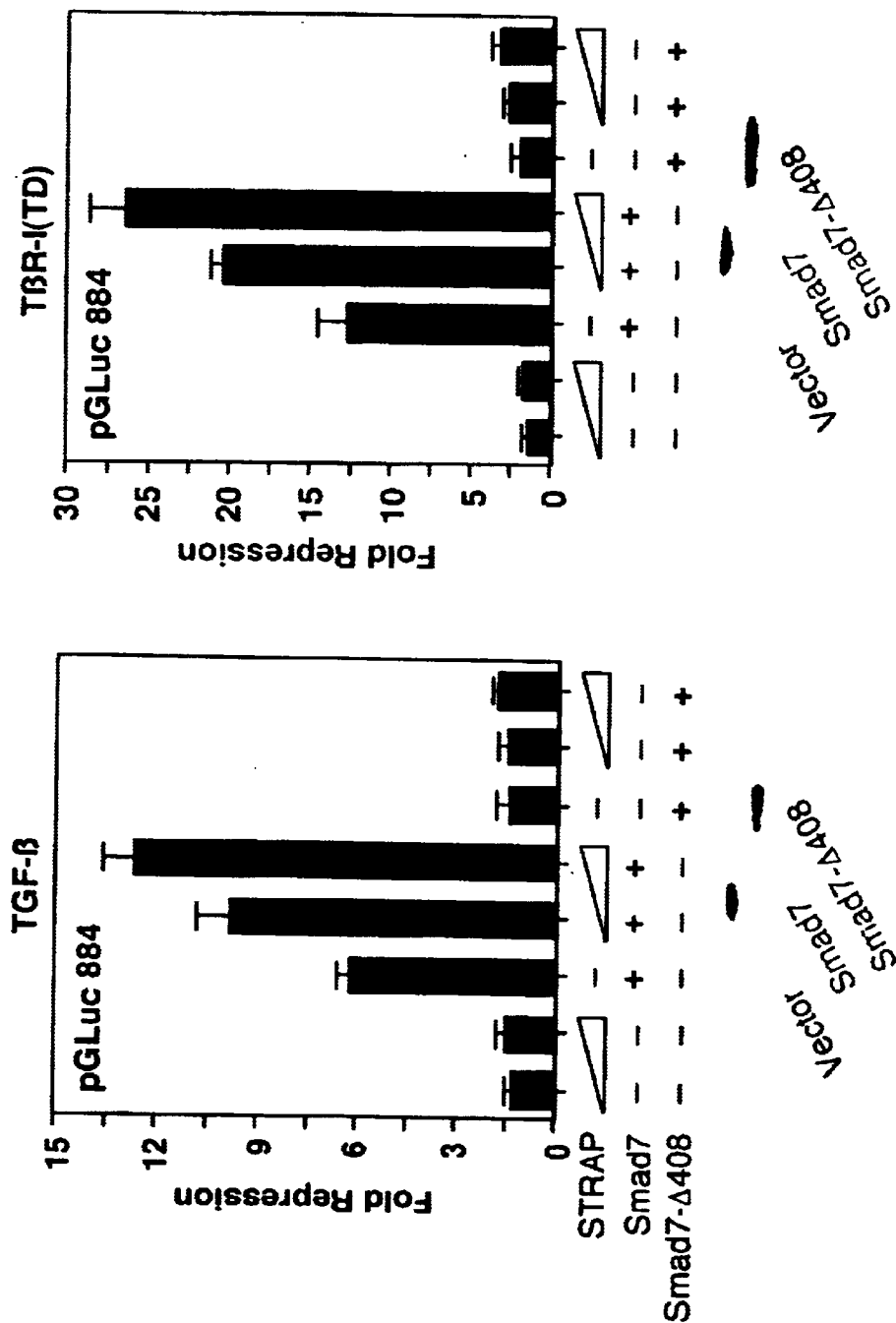
FIG. 6C is a graph showing synergistic inhibition of TGF-β-induced PAI-1 promoter activity by STRAP and Smad7. HepG2 cells were transiently transfected with pGLuc 884 reporter (0.25 μg), HA-tagged Smad7 constructs, and increasing amounts of STRAP. TGF-β signaling was initiated by treatment of the cells with 100 pM TGF-β. Luciferase assays were performed as described in FIG. 5A. Expression of Smad7 proteins were confirmed by direct immunoblotting of total cell lysates, made for luciferase assays from cells transfected with either vector, Smad7, or Smad7-408 construct, with anti-HA antibodies.
FIG. 6D is a graph showing synergistic inhibition of TGF-β-induced PAI-1 promoter activity by STRAP and Smad7. HepG2 cells were transiently transfected with pGLuc 884 reporter (0.25 µg), HA-tagged Smad7 constructs, and increasing amounts of STRAP. TGF-β signaling was initiated by co-expression with TβR-I(TD). Luciferase assays were performed as described in FIG. 5A. Expression of Smad7 proteins were confirmed by direct immunoblotting of total cell lysates, made for luciferase assays from cells transfected with either vector, Smad7, or Smad7- 408 construct, with anti-HA antibodies.

To investigate whether STRAP has a similar effect on a natural promoter, transient transfection assays were performed with a reporter plasmid (pGLuc 834)(Chen, Y-Q, et al. (1998) *J. Biol. Chem.* 273:8225–8231) containing the luciferase gene under the control of the TGF-β-inducible PAI-1 gene promoter. This reporter was strongly induced in HepG2 cells in response to TGF-β signaling initiated either by treatment of the cells with 100 pM TGF-β (FIG. 6C) or by co-expression with a constitutively active version of TGF-β type I receptor, TβR-I(TD) (FIG. 6D). A weak suppression of TGF-β dependent induction of the PAI-1 promoter by STRAP was observed. STRAP showed a synergy in the inhibition of PAI-1 promoter with wild-type Smad7, but not with the mutant. Smad7-Δ408 (FIG. 6C). Taken together, these results show a functional synergy between STRAP and Smad7 in the negative regulation of transcription mediated by TGF-β, and a mutant of Smad7 that fails to associate with the receptor does not synergize with STRAP.

Figure 7A:
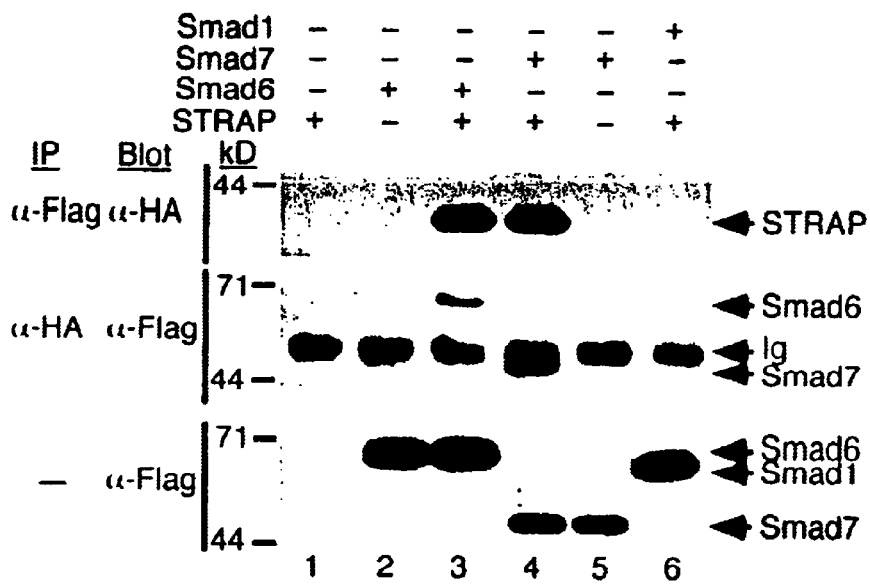
FIG. 7A is an autoradiograph of a protein gel depicting association of STRAP with Smad7, but not with Smad7-Δ408, and oligomerization of STRAP. (A) Interaction of STRAP with Smad6 and Smad7 in mammalian cells. COS-1 cells were transfected with HA-tagged STRAP either alone or together with the indicated Flag-tagged Smad constructs, including Smad1(AAVA), Smad6, and Smad7. Cell lysates were subjected to an anti-Flag immunoprecipitation (IP), and coprecipitating STRAP was detected by immunoblotting (Blot) with anti-HA antibodies (first panel). In the second panel, total lysates were immunoprecipitated using anti-HA antibodies and then immunoblotted with anti-Flag antibodies. To confirm expression of Smads, aliquots of total cell lysates were immunoblotted with anti-Fag antibodies (third panel).

STRAP interacts with Smad6 and Smad7. Smad6 and Smad7 are known to be intracellular antagonists of signaling by TGF-β family members. To explore the mechanism by which STRAP is exhibiting the synergistic inhibition of TGF-β signaling with Smad7, whether STRAP could interact with the inhibitory Smads was tested using co-immunoprecipitation and immunoblot analyses. STRAP-HA was transiently transfected into COS-1 cells alone or in combination with Flag-tagged Smads. STRAP was detected specifically in the immune complex of either Smad7 or Smad6 (FIG. 7A, first panel, lanes 3 and 4). In a reciprocal experiment, it was observed that Smad7 or Smad6 coimmunoprecipitated with STRAP (FIG. 7A, second panel) demonstrating the association of STRAP with Smad7 or Smad6, any physical association of STRAP with Smad1(AAVA) was not detected. (lane 6). Under similar conditions, STRAP can bind with Smad2 and Smad3, but not with Smad4.

Figure 7B:
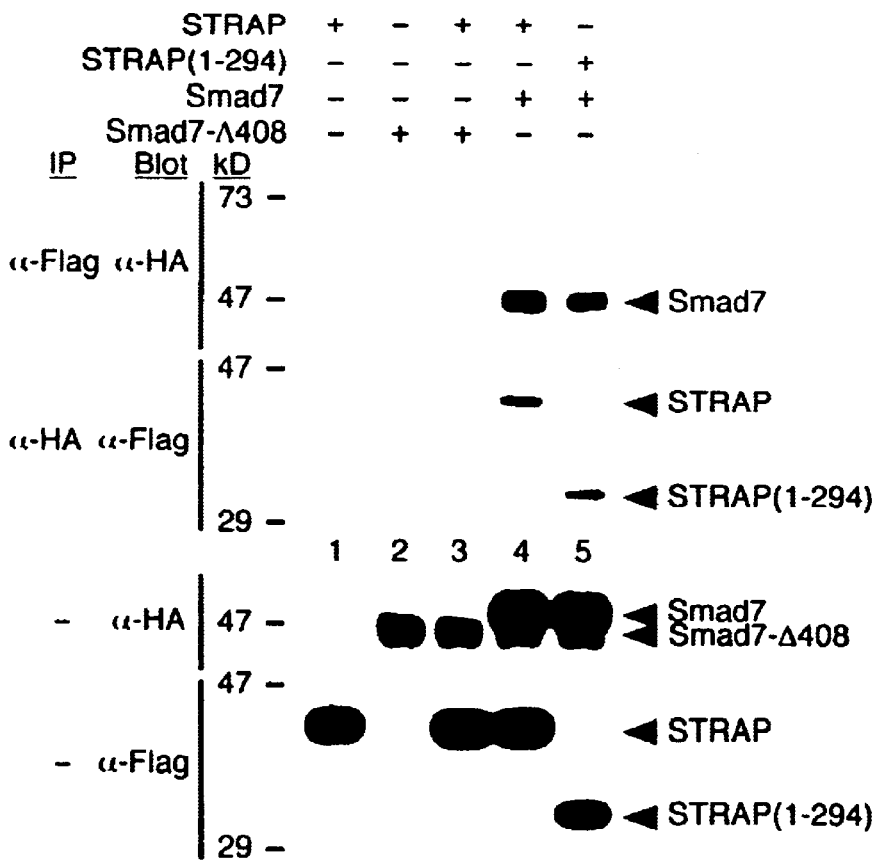
FIG. 7B is an autoradiograph of a protein gel depicting that STRAP(1-294) interacts with Smad7, and Smad7-Δ408 does not interact with STRAP. COS1 cells were transiently transfected with the indicated combinations of Flag-tagged STRAP constructs and HA-tagged Smad7 constructs. Cell lysates were immunoprecipitated with anti-Flag antibody and the immunoprecipitates were analyzed by anti-HA antibody immunoblotting (first panel). In the second panel, cell lysates were subjected to immunoprecipitation with anti-HA antibody and the precipitates were analyzed by anti-Flag antibody. Expression of the proteins was confirmed by the direct immunoblotting of the total cell lysates (third and fourth panel).

STRAP showed functional synergy with Smad7 and not with the mutant of Smad7, Smad7-Δ408 in the inhibition of TGF-β-dependent transcription (FIGS. 5A, 6A, 6B, 6C). To examine whether this truncation in Smad7 has any effect in the association with STRAP, HA-tagged Smad7-Δ408 was co-expressed with Flag-tagged STRAP in COS-1 cells. Cell lysates were then subjected to immunoprecipitation with an anti-Flag antibody and the immunoprecipitates were analyzed by immunoblotting with an anti-HA antibody (FIG. 7B, first panel) and vice versa (second panel). A very low level of interaction between STRAP and Smad7-Δ408 could be detected. This supports the specificity of the interaction between STRAP and Smad7.

On the other hand, Smad7 was detected in the immune complex of STRAP(1-294) and this was co-immunoprecipitated with Smad7 (FIG. 7B, lane 5), indicating that the association of STRAP with Smad7 was not affected by deleting the C-terminal 57 amino acids from STRAP. These findings were consistent with the observation that STRAP does not synergize with Smad7-Δ408 and STRAP(1-294) behaves like wild type STRAP in the transcriptional responses. Both Flag- and HA-tagged STRAP and Smad7 were used in the co-immunoprecipitation experiments, demonstrating that the association was independent of the epitope tag employed and the amino or carboxy terminal tags did not alter the association of the proteins. Together, these data indicate that STRAP interacts with Smad6 and Smad7, but not with the mutant of Smad7, and C-terminal deletion of STRAP does not affect its association with Smad7.

Thus, the interaction of STRAP with Smad6 and Smad7 in mammalian cells is demonstrated. COS-1 cells were transfected with HA-tagged STRAP either alone or together with the indicated Flag-tagged Smad constructs, including Smad1(AAVA), Smad6, and Smad7. Cell lysates were subjected to an anti-Flag immunoprecipitation (IP), and coprecipitating STRAP was detected by immunoblotting (Blot) with anti-HA antibodies. Total lysates were immunoprecipitated using anti-HA antibodies and then immunoblotted with anti-Flag antibodies. To confirm expression of Smads, aliquots of total cell lysates were immunoblotted with anti-Flag antibodies.

STRAP(1-294) interacts with Smad7, and Smad7-Δ408 does not interact with STRAP. COS-1 cells were transiently transfected with the indicated combinations of Flag-tagged STRAP constructs and HA-tagged Smad7 constructs. Cell lysates were immunoprecipitated with anti-Flag antibody and the immunoprecipitates were analyzed by anti-HA antibody immunoblotting. Cell lysates were then subjected to immunoprecipitation with anti-HA antibody and the precipitates were analyzed by anti-Flag antibody. Expression of the proteins was confirmed by the direct immunoblotting of the total cell lysates.

Homo-oligomerization of STRAP. Several components of the TGF-β signaling cascade, including receptors and Smad proteins, are known to homo- and hetero-oligomerize (Chen, R.-H. and R. Derynck (1994) *J. Biol. Chem.* 269:22868–22874; Henis, Y. I., et al. (1994) *J. Cell Biol.* 126:139–154; Kawabata, M. et al. (1998) *EMBO J.* 17:4056–4065; Lagna, G. et al. (1996) *Nature* 383:832–836; Yamashita, H., et al. (1994) *J. Biol. Chem.* 269:20172–20178). WD40 repeat proteins homo- and hetero-oligomerize presumably to stabilize their structure and to serve regulatory functions in various cellular processes (Near, E. J., et al. (1994) *Nature* 371:297–300). As described above, STRAP has six WD40 domains.

Figure 7C:
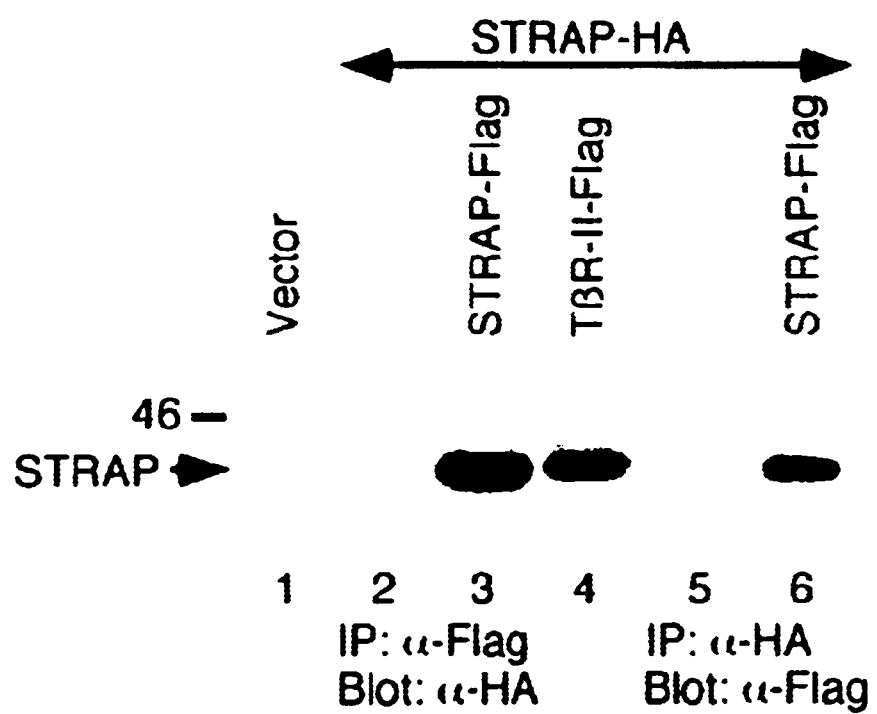
FIG. 7C is an autoradiograph of a protein gel depicting homo-oligomerization of STRAP. Cells were transfected with STRAP-HA alone or together with STRAP-Flag or TβR-II-Flag (serves as positive control) as indicated. Cell lysates were subjected to immunoprecipitation with a Flag antibody and coprecipitated proteins were detected by immunoblotting with HA antibody (lanes 1–4). Reciprocal experiments were also performed (lanes 5 and 6).

To determine whether it can form homo-oligomers, COS-1 cells were co-transfected with two different STRAP constructs, one tagged with Flag epitope and the other tagged with HA epitope. Cell lysates were subjected to immunoprecipitation with antibodies to Flag, and each immunoprecipitate was then probed with antibodies to HA (FIG. 7C, lanes, 1–4). Reciprocal experiments in which proteins immunoprecipitated by antibodies to HA were blotted with an anti-Flag antibody (FIG. 7C, lanes 5, 6) confirmed the association of STRAP with itself in a ligand-independent manner. As described in Examples 1–3 above, STRAP was detected in the immunecomplex of TβR-II under similar conditions (lane 4). This illustrates that different epitope tags do not affect the homo-oligomerization and the overall tertiary structure of STRAP.

The homo-oligomerization of STRAP has thus been demonstrated. Cells were transfected with STRAP-HA alone or together with STRAP-Flag or TβR-II-Flag (serves as positive control). Cell lysates were subjected to immunoprecipitation with a Flag antibody and co-precipitated proteins were detected by immunoblotting with HA antibody. Reciprocal experiments were also performed.

STRAP stabilizes the complex between Smad7 and activated type I TGF-β receptor, Smad7 blocks TGF-β signaling by preventing heteromeric complex formation between Smad2 or Smad3 and Smad4 and nuclear accumulation of Smad2 or Smad3 in response to TGF-β signaling (Hayashi, H., et al. (1997) *Cell* 89:1165–1173; Nakao, A., et al. (1 997) *Nature* 389:631–635) Smad7 is also known to block BMP signaling by inhibiting the phosphorylation of Smad1 and Smad5 (Souchelnytskyi, S., et al. (1998) *J. Biol. Chem.* 273:25364–25370). Smad6 has been shown to inhibit BMP signaling by distinct mechanism (Hata, A. et al. (1998) *Genes Dev.* 12:186–197). It prevents formation of an active Smad4/Smad1 signaling complex by directly competing with Smad4 for binding to Smad1. The mechanism of inhibition is not well known, although it seems to be primarily mediated through the ability of Smad6 and Smad7 to interact with the type I receptor. Smad7 functions by associating stably with the activated type I receptor to block the interaction, phosphorylation and subsequent activation of Smad2 and Smad3 (Hayashi, H., et al. (1997) *Cell* 89:1165–1173; Nakao, A., et al. (1997) *Nature* 389:631–635) Therefore, stable association of Smad7 with the type I receptor plays a role in blocking TGF-β family signaling.

Figure 8A:
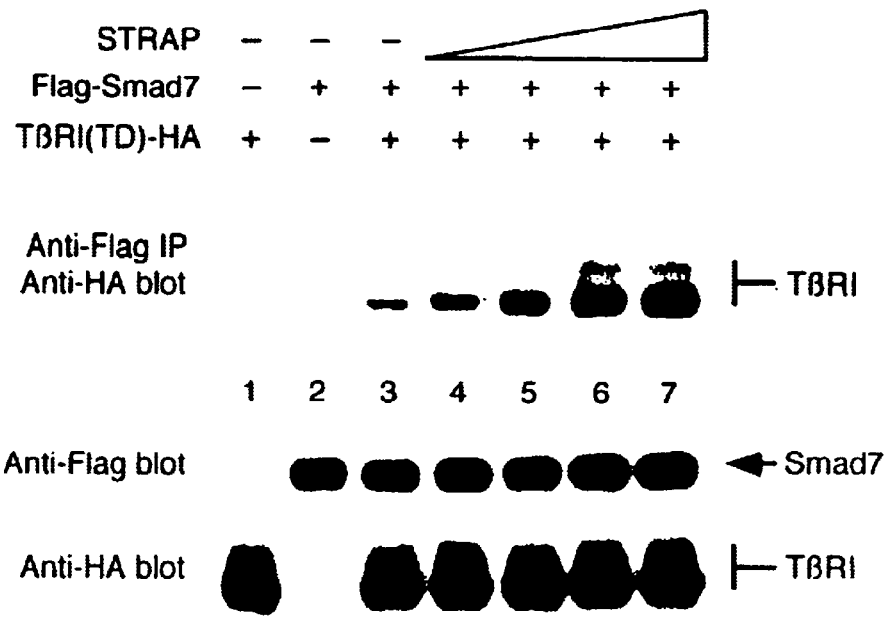
FIG. 8A is an autoradiograph of a protein gel depicting that STRAP stabilizes the association between Smad7 and activated TβR-I and that STRAP stabilizes Smad7-TβR-I (TD) complexes. COS-1 cells were transiently transfected with the following plasmids as indicated: Flag-Smad7 (0.4 µg), TβR-I(TD)-HA (0.6 µg), and increasing amounts of STRAP (0.2,0,4, 1, and 2 µg). Cell lysates were subjected to immunoprecipitation with anti-Flag antibody and the presence of TβR-I(TD) in the immunoprecipitates was detected by immunoblotting with anti-HA antibody (first panel). To confirm equivalent expression of Smad7 and TβR-I(TD), aliquots of total cell lysates were immunoblotted with anti-Flag antibody (second panel) and anti-HA antibody (third panel).

To explore the mechanism of STRAP function in the synergistic inhibition of TGF-β signaling, whether STRAP could stabilize the complex between Smad7 and activated TβR-I was evaluated. COS-1 cells were transiently transfected with Flag-Smad7, TβR-I(TD)-HA and increasing amounts of STRAP as described above. Cell lysates were subjected to immunoprecipitation with antibodies to Rag followed by immunoblotting with anti-HA antibodies. In cells expressing Smad7 and TβR-I(TD), association between these two proteins was detected, similar to previous observations (FIG. 8A, lane 3) (Hayashi, H., et al. (1997) *Cell* 89:1165–1173). Interestingly. Smad7/TβR-I heteromeric complex formation was increased strongly with increasing amounts of STRAP in a dose-dependent manner in the presence of TGF-β signals (lanes 4–7). A pronounced stimulation of Smad7/TβR-I(TD) interaction was observed when the STRAP-Smad7 concentration ratio was less than one or one (lanes 4, 5). Similarly, Smad7 increases the interaction between STRAP and TβR-I(TD). Together, these data demonstrate that STRAP associates stably with Smad7 and it stabilizes complexes between Smad7 and TβR-I in the presence of TGF-β signaling.

Thus, an autoradiograph of a protein gel was prepared (FIG. 8A), and it depicted that STRAP stabilizes the association between Smad7 and activated TβR-I and that STRAP stabilizes Smad7-TβR-I(TD) complexes. COS-1 cells were transiently transfected with the following plasmids as indicated: Flag-Smad7 (0.4 μg), TβR-I(TD)-HA (0.6 μg), and increasing amounts of STRAP (0.2, 0.4, 1, and 2 μg). Cell lysates were subjected to immunoprecipitation with anti-Flag antibody and the presence of TβR-I(TD) in the immunoprecipitates was detected by immunoblotting with anti-HA antibody. To confirm equivalent expression of Smad7 and TβR-I(TD), aliquots of total cell lysates were immunobloted with anti-Flag antibody and anti-HA antibody.

Figure 8B:
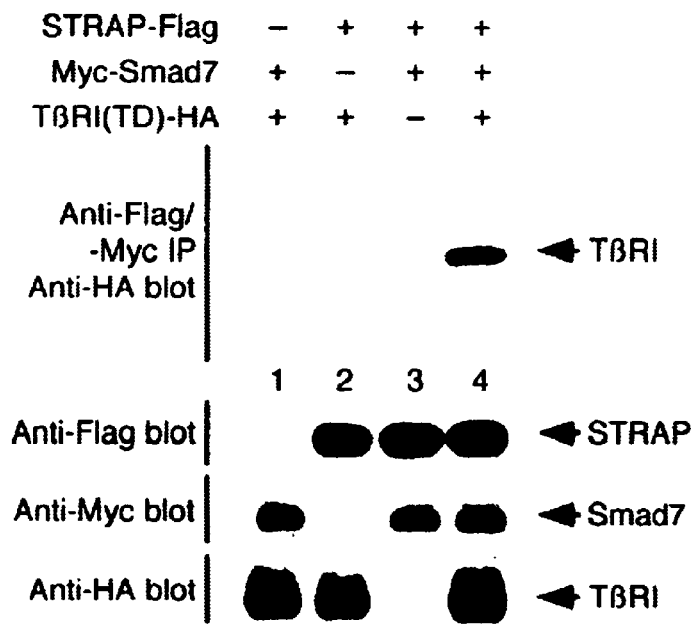
FIG. 8B is an autoradiograph of a protein gel depicting that STRAP is present in an inhibitory complex with Smad7 and TβR-I(TD). Cells were transfected with indicated combinations STRAP-Flag, Myc-Smad7, and TβR-I(TD)-HA. Cell lysates were immunoprecipitated with anti-Flag antibody, proteins were eluted with Flag peptide, and the eluate repreciptated by anti-Myc antibody followed by anti-HA antibody immunoblotting (first panel). Expression of the proteins was monitored by immunoblotting.

STRAP forms a temary complex with Smad7 and TβR-I(TD). The data presented above shows that STRAP binds to Smad7 as well as the interaction between STRAP and the receptor complex. To determine whether these components were present in the same inhibitory complex, COS-1 cells were cotransfected with Flag tagged STRAP, HA tagged TβR-I(TD) and Myc tagged Smad7. Cell lysates were subjected to immunoprecipitation with anti-Flag antibody. Immune complexes were then eluted with Flag peptide and the eluate was used in the second immunoprecipitation with anti-Myc antibody. Finally, the immunoprecipitate was analyzed by immunoblotting with anti-HA antibody. According to FIG. 8B, a ternary complex was detected when cells were cotransfected with all three constructs, but not when any one construct was omitted. Thus, both STRAP and Smad7 can coexist in the same receptor containing complex. Taken together, these results suggest that STRAP functions to recruit Smad7 to the activated receptor forming a ternary complex and to stabilize Smad7-receptor complex, thus assisting Smad7 to prevent Smad2/Smad3 access to the receptor.

Thus, an autoradiograph of a protein gel was prepared (FIG. 8B), and it depicted that STRAP is present in an inhibitory complex with Smad7 and TβR-I(TD). Cells were transfected with indicated combinations STRAP-Flag, Myc-Smad7, and TβR-I(TD)-HA. Cell lysates were immunoprecipitated with anti-Flag antibody, proteins were eluted with Flag peptide, and the eluate re-precipitated by anti-Myc antibody followed by anti-HA antibody immunoblotting. Expression of the proteins was monitored by immunoblotting.

Phosphorylation of STRAP in vivo requires its C-terminus. For downstream signaling from receptor kinases to culminate in transcriptional regulation of target genes, the phosphorylation of some signaling components is often essential. To test whether STRAP is a substrate for the serine/threonine kinase receptors, the phosphorylation of STRAP in vivo was analyzed in COS-1 cells where it was coexpressed with different combinations of TGF-β receptors. Metabolic labeling of transfected cells with $^{32}$P-orthophosphate followed by immunoprecipitation of STRAP with anti-Flag antibody indicated a low basal level of STRAP phosphorylation in COS-1 cells without exogenous receptor expression (FIG. 4A, lane 1). An increase in STRAP phosphorylation was detected in cells expressing TβR-I (lane 2). This increase was dependent on TβR-I kinase activity because a point mutation (K232R), that abolishes TβR-I kinase activity prevented the increase in STRAP phosphorylation (lane 3).

Co-expression of STRAP with TβR-II resulted in a significant increase in STRAP phosphorylation (lane 4), but a kinase inactive mutant (K277R) was unable to induce the phosphorylation of STRAP (lane 5). It is possible that type I receptor was mediating the enhancement of STRAP phosphorylation in vivo and in lane 4 the over-expressed type II receptor was increasing STRAP phosphorylation through low levels of endogenous type I receptor (Hayashi, H., et al. (1997) *Cell* 89:1165–1173; Labbeć, E., et al. (1998) *Mol. Cell* 2:109–120). A further increase in the phosphorylation of STRAP was observed in cells expressing both TβR-I and TβR-II (lane 6) and the kinase activity of both was required for this increase (lane 7). Deletion of the C-terminal 57 amino acids of STRAP abolished both its basal and receptor-induced phosphorylation (lanes 8, 9), indicating that the C-terminus of STRAP is required for its phosphorylation. Double immunoprecipitation from $^{32}$P-orthophosphate labeled cells with anti-Flag antibody confirmed the identity of phosphorylated STRAP as the 40 kD band (FIG. 4B). At least two other phosphoproteins were detected in the STRAP immunoprecipitates, and not in the STRAP(1-294) immunoprecipitates.

A low level of phosphorylation of STRAP was also observed in R1B/L17 mink lung epithelial cells deficient in TβR-I. STRAP phosphorylation in these cells was stimulated when TβR-I was coexpressed with STRAP. Finally, whether STRAP phosphorylation could be regulated by TGF-β was evaluated. Only marginal increase in STRAP phosphorylation in transfected Mv1Lu cells was observed when eels were stimulated by TGF-β. These data suggest that the increase in STRAP phosphorylation in vivo can be mediated by either TGF-β receptors, a receptor associated kinase or a STRAP associated kinase that is activated by TGF-β receptors in a multimeric complex.

Influence of Smad7 in the phosphorylation of STRAP. Since Smad7 can associate with active TGF-β receptor complexes and inhibit the phosphorylation of Smad2/Smad3 (Hayashi, H., et al. (1997) *Cell* 89:1165–1173; Nakao, A., et al. (1997) *Nature* 389:631–635), it is possible that Smad7 can also regulate the phosphorylation of STRAP when they are in a complex. This assertion was tested via co-expression of STRAP and Smad7 with or without TβR-I and TβR-II and analyzed the in vivo $^{32}$P-phosphorylation level of STRAP. Kinase activities of the receptors are necessary for the stimulation of STRAP phosphorylation (FIG. 9A, lanes 2, 3) as shown above. In the presence of Smad7, little increase in STRAP phosphorylation was observed (lane 4), but in concert with the TGF-β receptors, Smad7 strongly stimulated the phosphorylation of STRAP (lane 5). This is consistent with the observation that Smad7 stabilizes the STRAP-receptor interaction. Thus, Smad7 potently stimulates the phosphorylation of STRAP mediated by TGF-β receptors.

STRAP expression does not affect receptor phosphorylation. STRAP binds with the receptor complex as shown in Examples 1–3 above and its phosphorylation is regulated by receptors. Whether STRAP might alter the phosphorylation state of the receptors in the presence of TGF-β signaling was investigate via co-expression of TβR-I and TβR-II with or without STRAP in COS-1 cells. Cells were metabolically labeled with $^{32}$P-orthophosphate and stimulated by TGF-β. Phosphorylation of receptors was assessed after immunoprecipitation. The level of phosphorylation of TβR-I or TβR-II, however, was not detectably altered with STRAP expression (FIG. 9B), although the expression level of two receptors was different Therefore, association of STRAP with the receptors does not affect overall receptor phosphorylation.

Figure 9A:
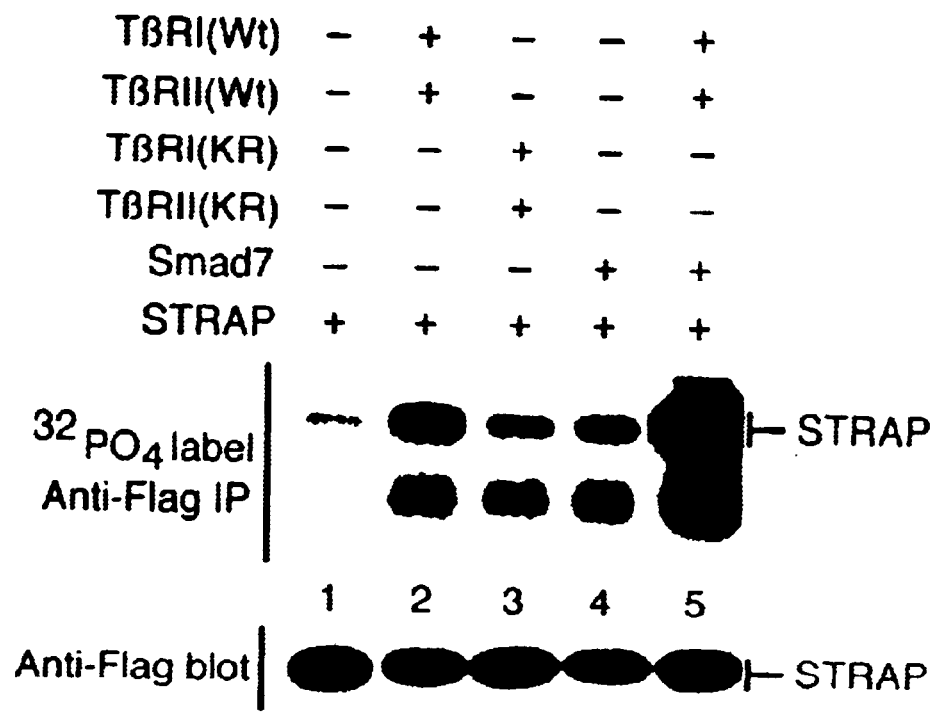
FIG. 9A is an autoradiograph of a protein gel depicting that Smad7 induces receptor-dependent phosphorylation of STRAP. Cells were transfected with the indicated combinations of STRAP, Smad7, and wild type (Wt) and kinase-negative (KR) versions of receptors. After labeling with $^{32}$P-orthophosphate, STRAP-Flag was immunoprecipitated and detected by SDS-PAGE and autoradiography (first panel). Expression of STRAP was monitored by immunoblotting total cell lysates (second panel).

An autoradiograph of a protein gel depicting that Smad7 induces receptor-dependent phosphorylation of STRAP was thus prepared. (FIG. 9A). Cells were transfected with the indicated combinations of STRAP, Smad7, and wild type (Wt) and kinase-negative (KR) versions of receptors. After labeling wit $^{32}$P-orthophosphate, STRAP-Flag was immunoprecipitated and detected by SDS-PAGE and autoradiography. Expression of STRAP was monitored by immunoblotting total cell lysates.

Figure 9B:
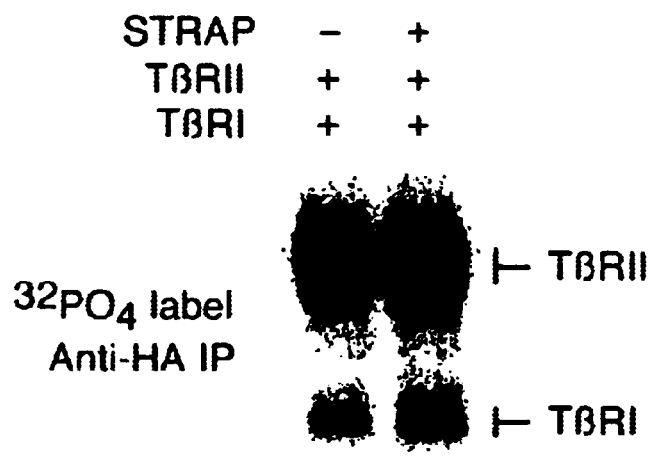
FIG. 9B is an autoradiograph of a protein gel depicting that over-expression of STRAP does not change receptor phosphorylation. Cells were transfected with HA-tagged receptors and STRAP as indicated, metabolically labeled with $^{32}$P-orthophosphate, and stimulated by TGF-β for 20 min. Equal amounts of lysates were immunoprecipitated with anti-HA antibody and receptors were detected by SDS-PAGE followed by autoradiography.

An autoradiograph of a protein gel depicting that overexpression of STRAP does not change receptor phosphorylation was also prepared (FIG. 9B). Cells were transfected with HA-tagged receptors and STRAP as indicated, metabolically labeled with $^{32}$P-orthophosphate, and stimulated by TGF-β for 20 min. Equal amounts of lysates were immunoprecipitated with anti-HA antibody and receptors were detected by SDS-PAGE followed by autoradiography.

Figure 10A:
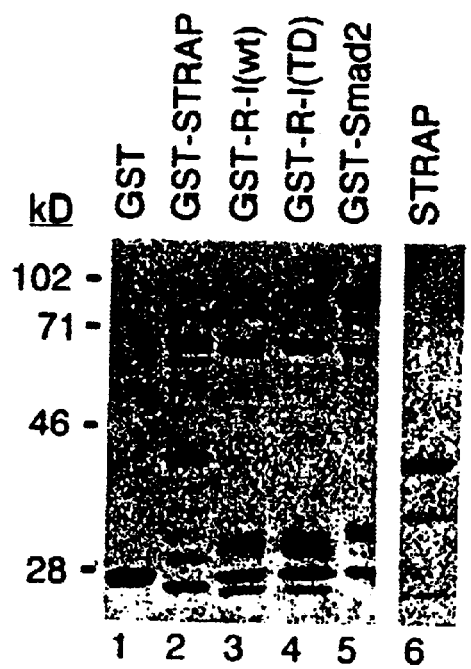
FIG. 10A is an autoradiograph of a protein gel depicting that STRAP is not a direct substrate of the TGF-β receptors in vitro. GST fusions of STRAP, TβR-I(wt), TβR-I(TD), and Smad2 were overexpressed in bacteria, purified, resolved by SDS-PAGE, and visualized by Coomassie Blue staining (lanes 1–5). The STRAP portion was cleaved from the GST-STRAP fusion protein by thrombin and was visualized in lane 6.
Figure 10B:
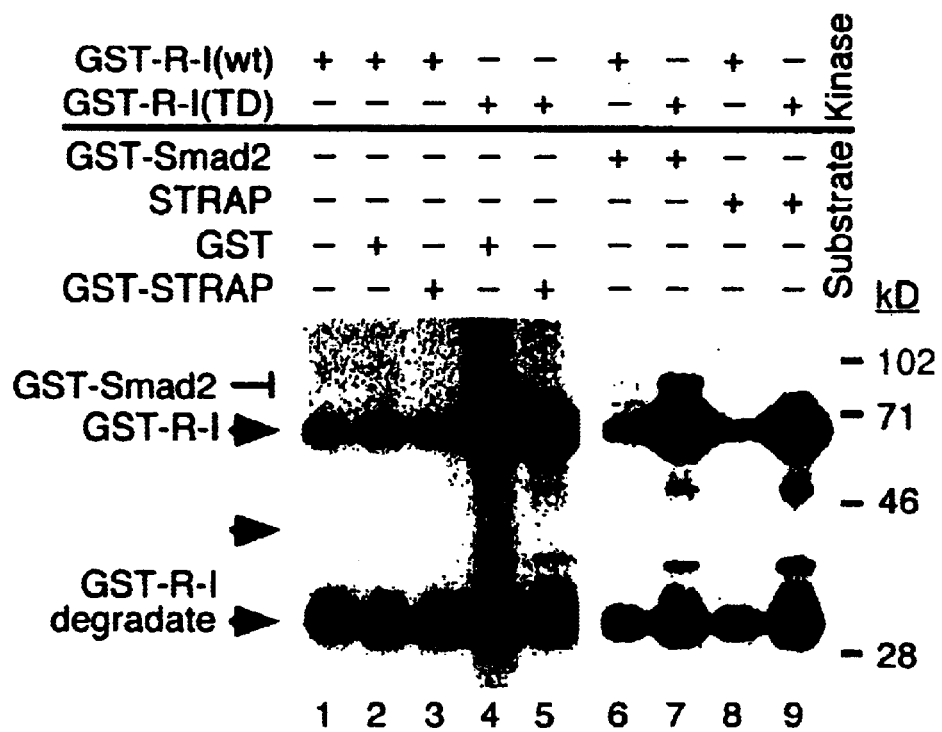
FIG. 10B is an autoradiograph of a protein gel depicting that STRAP is not a direct substrate of the TGF-β receptors in vitro. Equivalent amounts of GST, GST-STRAP, GST-Smad2 (serves as positive control), or STRAP (as substrate) were incubated with either GST-TβR-I(wt) or GST-TβR-I (TD) as indicated in a kinase assay. The fast migrating band is the degradate of the autophophorylated receptor. There was no phosphorylated band in the arrow-head position indicating that STRAP (cleaved from GST-STRAP) was not phosphorylated by the receptors in in vitro kinase assay.

TGF-β receptors cannot phosphorylate STRAP directly in vitro. STRAP phosphorylation mediated by the receptors in vivo could be due to other kinases and not due to the receptors directly. Therefore, whether STRAP is a substrate for the kinase activity of TGF-β receptors was evaluated via expression of full length STRAP. Smad2, and cytoplasmic domains of TβR-I(wt) and TβR-I(TD) as glutathione-S-transferase (GST) fusion proteins in bacteria. These products were purified to near-homogeneity (FIG. 10A, lane 1–5). The STRAP portion was cleaved from the GST-STRAP fusion protein by thrombin (FIG. 10A, lane 6). These receptor kinases were incubated with either GST, GST-STRAP, GST-Smad2, or STRAP in a kinase assay. As shown in FIG. 10B, both GST-TβR-I and GST-TβR-I(TD) were auto-phosphorylated but there is no phosphorylated band of either GST or GST-STRAP. The constitutively active mutant of TβR-I, TβR-I(TD) showed elevated level of kinase activity as expected (Wieser, R. et al. (1995) *EMBO J.* 14:2199–2208).

The GST portion of recombinant STRAP should not block its phosphorylation by the receptor because STRAP is phosphorylated on its C-terminus in vivo. Moreover, STRAP, thrombin cleaved product of GST-STRAP, was not phosphorylated by the receptors in this kinase assay (FIG. 10B, lanes 8, 9). Under similar conditions GST-Smad2 was phosphorylated by the receptors (lanes 6, 7). The fast migrating band was a degradation product of TβR-I as shown previously (Kawabata, M. et al. (1995) *J. Biol Chem.* 270:29628–29631).

It is possible that bacterially expressed receptor kinases were not properly modified post-translationally or the GST portion of the receptor kinases might hinder this phosphorylation. Therefore, TβR-I and TβR-II were over-expressed in COS-1 cells either separately or together. The receptors, individually (FIG. 10C, lanes 14) or in complex (lanes 5, 6), were immunoprecipitated and were subjected to kinase assay with either GST or GST-STRAP as substrate. TβR-I and TβR-II showed auto-phosphorylation, but we did not see any indication of STRAP phosphorylation. Together, these data suggest that STRAP is not a direct substrate of the receptors, and that TGF-β receptors induce STRAP phosphorylation in vivo via a kinase.

Thus, an autoradiograph of a protein gel was prepared (FIG. 10A), and it depicted that STRAP is not a direct substrate of the TGF-β receptors in vitro. GST fusions of STRAP, TβR-I (wt), TβR-I(TD), and Smad2 were overexpressed in bacteria, purified, resolved by SDS-PAGE, and visualized by Coomassie Blue staining. The STRAP portion was cleaved from the GST-STRAP fusion protein by thrombin and was visualized in lane.

An autoradiograph of a protein gel that included equivalent amounts of GST. GST-STRAP, GST-Smad2 (serves as positive control), or STRAP (as substrate) incubated with either GST-TβR-I(wt) or GST-TβR-I(TD) in a kinase assay was also prepared (FIG. 10B). The fast migrating band is the degradate of the autophophorylated receptor. There was no phosphorylated band in the arrowhead position indicating that STRAP (cleaved from GST-STRAP) was not phosphorylated by th receptors in in vitro kinase assay.

Figure 10C:
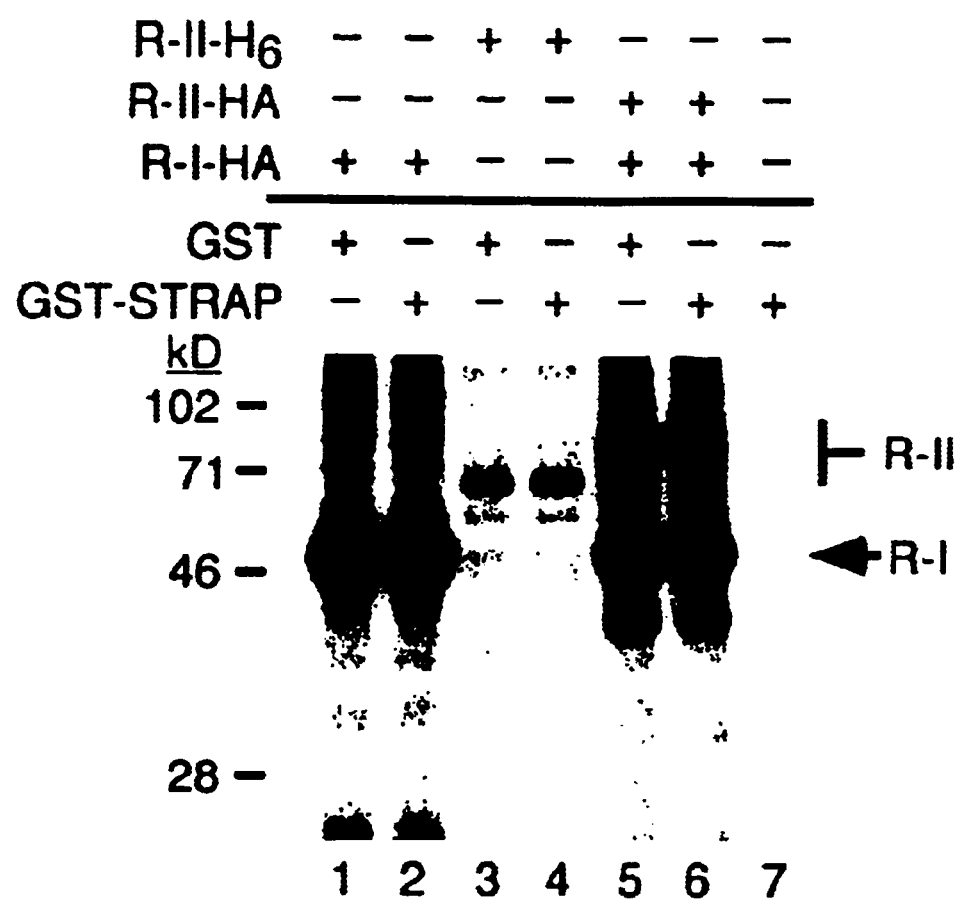
FIG. 10C is an autoradiograph of a protein gel depicting that STRAP is not a direct substrate of the TGF-β receptors in vitro. Similar kinase reactions were carried out using full length, tagged TGF-β receptors, immunoprecipitated from overexpressing COS-1 cells, as kinase and GST or GST-STRAP as substrate. For immunoprecipitation, anti-HA antibody was used for HA-tagged receptors and anti-TβR-II antibody (C16. Santa Cruz Biotechnology. Inc., Santa Cruz, Calif.) was used for hexahistidine-tagged type II receptor. The autophosphorylated receptor bands are indicated.

An autoradiograph of a protein gel depicting similar kinase reactions using full length, tagged TGF-β receptors, immunoprecipitated from overexpressing COS1 cells, as kinase and GST or GST-STRAP as substrate, was also prepared (FIG. 10C). For immunoprecipitation, anti-HA antibody was used for HA-tagged receptors and anti-TβR-II antibody (C16, Santa Cruz Biotechnology. Inc., Santa Cruz. Calif.)was used for hexahistidine-tagged type II receptor. The autophophorylated receptor bands are indicated.

Discussion

TGF-β family members initiate their cellular actions by binding to a heteromeric complex of type I and type II serine/threonine kinase receptors. The multi-functional nature of this family of ligands clearly implicates the need for tight control of their biological activity by positive and negative regulation of signaling (Engel, M. E., et al. (1998) *J. Cell. Blochem.* 30131:111–122; Heldin, C.-H. et al. (1997) *Nature* 390:465–471; Kretzschmar, M., and J. Massague¢ (1998) *Curr. Opin. Genet. Dev.* 8:103–111). Smad protein play a key role in mediating TGF-β signals at the intracellular level. R-Smads are activated by specific activated type I receptors and form heteromeric complex with the common mediator Smad4. A distinct subfamily of Smads, which function to directly inhibit TGF-β family signaling by preventing formation of an active signal-transducing Smad complex, has been identified. Smad7 has been shown to inhibit signaling from TGF-β, activin and BMP by blocking the receptor-mediated activation of R-Smads (Hayashi, H., et al. (1997) *Cell* 89:1165–1173; Nakao, A., et al. (1997) *Nature* 389:631–635,47). Therefore, a stable association between the receptor and Smad7 plays a role in the function as an inhibitor.

A distinct mechanism of action for Smad6 in blocking BMP signals has recently been reported in which Smad6 competes with Smad4 for binding to Smad1 and forms an inactive Smad6-Smad1 complex (Hata, A., at al. (1998) *Genes Dev.* 12:186–197). In Examples 1–3, it is shown that the novel WD40 repeat protein, STRAP, of the present invention associates with both TβR-I and TβR-II and has a role in TGF-β signaling. In Example 4, the molecular mechanism by which STRAP inhibits the transcriptional responses mediated by TGF-β is further characterized. A synergistic relationship between STRAP and Smad7, but not Smad6, in the inhibition of TGF-β-dependent transcription is demonstrated. A mutant of Smad7, Smad7-Δ408 that fails to associate with type I receptor, does not inhibit TGF-β signaling (Hayashi, H., et al. (1997) *Cell* 89:1165–1173). STRAP does not show any cooperation with this mutant of Smad7 demonstrating the specificity in the synergy between Smad7 and STRAP in the inhibition of TGF-β signaling. STRAP forms a ternary complex with Smad7 and the type I receptor in response to TGF-β signaling, and the association between Smad7 and activated type I receptor is stabilized by STRAP.

Functional synergy between STRAP and Smad7 is observed in Example 4. Smad7 has previously been shown to inhibit signal transduction downstream of TGF-β, activin and BMP receptors (Hayashi, H., et al. (1997) *Cell* 89:1165–1173; Souchelnytskyi, S., et al. (1998) *J. Biol. Chem.* 273:25364–25370). Overexpression of STRAP alone has little effect on the repression of TGF-β-induced p3TP-Lux, $(CAGA)_9$ MLP-Luc, pAR3-Lux, and pGLuc 884 reporter activities. Co-expression of STRAP and Smad7 showed a synergistic relationship in the inhibition of these reporter activities in the presence of TGF-β signaling. The fold repression by STRAP and Smad7 acting together is greater than the sum or product of the fold-repressions caused by each protein alone. Importantly, STRAP did not show any synergistic cooperation with a deletion mutant of Smad7, Smad7-Δ408, which has previously been shown not to inhibit TGF-β signaling (Hayashi, H., et al. (1997) *Cell* 89:1165–1173). In contrast, STRAP was inactive in the inhibitory cooperation with Smad6, an antagonist of BMP signaling. This is consistent with both a distinct mechanism of inhibition for Smad6 and its primary role in regulating BMP signals (Hata, A., et al. (1998) *Genes Dev.* 12:186–197; Ishisak, A., et al. 1999 *J. Biol. Chem.* 274:13637–13642). While it is not applicants' desire to be bound by a particular mechanism of operation, these results suggest that the synergistic relationship between STRAP and Smad7 is specific and that STRAP can also inhibit BMP signaling in cooperation with Smad7.

WD40 repeat proteins appear to serve regulatory functions in various cellular processes including cell division, gene transcription, cell-fate determination, signal transduction, mRNA modification and vesicle fusion. These proteins are sometimes stabilized by forming intramolecular dimers or tetramers and some WD40 repeat proteins require all repeats for their stability (Neer, E. J., et al. (1994) *Nature* 371:297–300). STRAP can homo-oligomerize, as assessed by co-immunoprecipitation analyses presented above. Several mutants of STRAP were constructed by deleting one or two WD repeats with or without intervening regions from both N-terminus and C-terminus. Two of them did not express the proteins, three mutants showed ten to fifteen fold less expression when compared with the wild type protein, and the C-terminal mutant, STRAP(1-294) having all the WD40 repeats intact, showed comparable expression of the protein. These results suggest that all WD40 repeats of STRAP might participate in pairwise interactions within the molecule for its stability. This is consistent with the structure and stability of WD40 repeat proteins (Neer, E. J., et al. (1994) *Nature* 371:297–300). STRAP(1-294) exhibited synergistic inhibition of the promoter activities in response to TGF-β signaling, thus resembling the effect of full-length STRAP protein. While it is not applicants' desire to be bound by a particular mechanism of operation, these findings suggest that the functional cooperation between STRAP and Smad7 plays a role in controlling the activity of TGF-β.

STRAP stabilizes the complex between Smad7 and type I receptor. Example 4 demonstrates that STRAP synergizes with Smad7 and not with Smad6 or a mutant of Smad7. Previous studies have shown that Smad7 functions as an inhibitor at a very early step in the TGF-β signaling by associating stably with activated type I receptor to block the interaction and subsequent activation of Smad2 and Smad3 (Hayashi, H., et al. (1997) Cell 89:1165–1173, Nakao, A, et al. (1997) Nature 389:631–635). While it is not applicants' desire to be bound by a particular mechanism of operation, contemplated mechanisms by which such synergy between STRAP and Smad7 is achieved include binding with Smad7 and recruiting it to the receptor to form an inhibitory complex, stabilizing the association of Smad7 with the receptor, or STRAP acting synergistically Smad7 without physical interactions, or combinations of the foregoing mechanisms.

Many WD40 repeat proteins form multi-protein complexes, sometimes interacting with other proteins through the WD40 repeat region. Such proteins present a changeable surface for protein-protein interaction and are capable of protein-induced conformational changes. Interaction of WD40 repeat proteins with partner proteins have been shown to require residues that are distributed along the length of the protein but come dose together in the folded protein, as described previously for Tup-1 and Gβ subunit (Komachi, K., and A. D. Johnson (1997) Mol. Cell Biol. 17:6023–6028; Lambright, D. G., et al (1996) Nature 379:311–319).

In Example 4 it was observed that STRAP associates with Smad7 and not with the mutant of Smad7, Smad7-Δ408, which is consistent with the functional cooperation of STRAP with Smad7, and not with the mutant in transcriptional repression. This is expected because this mutation in Smad7 interferes with receptor binding and disrupts its inhibitory activity. STRAP(1-294) can also associate with Smad7 and shows synergistic inhibition. Other regions of Smad7 including the C-terminus or the overall three-dimensional structure of this protein are also contemplated for binding with STRAP. In contrast, STRAP also binds with Smad6, but shows no cooperation with Smad6 in transcriptional repression. While it is not applicants' desire to be bound by a particular mechanism of operation, these observations suggest that direct protein-protein interaction is an aspect of the observed functional cooperation between STRAP and Smad7.

STRAP forms a ternary complex with Smad7 and type I receptor in presence of TGF-β signaling, suggesting that binding of Smad7 to the receptor occurs cooperatively with STRAP. In the absence of ligand, Smad7 is found to be predominantly localized in the nucleus and accumulates in cytoplasm upon TGF-β receptor activation (Itoh, S., et al. (1998) J. Biol. Chem. 273:29195–29201). Thus, while it is not applicants' desire to be bound by a particular mechanism of action, it is envisioned that STRAP recruits Smad7 from the cytosol to facilitate its association with the activated receptor complex Furthermore, STRAP stabilizes the interaction between Smad7 and the activated type I receptor in a dose-dependent manner.

Similarly, Smad7 can also enhance the binding between STRAP and the receptor. This is supported by the observation that Smad7 strongly induces receptor-mediated phosphorylation of STRAP in vivo. Examples 1–4 indicate that by interacting with the receptor complex and Smad7, STRAP recruits Smad7 to the activated receptor to form a complex and stabilizes Smad7-receptor complexes, which is critical for Smad7 to prevent Smad2/Smad3 access to the receptor. While it is not applicants' desire to be bound by a particular mechanism of action, it is envisioned that these observations characterize an aspect of how STRAP synergizes with Smad7 to block TGF-β mediated transcriptional responses.

As the number of serine/threonine kinase receptors per cell are low depending on the cell type and only a small fraction must be activated for biological responses (Dyson, S. and J. B. Gurdon (1998) Cell 93:557–568), facilitating interactions between the receptor complex and Smad7 is envisioned to be of significance in vivo. Many WD40 repeat proteins are involved in signal transduction, such as the β-subunit of heterotrimeric G proteins, RACK1. FAN, PLAP, the Bα subunit of protein phosphatase 2A, and TRIP-1 (Chen, R.-H., et al. (1995) Nature 377:548–552; Griswold-Prenner, I., et al. (1998) Mol. Cell Biol. 18:6595–6604; Klages, S. A., et al. (1996) Cell 86:937–947). The proteins also help to assemble macromolecular complexes necessary for signaling, as shown for Gβ subunit (Clapham, D. E., and E. J. Neer (1993) Nature 365:403–406). Analogous to the recruitment of signaling components to receptor tyrosine kinases, it is contemplated that STRAP has a role generally in recruiting downstream regulatory molecules to receptor serine/threonine kinases.

Example 4 also shows that the C-terminus of STRAP is required for its phosphorylation in vivo. The physical interaction of STRAP with the receptor complex raises the possibility that STRAP is a substrate of the receptors. This Example shows that increase in the phosphorylation of STRAP requires the kinase achy of receptors in vivo, but STRAP does not appear to be a direct substrate of the receptors in in vitro kinase assays. It is possible that only TβR-I is capable of enhancing this phosphorylation in vivo, and the increase in STRAP phosphorylation by TβR-II is through activation of the endogenous type I receptor. Smad7 alone has little effect on the phosphorylation of STRAP but it can strongly stimulate this receptor-mediated phosphorylation, perhaps by stabilizing the complex between the receptors and STRAP.

The C-terminus of STRAP is required for its phosphorylation and for binding with other phosphoproteins, suggesting the presence of an alternate kinase that might phosphorylate STRAP. STRAP(1-294) interacts with Smad7 and synergizes with it in the inhibition of TGF-β signaling. Thus, phosphorylation of STRAP is dispensable for this function. These data suggest that the increase in STRAP phosphorylation might be mediated by either TGF-β receptors indirectly in vivo, receptor associated kinases or STRAP associated kinases that are activated by TGF-β receptors in a multimeric complex involving Smad7.

STRAP synergizes with Smad7, and not with Smad6, for blocking the transcriptional responses initiated by TGF-β. While it is not applicants' desire to be bound by a particular mechanism of operation, this could be an aspect of a mechanism to maintain specificity and suppress cross talk between signaling pathways. However, it is contemplated that STRAP can function differently with Smad6 and that it can also cooperate with Smad7 for inhibiting activin and BMP signaling. Although STRAP is expressed in a wide variety of tissues and cell lines, its expression level varies significantly. It is possible that Smad7 requires STRAP for its natural inhibitory activity.

Recently, Smad7 has been reported to be predominantly localized in the nucleus in the absence of ligand (Itoh, S., et al. (1998) *J. Biol. Chem.* 273:29195–29201), and thus STRAP is contemplated to synergize with Smad7 in this aspect. Additionally, STRAP could form complexes with other components, known or as yet unidentified, of the TGF-β signaling pathway and could recruit them to the activated receptor complex. A scaffolding function of STRAP is thus also envisioned to be an aspect of regulating the biological functions of TGF-β.

Example 5

STRAP Potentiates TGF-β-mediated Growth Inhibition

Figure 11:
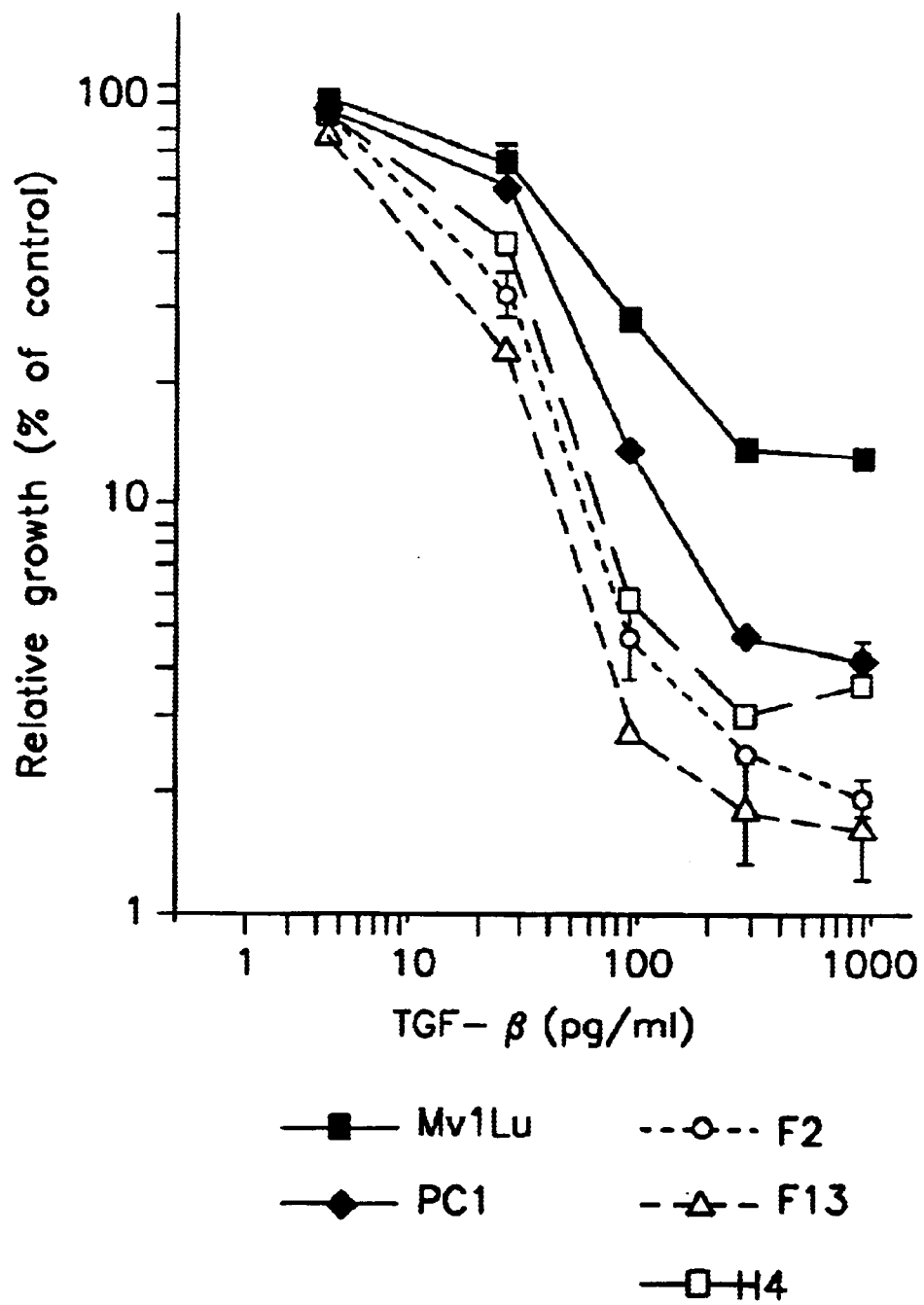
FIG. 11 is a graph depicting that STRAP potentiates TGF-β-mediated growth inhibition. Mv1Lu cells alone or stably transfected with vector (PC1) or STRAP-Flag (F2. F13) or STRAP-HA(H4) were incubated with the indicated concentration of TGF-β1 for 20 hours, then labeled with $^3$H-thymidine for 2 hours. The cells were fixed and solubilized in NaOH at room temperature. The radioactivity incorporated into DNA was determined by liquid scintillation counting.

Mv1Lu cells alone or stably transfected with vector (PC1) or STRAP-Flag (F2, F13) or STRAP-HA(H4) were incubated with the indicated concentration of TGF-β1 for 20 hours, then labeled with $^3$H-thymidine for 2 hours. The cells were fixed and solubilized in NaOH at room temperature. The radioactivity incorporated into DNA was determined by liquid scintillation counting. The data are presented in the graph of FIG. 11, which plots relative growth (% of control sample) versus TGF-β concentration in picograms (pg) per milliliter (ml). Thus, STRAP enhances the anti-proliferative effect of TGF-β.

REFERENCES

Abdollah, S., et al. (1997) *J. Biol. Chem.* 272:27678–27685.
Adelman et al. (1983) *DNA* 2:183.
Atfisano, L., et al. (1994) *Blochim. Biophys. Acta* 1222:71–80.
Ausubel et al. (1992) *Curent Protocols in Molecular Biology*, J. Wylie & Sons. New York, N.Y.
Barinaga, M. (1999) *Science* 283:1247–1249.
Bassing et al., *Science* 263:87–89 (1994).
Bodanszky et al. (1976) *Peptide Synthesis*, J. Wiley & Sons, New York, N.Y., $2^{1\ nd}$ Ed.
Ca¢rcamo, J., et al. (1994) *Mol. Cell Biol.* 14:3810–3821.
Chen, R.-H. and R. Deryndc (1994) *J. Biol. Chem.* 269:22868–22874.
Chen et al., *EMBO J.* 16:3866–3876 (1997).
Chen, X., et al. (1996) *Nature* 383:691–696.
Chen, R.-H., et al. (1995) *Nature* 377:548–552.
Chen, Y., et al. (1997) *Proc. Natl. Aced. Sci. USA* 94:12938–12943.
Chen, Y., et al. (1998) *J. Biol. Chem.* 273:8225–8231.
Chien et al., *Proc. Natl. Acad. Sci. USA* 88:9578–9582 (1991).
Choy, L., and R. Derynck (1998) *J. Biol. Chem.* 273:31455–31462.
Clapham, D. E., and E. J. Neer (1993) *Nature* 365:403–406.
Crea et al. (1978) *Proc. Natl. Aced. Sci. U.S.A*, 75:5765.
Datta, P. K., and S. Bagchi. 1994. *J. Biol. Chem.* 269: 25392–25399.
Datta, P. K., et al. (1998) 273:34671–34674.
Dennier, S. et al. (1998) *EMBO J.* 17:3091–3100.
Derynck, R., and X.-H. Feng (1997) *Biochkn. Biophys. Acta.* 1333:F105–F150.
Durfee at al., *Genes Dev.* 7:555–569 (1993).
Dyson, S. and J. B. Gurdon (1998) *Cell* 93:557–568.
Eichenlaub et al. *R. J. Bacteriol* 138:559–566, 1979.
Engel, M. E., et al. (1998) *J. Cell. Biochem.* 30/31:111–122.
Feng, X-H., et al. 1998. *Genes Dev.* 12:2153–2163.
Gillmor et al. (1997) *Nature Struct. Biol.* 4:1003–1009.
Green et al. (1989) *J. Invest. Dernatol.* 93:4868–491.
Griswold-Prenner, I., et al. (1998) *Mol. Cell Biol.* 18:6595–6604.
Harper et al., *Cell* 75:805–816 (1993).
Hata. A, et al. (1998) *Genes Dev.* 12:186–197.
Hayashi, H., et al. (1997) *Cell* 89:1165–1173.
Heldin, C.-H. et al. (1997) *Nature* 390:465–471.
Henis, Y. I., et al. (1994) *J. Cell Biol.* 126:139–154.
Hoodless, P. A, et al. (1996) *Cell* 85:489–500.
Hopp, U.S. Pat. No. 4,554,101.
Howell et al. (1988) *Antibodies A Laboratory Manuel*, (Cold Spring Harbor Laboratory).
Imamura, T., M. et al. (1997) *Nature* 389: 622–626.
Ishisak, A., et al. (1999) *J. Biol. Chem.* 274:13637–13642.
Itoh, S., et al. (1998) *J. Biol. Chem.* 273:29195–29201.
Janknecht, R., et al. 1998. *Gennes Dev.* 12:2114–2119.
Kawabata, M. et al. (1995) *J. Biol. Chem.* 270:29628–29631.
Kawabata, M. et al. (1998) *EMBO J.* 17:4056–4065.
Keeton, M. R., et al. (1991) *J. Biol. Chem.* 266:23048–23052.
Keski-Oja et al., *J. Cell Biochem.* 33:95 (1987).
Kiages, S. A., et al. (1996) *Cell* 86:937–947.
Komachi, K., and A D. Johnson (1997) *Mol. Cell Biol.* 17:6023–6028.
Kretzschmar. M., et al. (1997) *Genes Dev.* 11:984–995.
Kretzschmar, M., and J. Massague¢ (1998) *Curr. Opin. Genet. Dev.* 8:103–111.
Kyte et al. (1982) *J. Mol. Biol.* 157: 105.
Labbe¢. E., et al. (1998) *Mol. Cell* 2:109–120.
Lagna, G. et al. (1996) *Nature* 383:832–836.
Lam et al., *J. Biol. Chem.* 270:26511–26522 (1995).
Lambright, D. G., et al (1996) *Nature* 379:311–319.
Liu, F., et al. (1997) *Genes Dev.* 11:3157–3167.
Lu. X., et al. (1997). *Proc. Natl. Aced. Sci. USA* 94:10669–10764.
Lu, P.-J., et al. (1999) *Science* 283: 1325–1328.
Macias-Silva, M., et al. (1996) *Cell* 87:1215–1224.
Marshall, C. J. *Cell* 80:179–185 (1995).
Massague, *Cell* 49:437 (1987).
Massague¢ et al. *Trends Cell Biol.* 7:187–192 (1997).
Massague¢, J. (1998) *Annu. Rev. Biochem.* 67:753–791.
McOmie, "Protective Groups in Organic Chemistry", Plenum Press, New York, (1973)
Meienhofer, "Hormonal Proteins and Peptides", Vol.2, p.46, Academic Press (New York) (1983).
Merrifield, *Adv Enzymol*, 32:221–96, 1969; Fields et al., *Int. J. Peptide Protein Res.*, 35:161–214, 1990.
Messing et al. (1981) *Third Cleveland Symposium on Macromolecules and Recombinant DNA*, Editor A. Walton, (Elsevier, Amsterdam).
Nakao, A., at al. (1997) *Nature* 389:631–635.
Needleman et al., *J. Mol. Biol.*, 48:443 (1970).
Neer. E. J., et al. (1994) *Nature* 371:297–300.
Nishimura, R. et al. (1998) *J. Biol. Chem.* 273:1872–1879.
Roberts, A. B. & Sporn, M. B. in *Peptide Growth Factors and their Receptors Part* I(eds Sporn, M. B. & Roberts, A. B.)419–472 (Springer-Heidelberg, 1990).
Sambrook et al. (1989) *Molecular Cloning: A Laboratory Manual* (Cold Sprng Harbor Laboratory Press, Cold Spring Harbor, N.Y.).
Schroder et al., "The Peptides", Vol. 1, Academic Press (New York) (1965).
Smith et al., *Adv. Appl. Math.* 2:482 (1981).
SouchelnyWskyl, S., et al. (1997) *J. Biol. Chem.* 272:28107–28115.
Souchelnytskyl, S., et al. (1998) *J. Biol. Chem.* 273:25364–25370.
Standaert et al., *Nature* 346:671–674 (1990).
Steward et al., "Solid Phase Peptide Synthesis", W. H. Freeman Co., San Francisco (1969).

U.S. Pat. No. 5,162,215
U.S. Pat. No. 5,583,103
U.S. Pat. No. 5,399,346
U.S. Pat. No. 5,741,957
U.S. Pat. No. 5,436,288
U.S. Pat. No. 2.868,691
U.S. Pat. No. 3,095,355
U.S. Pat. No. 4,196,265
U.S. Pat. No. 4,244,946
U.S. Pat. No. 4,683,202
U.S. Pat. No. 4,686,283
U.S. Pat. No. 4,736,866
U.S. Pat. No. 5,120,535
U.S. Pat. No. 5,780,436
U.S. Pat. No. 5,234,933
U.S. Pat. No. 5,279,833
U.S. Pat. No. 5,286,634
U.S. Pat. No. 5,326,902
U.S. Pat. No. 5,627,158
U.S. Pat. No. 5,625,125
U.S. Pat. No. 5,489,742
U.S. Pat. No. 5,550,316
U.S. Pat. No. 5,770,609
U.S. Pat. No. 5,573,933
U.S. Pat. No. 5,614,396
U.S. Pat. No. 5,651,964
U.S. Pat. No. 5,734,033
U.S. Pat. No. 5,641,484
U.S. Pat. No. 5,643,567
U.S. Pat. No. 5,645,999
U.S. Pat. No. 5,646,008
U.S. Pat. No. 5,648,061

Wang et al., *Cell* 86:435–444 (1996).
Wetmur & Davidson (1968) *J. Mol. Boil.* 31:349–370.
Wieser, R. et al. (1995) *EMBO J.* 14:2199–2208.
Wieser et al., *EMBO J.* 14:2199–2208 (1995).
WO 93/25521, published Dec. 23, 1993.
Wrana et al., *Cell* 71:1003–1014 (1992).
Yamashita, H. et al. (1994) *J. Bol. Chem.* 269:20172–20178.
Zhlang, Y., et al. (1997) *Curr. Biol.* 7:270–276.
Zhang, Y., et al. (1998) *Nature* 394:909–913.
Zhou, S., et al. (1998) *Mol. Cell* 2:121–127.
Zimmer et al., *Peptides* 1992, pp. 393–394, ESCOM Science Publishers, B. V., 1993.

It will be understood that various details of the invention may be changed without departing from the scope of the invention. Furthermore, the foregoing description is for the purpose of illustration only, and not for the purpose of limitation—the invention being defined by the claims.

---

What is claimed is:

1. An isolated and purified polynucleic acid encoding a biologically active Serine-Threonine Kinase Receptor Associated Protein (STRAP) polypeptide, having TGF-β modulating activity, wherein the STRAP polypeptide is at least about 99% identical to a sequence as set forth in SEQ ID NO: 2.

2. The polynucleic acid of claim 1, wherein the STRAP polypeptide is SEQ ID NO: 2.

3. The polynucleic acid of claim 1, wherein the polynucleic acid has the sequence set forth in SEQ ID NO: 1.

4. The polynucleic acid of claim 1, further defined as comprising at least a 1,000 nucleotide long contiguous stretch of the polynucleic acid sequence of SEQ ID NO: 1.

5. A composition comprising the polynucleic acid of claim 1, and a carrier.

6. A method of preparing a STRAP polypeptide, comprising: transforming a cell with the polynucleic acid of claim 1 to produce STRAP under conditions suitable for the expression of said polypeptide.

7. A recombinant vector comprising the polynucleic acid of claim 1.

8. The recombinant vector of claims 7, wherein the vector is a recombinant expression vector.

9. A composition comprising the vector of claim 7, and a carrier.

10. A recombinant host cell comprising the recombinant vector of claim 7.

11. The recombinant host cell of claim 10, wherein the host cell is a prokaryotic cell.

12. The recombinant host cell of claim 10, wherein the host cell is a eukaryotic cell.

13. A composition comprising the recombinant host cell of claim 10, and a carrier.

* * * * *